United States Patent
Asano et al.

(10) Patent No.: US 10,730,909 B2
(45) Date of Patent: Aug. 4, 2020

(54) METHOD OF PRODUCING AN ACTIVE-FORM MUTANT ENZYME

(71) Applicant: Toyama Prefectural University, Toyama (JP)

(72) Inventors: Yasuhisa Asano, Toyama (JP); Daisuke Matsui, Toyama (JP); Yuko Oku, Toyama (JP)

(73) Assignee: Toyama Prefectual University (JP)

( * ) Notice: Subject to any disclaimer, the term of this patent is extended or adjusted under 35 U.S.C. 154(b) by 0 days.

(21) Appl. No.: 15/511,706

(22) PCT Filed: Jun. 10, 2016

(86) PCT No.: PCT/JP2016/067392
§ 371 (c)(1),
(2) Date: Mar. 16, 2017

(87) PCT Pub. No.: WO2016/199898
PCT Pub. Date: Dec. 15, 2016

(65) Prior Publication Data
US 2018/0170960 A1 Jun. 21, 2018

(30) Foreign Application Priority Data

Jun. 10, 2015 (JP) .................. 2015-117808

(51) Int. Cl.
| | | |
|---|---|---|
| *C07K 4/12* | (2006.01) | |
| *C12N 15/70* | (2006.01) | |
| *C12N 9/88* | (2006.01) | |
| *C12N 15/09* | (2006.01) | |
| *C12N 9/00* | (2006.01) | |
| *C12N 15/01* | (2006.01) | |

(52) U.S. Cl.
CPC .............. *C07K 4/12* (2013.01); *C12N 9/00* (2013.01); *C12N 9/88* (2013.01); *C12N 15/01* (2013.01); *C12N 15/09* (2013.01); *C12N 15/70* (2013.01); *C12Y 101/03* (2013.01); *C12Y 104/01002* (2013.01)

(58) Field of Classification Search
None
See application file for complete search history.

(56) References Cited

U.S. PATENT DOCUMENTS

| | | | | |
|---|---|---|---|---|
| 6,333,186 | B1* | 12/2001 | Wittekind | C12N 9/506 435/183 |
| 2011/0126322 | A1 | 5/2011 | Fernandez Tiburcio et al. | |
| 2011/0144000 | A1* | 6/2011 | Egesten | A61K 38/193 514/2.4 |
| 2013/0273585 | A1 | 10/2013 | Appaiah et al. | |

FOREIGN PATENT DOCUMENTS

| | | |
|---|---|---|
| JP | H119274 A | 1/1999 |
| JP | H11335392 A | 12/1999 |
| JP | 2001503614 | 3/2001 |
| JP | 2002534084 A | 10/2002 |
| JP | 2004105070 A | 4/2004 |
| JP | WO2009000098 A | 12/2008 |
| JP | 2010532324 A | 10/2010 |
| JP | 2011046686 A | 3/2011 |
| JP | 2012044888 A | 3/2012 |
| JP | 2012116816 A | 6/2012 |
| JP | 2012179062 A | 9/2012 |
| JP | 2015167478 A | 9/2015 |
| WO | WO9814467 A1 | 4/1998 |
| WO | WO200040707 A1 | 7/2000 |
| WO | WO2006041226 A1 | 4/2006 |
| WO | WO2006061906 A1 | 6/2006 |

OTHER PUBLICATIONS

Li et al. Biotechnol Bioeng. Jul. 2014;111(7):1273-87. Epub May 6, 2014. (Year: 2014).*
Accession Q9SI64. Dec. 1, 2000. (Year: 2000).*
Buchan et al. Nucleic Acids Res. Jul. 2013;41(Web Server issue):W349-57. Epub Jun. 8, 2013. (Year: 2013).*
Leman et al. Proteins. Jul. 2013;81(7):1127-40. Epub Apr. 10, 2013. (Year: 2013).*
Ishida et al. Sci Rep. 2016; 6: 26998. Published online Jun. 6, 2016. (Year: 2016).*
International Preliminary Report on Patentability; dated Dec. 14, 2017 for PCT Application No. PCT/JP2016/067392 in both English and Japanese.
Extended European Search Report; dated Mar. 2, 2018 for EP Application No. 16807603.2.
Romans, M., et al. "The generation of multicopy recombinant strains." Methods in molecular biology (Clifton, NJ) 103 (1998): 55.
Gleeson, M. A., et al. "Generation of protease-deficient strains and their use in heterologous protein expression." Methods in molecular biology (Clifton, NJ) 103 (1998): 81.
Cremata, J. A., et al. "Glycosylation profiling of heterologous proteins." Methods in molecular biology (Clifton, NJ) 103 (1998): 95.

(Continued)

*Primary Examiner* — Christian L Fronda
(74) *Attorney, Agent, or Firm* — Mendelsohn Dunleavy, P.C.

(57) ABSTRACT

A method for expressing, as a soluble protein or an active-form mutant enzyme, an enzyme that cannot be expressed as a soluble protein or an active-form enzyme in a heterologous expression system or that is obtained in a minute amount even when an active-form enzyme is expressed, the method including a technique for selecting an effective mutation site and a mutated amino acid. A new active-form mutant enzyme is also disclosed. The method involves: specifying an insoluble protein or an inactive-form enzyme; specifying a hydrophilic amino acid in a hydrophobic domain and/or a hydrophobic amino acid in a hydrophilic domain of an α-helix structure portion of the insoluble protein or the inactive-form enzyme and preparing a gene that codes for an amino acid sequence in which a substitution is made to the hydrophilic amino acid in the hydrophobic domain and/or the hydrophobic amino acid in the hydrophilic domain.

7 Claims, 19 Drawing Sheets

Specification includes a Sequence Listing.

(56) References Cited

OTHER PUBLICATIONS

Andersson, Stefan, et al. "Cloning, structure, and expression of the mitochondrial cytochrome P-450 sterol 26-hydroxylase, a bile acid biosynthetic enzyme." Journal of Biological Chemistry 264.14 (1989): 8222-8229.

Asano, Yasuhisa, et al. "Functional expression of a plant hydroxynitrile lyase in *Escherichia coli* by directed evolution: creation and characterization of highly in vivo soluble mutants." Protein Engineering Design and Selection 24.8 (2011): 607-616.

Kapust, RB, and DS Waugh. "*Escherichia coli* Maltose-Binding Protein is Uncommonly Effective at Promoting the Solubility of Polypeptides to Which it is Fused." Protein science 8.8 (1999): 1668-1674.

Nakano, Shogo, and Yasuhisa Asano. "Protein evolution analysis of S-hydroxynitrile lyase by complete sequence design utilizing the INTMSAlign software." Scientific reports 5 (2015).

Sørensen, Hans Peter, and Kim Kusk Mortensen. "Soluble expression of recombinant proteins in the cytoplasm of *Escherichia coli*." Microbial cell factories 4.1 (2005): 1.

Kyte, Jack, and Russell F. Doolittle. "A simple method for displaying the hydropathic character of a protein." Journal of molecular biology 157.1 (1982): 105-132.

Pédelacq, Jean-Denis, et al. "Engineering soluble proteins for structural genomics." Nature biotechnology 20.9 (2002): 927-932.

Nishihara, Kazuyo, et al. "Chaperone coexpression plasmids: Differential and synergistic roles of DnaK-DnaJ-GrpE and GroEL-GroES in assisting folding of an allergen of Japanese cedar pollen, Cryj2, in*Escherichia coli*." Applied and Environmental Microbiology 64.5 (1998): 1694-1699.

Database Uniprot [online], Accessin No. P40807, <http://www.uniprot.org/uniprot/P40807.txt?version=42> May 1, 2005 uploaded, [retrieved on Aug. 22, 2016] Definition: Ornithine decarboxylase 1 (EC 4.1.1.17) (ODC).

Database Uniprot [online], Accessin No. Q9VCN3, <http://www.uniprot.org/uniprot/Q9VCN3.txt→version=113> May 27, 2015 uploaded, [retrieved on Aug. 22, 2016] Definition: Glutamate dehydrogenase.

International Search Report; dated Sep. 6, 2016 for PCT/JP2016/067392.

Partial Supplementary European Search Report; dated Mar. 2, 2018 for EP Application No. 16807603.2.

Murby, Maria, et al. "Hydrophobicity engineering to increase solubility and stability of a recombinant protein from respiratory syncytial virus." The FEBS Journal 230.1 (1995): 38-44.

Notice of Reasons for Refusal for corresponding Japanese application No. 2017-523718; dated Jun. 11, 2020; 11 pages (Machine Translation).

Helical wheel image, bioinf.cs.ucl.ac.uk, 2016 [retrieved Jun. 10, 2020] Retrieved from Internet: <URL: http://bioinf.cs.ucl.ac.uk/psipred/result/4ea2b13c-6835-11e6-8ba5-00163e110593> (1 page).

Amino Acid Sequence for Helical Structure, bioinformatics.nl, [retrieved on Jun. 10, 2020] Retrieved from Internet: <URL: ittp://www.bioinformatics.nl/emboss-explorer/output/145936/> (1 page).

Extended European Search Report for corresponding European application No. 20150372.9; dated Jun. 5, 2020 (5 pages).

Suemori, Akio. "Conserved and non-conserved residues and their role in the structure and function of p-hydroxybenzoate hydroxylase." Protein Engineering, Design & Selection 26.7 (2013): 479-488.

Donnelly, Dan, et al. "Modeling a-helical transmembrane domains: the calculation and use of substitution tables for lipid-facing residues." Protein Science 2A (1993): 55-70.

\* cited by examiner

Fig.2
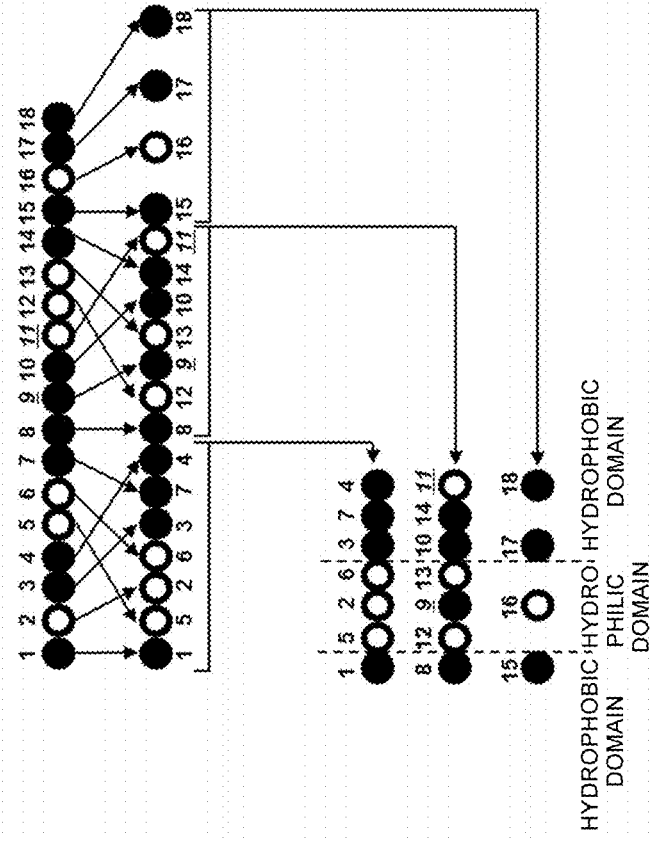
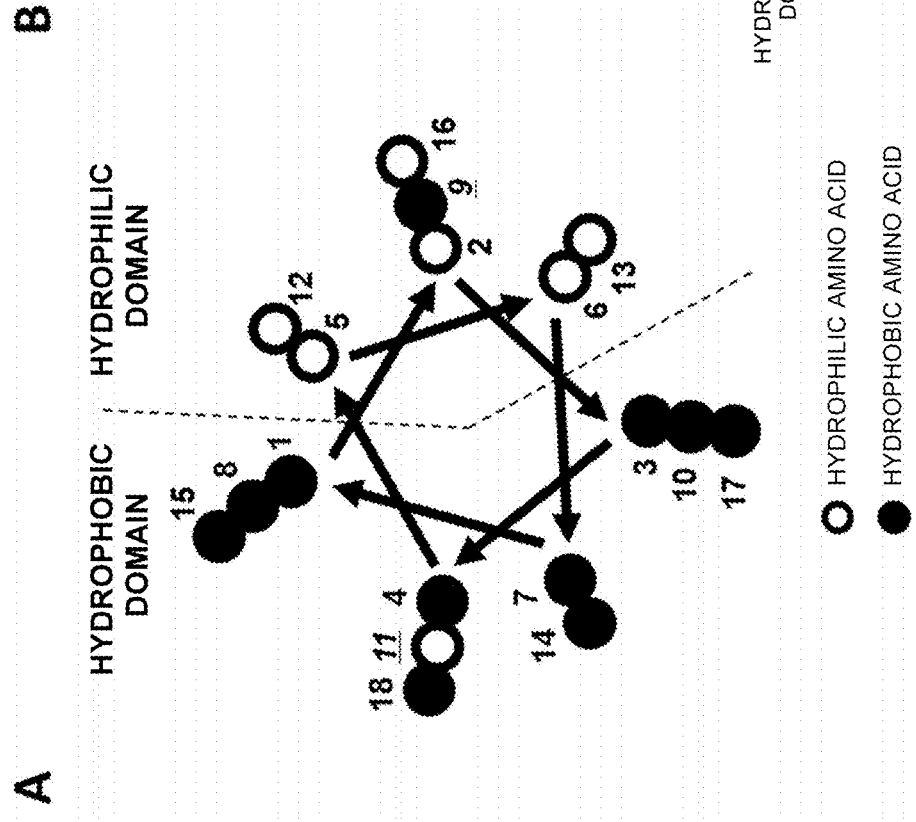
A: HELICAL WHEEL AND
B: LINEAR REPRESENTATION OF HELICAL WHEEL

APPLICATION TO ACTUAL HELIX CONTAINING 444 AND 455 OF MOX

Fig.7-1

SDS-PAGE OF PURIFIED LUC I80K AND A177D MUTANT ENZYMES

Fig.14

SECONDARY STRUCTURE
PREDICTION OF DmODC

A

Conf: ███████▪▫▫▫▫█▫▫██████████▫▫██████▫█████▫
Pred: ────────◇────◻◻◻────────────────◇──◻◻
Pred: CCCCCCCCEECCCCCHHHHHHHHCCCCCCCEEEEEHHH
AA:   MAAATPEIQFYERELNIRRVIEECDLQRLDQALNICDLSS
      10        20        30        40

Conf: █████████████▫▫▫▫▫▫████████████▫████▫
Pred: ◻◻◻◻◻◻◻◻◻◻──◇────◻◻◻◻◻◻◻◻───
Pred: HHHHHHHHHHHCCCCCEEEECCCCCHHHHHHHHCCCCE
AA:   VERNVRLWQKLLPRIKPFYAVKCNDDPMVVRLLAQLGAGF
      50        60        70        80

Conf: ▫██████████▫█████████▫▫▫████▫▫██████████▫
Pred: ◇──◻◻◻◻◻───◇────◻◻◻◻───
Pred: EECCHHHHHHHHCCCCCCCEEEECCCCCCCHHHHHHHHCC
AA:   DCASKNEVKLVLGFDVSPERIIFANPCRPVSHLEYAKEHQ
      90        100       110       120

Conf: █████▫█████████▫████████████████████▫
Pred: ──◇─◻◻◻◻◻◻──────────────
Pred: CCEEECCCHHHHHHHHHHCCCCEEEEEEECCCCCCCCCC
AA:   VSNGTVDNEFEVYKLHTHYPNSNLIVRFKSEAKEAQCPLG
      130       140       150       160

Conf: ███████▫▫████████████▫▫████▫▫▫██████████▫
Pred: ──◻◻◻◻◻──◇────────────◻
Pred: CCCCCCCCCCHHHHHHHHHHCCCEEEEEEECCCCCCCCHH
AA:   DKFGCDADVDAAALMLLAKSLELKVTGTSFHVGSGCSELQ
      170       180       190       200

Conf: █████████████████▫███████▫█████████████▫
Pred: ◻◻◻◻◻◻◻◻◻◻◻◻────◇────◻
Pred: HHHHHHHHHHHHHHHHCCCCCCEEECCCCCCCCCCCCCH
AA:   AYDRAIKKAKNLFKFGALLGYDMDFLDIGGGFPGSDDVKF
      210       220       230       240

Conf: █████████████▫█████████▫▫▫▫▫███████████▫
Pred: ◻◻◻◻◻──◇──────────
Pred: HHHHHHHHHHHHHCCCCCCEEEECCCCCCCCCCCEEEEEE
AA:   EQIAESVNTSVQRHFPDERVHIIAEPGRFFVAAACTLVCK
      250       260       270       280

Conf: █████▫▫▫▫▫██████▫████▫█▫▫▫▫▫▫▫▫▫▫██▫██▫
Pred: ◇─────◇────────────◇
Pred: EEEEEEECCCCCCEEEEEECCCCCCCCCCCCCCCCCEEE
AA:   IHAKREIRNEAGKLDTVMYYLNDGVYGSFNCILYDHQVVI
      290       300       310       320

Conf: ████▫▫█████▫▫▫▫████▫█▫█▫▫▫▫▫▫▫█████████▫
Pred: ─◇────◇────◇──────
Pred: EEEECCCCCCCCEEEEEECCCCCCCCCEEECCCCCCCCCC
AA:   AEHYQDNAESLPHLKSLIWGPSCDALDQISEDLHLPNLNR
      330       340       350       360

Conf: █████████▫▫▫▫▫████████████▫▫████▫
Pred: ─◇─────────────────◇──
Pred: CCEEEECCCCCCCCCCCCCCCCCCCCEEEECC
AA:   GDLLGFRNMGAYTMPIASAFNGFEVPKTLYFQAI
      370       380       390

Fig.15

SECONDARY STRUCTURE
PREDICTION OF DmGluDH

SEQUENCE OF hGH
M F P T I P L S R L F D N A M L R A H R L H Q L A F D T Y Q E F E E A
Y I P K E Q K Y S F L Q N P Q T S L C F S E S I P T P S N R E E T Q Q
K S N L E L L R I S L L L I Q S W L E P V Q F L R S V F A N S L V Y G
A S D S N V Y D L L K D L E E G I Q T L M G R L E D G S P R T G Q I F
K Q T Y S K F D T N S H N D D A L L K N Y G L L Y C F R K D M D K V E
T F L R I V Q C R S V E G S C G F

SEQUENCE LISTING

```
<160> NUMBER OF SEQ ID NOS: 11

<210> SEQ ID NO 1
<211> LENGTH: 1755
<212> TYPE: DNA
<213> ORGANISM: Chamberlinius hualienensis

<400> SEQUENCE: 1
caaccaaagg aaacttatga ctttatcgtt gtgggagctg gttctgctgg atcagtagta      60
gctaatcgtt tgagtgaact cccaaatata aaagttttgc tgttggaagc cggtggaaat     120
gagactgaaa ccagcgaagt gccactattt gcaggacaat tacaactttc tcctctcgat     180
tggaacttta catcgacacc acagaagaac tcctgtttgg cttttggaa tcaaacttgt      240 ctctggccac aaggcaaagt tttgggtgga tcaagtgttc tcaattacat gatctttgtt     300
agaggaaaca aaaagattt tgacgattgg gcagcattgg gtaatgtggg ttgggactac      360
aacagtgttt tgccatactt tatcaagatg gaaaacttca ctggacctag tactgatgct     420
gcaatccgtg gaaagactgg tcctcttaca gtcggttttg tgccatatca caccgtttta     480
gctgatactt tcgtctcggc tggaaatgaa aatggataca atacagttga ttacaatgga     540
cacactcaaa caggtgtaca acgaattcaa gcaactactc gtgatggtca acgatgcagt     600
acaaacaaag cttatttatg gccaattgtg cacacgagac caaactttgt attgaaaact     660
cacgccactg tcttgaaggt tttacttaac gataaaaaag ccgctattgg agttaagtat     720
gccatcaatg gcgaagaaca taccgcatta gcatctaaag aagttattct ttctgctgga     780
gcactcaact ctccacaatt acttatgctc tcaggcattg gtgatcctac agatttgcaa     840 ccattcgaa ttaaagtttt agtcgagaat aagggtgttg gaaagaactt ccaagatcac      900
gttgcctgcg gaggtgttga atggcttatt gatcaaccag tctcactagt cacaagtcga     960
```

-continued

```
gttgtaaatg accaaacgat aaaggaatgg aaagatcatg gaactggtcc tttgactatt      1020
ccaagtgacg tggaagccac tgcatttgtt cacactacaa ccgaatacgc tgctgaagat      1080
ttccctgata ttcaactctt ctatttcagt ggtactccag catctgatgg tggaactggt      1140
gccagataca caactggatt taccaacgct tcatggaatg gatactataa agaaatcgaa      1200
aacaaagacg ctttctctat ctatccagtg ttacttcgac caaaaagcag aggatatatc      1260
ggtcttagaa gtgctaatcc ttatgatgct ccagtcattg agccagctta cttcaccgac      1320
cctggaagag ttgacattga tacgatggtt cgaggcgtac acgttgctct aactttgga      1380 aactcaaagg cattttctaa atttggagct aaattgcaca atgccacatt ccctggatgc      1440
gaaccatatc ccttacacag cgatgcttat tgggaatgtt tagctagaca ttttatcagc      1500
atcaacttcc atcatccag ctcttgtact atgggagata gaaccaagac tccattagct      1560
gtggttgaca accgattacg agtctatggt gtaaaaaatc ttcgcgttat tgatgctgca      1620
attataccct tgtctccatc tggaaacacc aatggtccaa ccatcatgat tggagagaaa      1680
ggctccgatt tgattaagga agattggaaa cttaaaaccc catctggact cgagcaccac      1740
caccaccacc actga                                                      1755
```

\<210> SEQ ID NO 2
\<211> LENGTH: 584
\<212> TYPE: PRT
\<213> ORGANISM: Chamberlinius hualienensis

\<400> SEQUENCE: 2

```
Gln Pro Lys Glu Thr Tyr Asp Phe Ile Val Val Gly Ala Gly Ser Ala
1               5                  10                  15

Gly Ser Val Val Ala Asn Arg Leu Ser Glu Leu Pro Asn Ile Lys Val
            20                  25                  30

Leu Leu Leu Glu Ala Gly Gly Asn Glu Thr Glu Thr Ser Glu Val Pro
        35                  40                  45

Leu Phe Ala Gly Gln Leu Gln Leu Ser Pro Leu Asp Trp Asn Phe Thr
    50                  55                  60

Ser Thr Pro Gln Lys Asn Ser Cys Leu Ala Phe Trp Asn Gln Thr Cys
65                  70                  75                  80

Leu Trp Pro Gln Gly Lys Val Leu Gly Gly Ser Ser Val Leu Asn Tyr
                85                  90                  95

Met Ile Phe Val Arg Gly Asn Lys Lys Asp Phe Asp Asp Trp Ala Ala
            100                 105                 110

Leu Gly Asn Val Gly Trp Asp Tyr Asn Ser Val Leu Pro Tyr Phe Ile
        115                 120                 125

Lys Met Glu Asn Phe Thr Gly Pro Ser Thr Asp Ala Ala Ile Arg Gly
    130                 135                 140

Lys Thr Gly Pro Leu Thr Val Gly Phe Val Pro Tyr His Thr Val Leu
145                 150                 155                 160

Ala Asp Thr Phe Val Ser Ala Gly Asn Glu Asn Gly Tyr Asn Thr Val
                165                 170                 175

Asp Tyr Asn Gly His Thr Gln Thr Gly Val Gln Arg Ile Gln Ala Thr
            180                 185                 190

Thr Arg Asp Gly Gln Arg Cys Ser Thr Asn Lys Ala Tyr Leu Trp Pro
        195                 200                 205

Ile Val His Thr Arg Pro Asn Phe Val Leu Lys Thr His Ala Thr Val
    210                 215                 220
```

```
Leu Lys Val Leu Asn Asp Lys Lys Ala Ala Ile Gly Val Lys Tyr
225                 230                 235                 240

Ala Ile Asn Gly Glu Glu His Thr Ala Leu Ala Ser Lys Glu Val Ile
            245                 250                 255

Leu Ser Ala Gly Ala Leu Asn Ser Pro Gln Leu Leu Met Leu Ser Gly
        260                 265                 270

Ile Gly Asp Pro Thr Asp Leu Gln Pro Phe Gly Ile Lys Val Leu Val
    275                 280                 285

Glu Asn Lys Gly Val Gly Lys Asn Phe Gln Asp His Val Ala Cys Gly
290                 295                 300

Gly Val Glu Trp Leu Ile Asp Gln Pro Val Ser Leu Val Thr Ser Arg
305                 310                 315                 320

Val Val Asn Asp Gln Thr Ile Lys Glu Trp Lys Asp His Gly Thr Gly
                325                 330                 335

Pro Leu Thr Ile Pro Ser Asp Val Glu Ala Thr Ala Phe Val His Thr
            340                 345                 350

Thr Thr Glu Tyr Ala Ala Glu Asp Phe Pro Asp Ile Gln Leu Phe Tyr
        355                 360                 365

Phe Ser Gly Thr Pro Ala Ser Asp Gly Gly Thr Gly Ala Arg Tyr Thr
    370                 375                 380

Thr Gly Phe Thr Asn Ala Ser Trp Asn Gly Tyr Tyr Lys Glu Ile Glu
385                 390                 395                 400

Asn Lys Asp Ala Phe Ser Ile Tyr Pro Val Leu Leu Arg Pro Lys Ser
                405                 410                 415

Arg Gly Tyr Ile Gly Leu Arg Ser Ala Asn Pro Tyr Asp Ala Pro Val
            420                 425                 430

Ile Glu Pro Ala Tyr Phe Thr Asp Pro Gly Arg Val Asp Ile Asp Thr
        435                 440                 445

Met Val Arg Gly Val His Val Ala Leu Asn Phe Gly Asn Ser Lys Ala
    450                 455                 460

Phe Ser Lys Phe Gly Ala Lys Leu His Asn Ala Thr Phe Pro Gly Cys
465                 470                 475                 480

Glu Pro Tyr Pro Leu His Ser Asp Ala Tyr Trp Glu Cys Leu Ala Arg
                485                 490                 495

His Phe Ile Ser Ile Asn Phe His Pro Ser Ser Ser Cys Thr Met Gly
            500                 505                 510

Asp Arg Thr Lys Thr Pro Leu Ala Val Val Asp Asn Arg Leu Arg Val
        515                 520                 525

Tyr Gly Val Lys Asn Leu Arg Val Ile Asp Ala Ala Ile Ile Pro Leu
    530                 535                 540

Ser Pro Ser Gly Asn Thr Asn Gly Pro Thr Ile Met Ile Gly Glu Lys
545                 550                 555                 560

Gly Ser Asp Leu Ile Lys Glu Asp Trp Lys Leu Lys Thr Pro Ser Gly
                565                 570                 575

Leu Glu His His His His His His
            580

<210> SEQ ID NO 3
<211> LENGTH: 702
<212> TYPE: PRT
<213> ORGANISM: Arabidopsis thaliana

<400> SEQUENCE: 3

Met Pro Ala Leu Ala Phe Val Asp Thr Pro Ile Asp Thr Phe Ser Ser
1               5                   10                  15
```

```
Ile Phe Thr Pro Ser Ser Val Ser Thr Ala Val Val Asp Gly Ser Cys
         20                  25                  30

His Trp Ser Pro Ser Leu Ser Ser Ser Leu Tyr Arg Ile Asp Gly Trp
         35                  40                  45

Gly Ala Pro Tyr Phe Ala Ala Asn Ser Ser Gly Asn Ile Ser Val Arg
50                   55                  60

Pro His Gly Ser Asn Thr Leu Pro His Gln Asp Ile Asp Leu Met Lys
65                   70                  75                  80

Val Val Lys Lys Val Thr Asp Pro Ser Gly Leu Gly Leu Gln Leu Pro
                 85                  90                  95

Leu Ile Val Arg Phe Pro Asp Val Leu Lys Asn Arg Leu Glu Cys Leu
                100                 105                 110

Gln Ser Ala Phe Asp Tyr Ala Ile Gln Ser Gln Gly Tyr Asp Ser His
             115                 120                 125

Tyr Gln Gly Val Tyr Pro Val Lys Cys Asn Gln Asp Arg Phe Ile Ile
130                 135                 140

Glu Asp Ile Val Glu Phe Gly Ser Gly Phe Arg Phe Gly Leu Glu Ala
145                 150                 155                 160

Gly Ser Lys Pro Glu Ile Leu Leu Ala Met Ser Cys Leu Cys Lys Gly
                165                 170                 175

Asn Pro Glu Ala Phe Leu Val Cys Asn Gly Phe Lys Asp Ser Glu Tyr
            180                 185                 190

Ile Ser Leu Ala Leu Phe Gly Arg Lys Leu Glu Leu Asn Thr Val Ile
        195                 200                 205

Val Leu Glu Gln Glu Glu Leu Asp Leu Val Ile Asp Leu Ser Gln
        210                 215                 220

Lys Met Asn Val Arg Pro Val Ile Gly Leu Arg Ala Lys Leu Arg Thr
225                 230                 235                 240

Lys His Ser Gly His Phe Gly Ser Thr Ser Gly Glu Lys Gly Lys Phe
                245                 250                 255

Gly Leu Thr Thr Val Gln Ile Leu Arg Val Val Arg Lys Leu Ser Gln
            260                 265                 270

Val Gly Met Leu Asp Cys Leu Gln Leu Leu His Phe His Ile Gly Ser
        275                 280                 285

Gln Ile Pro Ser Thr Ala Leu Leu Ser Asp Gly Val Ala Glu Ala Ala
290                 295                 300

Gln Leu Tyr Cys Glu Leu Val Arg Leu Gly Ala His Met Lys Val Ile
305                 310                 315                 320

Asp Ile Gly Gly Gly Leu Gly Ile Asp Tyr Asp Gly Ser Lys Ser Gly
                325                 330                 335

Glu Ser Asp Leu Ser Val Ala Tyr Ser Leu Glu Glu Tyr Ala Ala Ala
            340                 345                 350

Val Val Ala Ser Val Arg Phe Val Cys Asp Gln Lys Ser Val Lys His
        355                 360                 365

Pro Val Ile Cys Ser Glu Ser Gly Arg Ala Ile Val Ser His His Ser
        370                 375                 380

Val Leu Ile Phe Glu Ala Val Ser Ala Gly Gln Gln His Glu Thr Pro
385                 390                 395                 400

Thr Asp His Gln Phe Met Leu Glu Gly Tyr Ser Glu Val Arg Gly
                405                 410                 415

Asp Tyr Glu Asn Leu Tyr Gly Ala Ala Met Arg Gly Asp Arg Glu Ser
            420                 425                 430
```

Cys Leu Leu Tyr Val Asp Gln Leu Lys Gln Arg Cys Val Glu Gly Phe
            435                 440                 445

Lys Glu Gly Ser Leu Gly Ile Glu Gln Leu Ala Gly Val Asp Gly Leu
    450                 455                 460

Cys Glu Trp Val Ile Lys Ala Ile Gly Ala Ser Asp Pro Val Leu Thr
465                 470                 475                 480

Tyr His Val Asn Leu Ser Val Phe Thr Ser Ile Pro Asp Phe Trp Gly
                485                 490                 495

Ile Asp Gln Leu Phe Pro Ile Val Pro Ile His Lys Leu Asp Gln Arg
            500                 505                 510

Pro Ala Ala Arg Gly Ile Leu Ser Asp Leu Thr Cys Asp Ser Asp Gly
            515                 520                 525

Lys Ile Asn Lys Phe Ile Gly Gly Glu Ser Ser Leu Pro Leu His Glu
    530                 535                 540

Met Asp Asn Asn Gly Cys Ser Gly Gly Arg Tyr Tyr Leu Gly Met Phe
545                 550                 555                 560

Leu Gly Gly Ala Tyr Glu Glu Ala Leu Gly Gly Val His Asn Leu Phe
                565                 570                 575

Gly Gly Pro Ser Val Val Arg Val Leu Gln Ser Asp Gly Pro His Gly
            580                 585                 590

Phe Ala Val Thr Arg Ala Val Met Gly Gln Ser Ser Ala Asp Val Leu
            595                 600                 605

Arg Ala Met Gln His Glu Pro Glu Leu Met Phe Gln Thr Leu Lys His
    610                 615                 620

Arg Ala Glu Glu Pro Arg Asn Asn Asn Lys Ala Cys Gly Asp Lys
625                 630                 635                 640

Gly Asn Asp Lys Leu Val Val Ala Ser Cys Leu Ala Lys Ser Phe Asn
                645                 650                 655

Asn Met Pro Tyr Leu Ser Met Glu Thr Ser Thr Asn Ala Leu Thr Ala
            660                 665                 670

Ala Val Asn Asn Leu Gly Val Tyr Tyr Cys Asp Glu Ala Ala Ala Gly
            675                 680                 685

Gly Gly Gly Lys Gly Lys Asp Glu Asn Trp Ser Tyr Phe Gly
    690                 695                 700

<210> SEQ ID NO 4
<211> LENGTH: 2109
<212> TYPE: DNA
<213> ORGANISM: Arabidopsis thaliana

<400> SEQUENCE: 4

```
atgcctgctc tagcttttgt tgatactccc atcgatacct tttccagtat ctttacaccg      60
tcgtctgttt ccaccgccgt tgttgacggt tcctgccatt ggtctccgtc cctctcctcc     120
tctctttacc gtatcgacgg atggggagct ccgtatttcg cagcgaattc ctccgggaac     180
atctctgttc gtcctcatgg ctcaaacact ttacctcacc aagacatcga tctgatgaaa     240
gttgtgaaga aagttacaga tccgagtggt ttaggattac agcttccgct tattgttcgt     300
ttccctgatg ttctgaagaa tcgtcttgag tgtcttcaat ccgcgtttga ttacgcgatt     360
cagagtcaag gatatgattc tcattaccaa ggtgtgtatc ctgtgaaatg taatcaagat     420
cggtttatca tcgaagatat tgtcgaattc ggatccggtt tcgattcggt ttagaagct     480 ggttccaagc ctgagattct tcttgctatg agttgtttgt gtaaaggtaa tcctgaagct     540
tttcttgtgt gtaatggttt taaagactct gagtatatct cattggcttt gtttgggagg     600
```

```
aaacttgaat tgaatactgt tattgttctt gagcaagaag aagagcttga tttggttatt    660
gatttgagcc agaagatgaa tgttaggcct gttattgggt taagagctaa gcttagaact    720
aaacattctg gtcattttgg ttctacttct ggtgagaagg ggaagtttgg tttgactacg    780
gttcagattc ttcgtgtggt gaggaagctg agtcaagttg gtatgcttga ttgtctccag    840
cttctgcatt ttcacattgg ttcacagatt ccgtccacgg ctttgctttc cgacggtgtg    900
gctgaggctg cgcagcttta ctgtgagctt gtccgtcttg gtgctcatat gaaggtgatt    960
gatattggtg gtgggttggg gattgattac gacgggtcta atcggggga gtcggatctc   1020
tctgttgctt atagtctcga ggagtatgct gcagctgttg tggcttcggt taggtttgtt   1080
tgtgatcaga agtctgtgaa gcatccggtg atttgcagcg agagcggtcg agccattgtg   1140
tctcatcact cggtgttgat ctttgaagct gtctcagctg gtcaacaaca tgagacccct   1200
actgatcatc agtttatgct tgaagggtac tctgaggaag ttcgaggtga ttacgagaat   1260
ctttatggtg ctgctatgcg tggtgatcgt gaaagctgct tgctttatgt tgatcagctg   1320
aagcagagat gtgttgaagg gttcaaagaa ggttccttgg gcattgaaca gttagctggt   1380
gttgatggat tatgcgagtg ggtgattaag gcgattggtg catcggatcc ggttcttact   1440
taccatgtca atctatcggt tttcacttcg attcctgatt tctgggggat tgatcagctg   1500
tttcctattg ttccaatcca taaacttgac caaaggcctg ccgcgagagg gatcttatcg   1560
gatttgacgt gtgacagcga cggaaagatc aacaagttca taggcggaga atcgagcttg   1620
ccattgcacg agatggacaa caatggctgc agcggtgggc ggtactattt gggaatgttc   1680
ctaggtggag cttatgagga agctctcggt ggagtccaca atctgttcgg tggaccaagc   1740
gtggttcgcg tattgcagag cgatggacct cacggattcg cagtgacccg tgctgtgatg   1800
ggccaatcct ctgcagatgt cctcagagca atgcagcatg agcctgagct catgtttcag   1860
actcttaaac accgagccga ggagccgagg aacaacaaca caaagcttg tggtgataag   1920
gggaacgaca actagtagt cgcatcgtgt cttgctaagt cattcaacaa catgccttat   1980
ctttccatgg aaacgtcaac aaacgctctc accgcagcgg tcaataacct tggcgtttac   2040
tactgcgatg aagctgcagc tggtggcggc ggcaagggca agatgagaa ttggtcttat   2100
ttcggttga                                                           2109
```

<210> SEQ ID NO 5
<211> LENGTH: 208
<212> TYPE: PRT
<213> ORGANISM: Metridia pacifica

<400> SEQUENCE: 5

```
Met Met Glu Ile Lys Val Leu Phe Ala Leu Ile Cys Phe Ala Leu Val
1               5                   10                  15

Gln Ala Asn Pro Thr Glu Asn Lys Asp Asp Ile Val Gly Val Glu Gly
            20                  25                  30

Lys Phe Gly Thr Thr Asp Leu Glu Thr Asp Leu Phe Thr Ile Val Glu
        35                  40                  45

Asp Met Asn Val Ile Ser Arg Asp Thr Asn Leu Val Asn Ser Asp Ala
    50                  55                  60

Asp Arg Gly Lys Met Pro Gly Lys Lys Leu Pro Leu Glu Val Leu Ile
65                  70                  75                  80

Glu Met Glu Ala Asn Ala Arg Lys Ala Gly Cys Thr Arg Gly Cys Leu
                85                  90                  95

Ile Cys Leu Ser Lys Ile Lys Cys Thr Ala Lys Met Lys Val Tyr Ile
```

```
            100                 105                 110
Pro Gly Arg Cys His Asp Tyr Gly Gly Asp Lys Lys Thr Gly Gln Ala
            115                 120                 125

Gly Ile Val Gly Ala Ile Val Asp Ile Pro Glu Ile Ser Gly Phe Lys
            130                 135                 140

Glu Leu Gly Pro Met Glu Gln Phe Ile Ala Gln Val Asp Leu Cys Ala
145                 150                 155                 160

Asp Cys Thr Thr Gly Cys Leu Lys Gly Leu Ala Asn Val Lys Cys Ser
                165                 170                 175

Ala Leu Leu Lys Lys Trp Leu Pro Asp Arg Cys Ala Ser Phe Ala Asp
                180                 185                 190

Lys Ile Gln Ser Glu Val Asp Asn Ile Lys Gly Leu Ala Gly Asp Arg
                195                 200                 205

<210> SEQ ID NO 6
<211> LENGTH: 627
<212> TYPE: DNA
<213> ORGANISM: Metridia pacifica

<400> SEQUENCE: 6
atgatggaaa tcaaagttct gtttgccctg atttgttttg cactggttca ggcaaatccg      60
accgaaaaca agatgatat tgttggtgtg gaaggcaaat ttggcaccac cgatctggaa      120
accgacctgt ttaccattgt tgaagatatg aatgtgatca gccgtgatac caatctggtt      180
aatagtgatg cagatcgtgg taaaatgcct ggtaaaaaac tgccgctgga agttctgatt      240
gaaatggaag caaatgcacg taaagcaggt tgtacccgtg ttgtctgat ttgtctgagc      300 aaaatcaaat gtaccgccaa atgaaagtg tatattccgg tcgttgtca tgattatggt      360 ggtgacaaaa aaccggtca ggcaggtatt gtgggtgcaa ttgttgatat tccggaaatt      420
agcggcttta agaactggg tccgatggaa cagtttattg cacaggttga tctgtgtgca      480
gattgtacca ccggttgcct gaaaggtctg gcaaatgtta atgtagcgc actgctgaaa      540 aaatggctgc cggatcgttg tgccagcttt gcagataaaa ttcagagcga agtggataac      600
attaaaggcc tggcaggcga tcgttaa                                          627

<210> SEQ ID NO 7
<211> LENGTH: 394
<212> TYPE: PRT
<213> ORGANISM: Drosophila melanogaster

<400> SEQUENCE: 7

Met Ala Ala Ala Thr Pro Glu Ile Gln Phe Tyr Glu Arg Glu Leu Asn
1               5                   10                  15

Ile Arg Arg Val Ile Glu Glu Cys Asp Leu Gln Arg Leu Asp Gln Ala
                20                  25                  30

Leu Asn Ile Cys Asp Leu Ser Ser Val Glu Arg Lys Leu Arg Leu Trp
            35                  40                  45

Gln Lys Leu Leu Pro Arg Ile Lys Pro Phe Tyr Ala Val Lys Cys Asn
        50                  55                  60

Asp Asp Pro Met Val Val Arg Leu Leu Ala Gln Leu Gly Ala Gly Phe
65                  70                  75                  80

Asp Cys Ala Ser Lys Asn Glu Val Lys Leu Val Leu Gly Phe Asp Val
                85                  90                  95

Ser Pro Glu Arg Ile Ile Phe Ala Asn Pro Cys Arg Pro Val Ser His
            100                 105                 110
```

Leu Glu Tyr Ala Lys Glu His Gln Val Ser Asn Gly Thr Val Asp Asn
            115                 120                 125

Glu Phe Glu Val Tyr Lys Leu His Thr His Tyr Pro Asn Ser Asn Leu
        130                 135                 140

Ile Val Arg Phe Lys Ser Glu Ala Lys Glu Ala Gln Cys Pro Leu Gly
145                 150                 155                 160

Asp Lys Phe Gly Cys Asp Ala Asp Val Asp Ala Ala Leu Met Leu
                165                 170                 175

Leu Ala Lys Ser Leu Glu Leu Lys Val Thr Gly Thr Ser Phe His Val
            180                 185                 190

Gly Ser Gly Cys Ser Glu Leu Gln Ala Tyr Asp Arg Ala Ile Lys Lys
        195                 200                 205

Ala Lys Asn Leu Phe Lys Phe Gly Ala Leu Leu Gly Tyr Asp Met Asp
210                 215                 220

Phe Leu Asp Ile Gly Gly Gly Phe Pro Gly Ser Asp Asp Val Lys Phe
225                 230                 235                 240

Glu Lys Ile Ala Glu Ser Val Asn Thr Ser Val Gln Arg His Phe Pro
            245                 250                 255

Asp Glu Arg Val His Ile Ile Ala Glu Pro Gly Arg Phe Phe Val Ala
        260                 265                 270

Ala Ala Cys Thr Leu Val Cys Lys Ile His Ala Lys Arg Glu Ile Arg
    275                 280                 285

Asn Glu Ala Gly Lys Leu Asp Thr Val Met Tyr Tyr Leu Asn Asp Gly
290                 295                 300

Val Tyr Gly Ser Phe Asn Cys Ile Leu Tyr Asp His Gln Val Val Ile
305                 310                 315                 320

Ala Glu His Tyr Leu Asp Asn Ala Glu Ser Leu Pro His Leu Lys Ser
            325                 330                 335

Leu Ile Trp Gly Pro Ser Cys Asp Ala Leu Asp Lys Ile Ser Glu Asp
        340                 345                 350

Leu His Leu Pro Asn Leu Asn Arg Gly Asp Leu Leu Gly Phe Arg Asn
    355                 360                 365

Met Gly Ala Tyr Thr Met Pro Ile Ala Ser Ala Phe Asn Gly Phe Glu
370                 375                 380

Val Pro Lys Thr Leu Tyr Phe Gln Ala Ile
385                 390

<210> SEQ ID NO 8
<211> LENGTH: 1185
<212> TYPE: DNA
<213> ORGANISM: Drosophila melanogaster

<400> SEQUENCE: 8
atggcggccg ctaccctga aatccagttc tacgaacgcg agctcaacat ccgccgggtg      60
atcgaggagt gcgacctgca gcgcctggac caggccctca acatctgcga cctgtctagc     120
gtggagcgta agctgcgcct ctggcagaag ctcctgccca ggatcaagcc cttctacgcc     180
gtcaagtgca tgacgatcc aatggtggtc aggctgctgg cccagctggg agccggattc     240
gactgcgcct ccaaaaacga agtcaagctg gtcttgggct tcgatgtctc gccggagcgt     300
atcatcttcg ccaatccctg ccgccctgtc agccatctgg agtacgccaa ggagcaccag     360
gtgtccaacg gaacggtgga caatgagttc gaggtataca agctgcacac gcactatccc     420
aactccaacc tgatcgtgag attcaagagc gaggccaagg aggcacagtg cccactgggc     480
gacaaatttg gctgtgatgc ggatgtggat gcagcggccc taatgctgct ggccaaatcc     540

```
ttggagctga aggtgaccgg caccagtttc acgtcggct  ccggatgcag cgagctgcag   600
gcctacgatc gggccatcaa gaaggccaag aacctcttca agttcggcgc actactgggc   660
tatgacatgg actttctgga cattggcggt gggttccctg gcagcgatga cgtaaagttt   720
gagaagatag ccgaaagtgt gaatacctcg gtgcagcgtc attttcccga cgaacgcgtt   780
cacataatcg ccgaaccagg acgcttcttt gtggcggcag cctgcacctt ggtttgcaag   840
atccacgcca gcggggagat caggaacgaa gctggcaaac tggacaccgt aatgtactat   900
ctgaatgacg gcgtctatgg gtccttcaac tgcattctgt acgaccatca agtggtgatt   960
gcagagcatt atctggacaa tgcagaatct ttgccacacc taaagtcctt gatttggggg  1020
ccaagttgtg acgccctaga taagatttcg gaggacctgc acttgcccaa cctaaaccga  1080
ggcgatcttt tgggattccg aaacatgggc gcctacacca tgcccattgc cagtgcattc  1140
aatggattcg aagtccccaa gaccctgtac ttccaagcta tatga               1185
```

<210> SEQ ID NO 9
<211> LENGTH: 535
<212> TYPE: PRT
<213> ORGANISM: Drosophila melanogaster

<400> SEQUENCE: 9

```
Met Leu Arg Tyr Thr Ala Arg Ile Leu Asn Gly Ile Tyr Pro Leu Met
1               5                   10                  15

Pro Arg Gln Val Leu Lys Arg Ser Ala His Gln Val Pro Glu Lys Leu
            20                  25                  30

Lys Lys Val Glu Thr Asp Lys Asp Pro Glu Phe Ser Glu Met Val Leu
        35                  40                  45

Tyr Tyr Tyr His Lys Ala Ala Gln Thr Met Glu Pro Ala Leu Leu Lys
    50                  55                  60

Glu Met Glu Lys Tyr Pro His Met Lys Pro Glu Glu Arg Gln Ala Arg
65                  70                  75                  80

Val Thr Ala Ile Leu Asn Leu Leu Gly Ser Val Ser Thr Ser Val Glu
                85                  90                  95

Val Asn Phe Pro Ile Val Arg Lys Asn Gly Thr Tyr Glu Ile Ile Ser
            100                 105                 110

Gly Tyr Arg Ser His His Val Arg His Arg Leu Pro Leu Lys Gly Gly
        115                 120                 125

Ile Arg Tyr Ala Leu Asp Val Asn Glu Ser Glu Val Lys Ala Leu Ala
    130                 135                 140

Ala Ile Met Thr Phe Lys Cys Ala Cys Val Asn Val Pro Tyr Gly Gly
145                 150                 155                 160

Ser Lys Gly Gly Ile Cys Ile Asp Pro Lys Lys Tyr Thr Val Asp Glu
                165                 170                 175

Leu Gln Thr Ile Thr Arg Arg Tyr Thr Met Glu Leu Leu Lys Arg Asn
            180                 185                 190

Met Ile Gly Pro Gly Ile Asp Val Pro Ala Pro Asp Val Asn Thr Gly
        195                 200                 205

Pro Arg Glu Met Ser Trp Ile Val Asp Gln Tyr Gln Lys Thr Phe Gly
    210                 215                 220

Tyr Lys Asp Ile Asn Ser Ser Ala Ile Val Thr Gly Lys Pro Val His
225                 230                 235                 240

Asn Gly Gly Ile Asn Gly Arg His Ser Ala Thr Gly Arg Gly Val Trp
                245                 250                 255
```

```
Lys Ala Gly Asp Leu Phe Leu Lys Asp Lys Glu Trp Met Asp Leu Leu
                260                 265                 270

Lys Trp Lys Thr Gly Trp Lys Asp Lys Thr Val Ile Val Gln Gly Phe
            275                 280                 285

Gly Asn Val Gly Ser Phe Ala Ala Lys Tyr Val His Glu Ala Gly Ala
        290                 295                 300

Lys Val Ile Gly Ile Lys Glu Phe Asp Val Ser Leu Val Asn Lys Asp
305                 310                 315                 320

Gly Ile Asp Ile Asn Asp Leu Phe Glu Tyr Thr Glu Lys Lys Thr
                325                 330                 335

Ile Lys Gly Tyr Pro Lys Ala Gln Glu Ser Lys Glu Asp Leu Leu Val
            340                 345                 350

Ala Glu Thr Asp Ile Leu Met Pro Cys Ala Thr Gln Lys Val Ile Thr
        355                 360                 365

Thr Asp Asn Ala Lys Asp Ile Lys Ala Lys Leu Ile Leu Glu Gly Ala
    370                 375                 380

Asn Gly Pro Thr Thr Pro Ser Gly Glu Lys Ile Leu Leu Asp Lys Gly
385                 390                 395                 400

Val Leu Leu Val Pro Asp Leu Tyr Cys Asn Ala Gly Gly Val Thr Val
                405                 410                 415

Ser Tyr Phe Glu Tyr Leu Lys Asn Ile Asn His Val Ser Tyr Gly Lys
            420                 425                 430

Met Asn Ser Lys Ser Thr Ser Glu Leu Ile Ile Glu Leu Met Asn Ser
        435                 440                 445

Ile Asn Glu Ser Leu His Glu Cys Pro Asp Ser Gln Leu Pro Asn Ile
    450                 455                 460

Cys Pro Asn Lys Lys Leu Lys Arg Ile Gln Gln Cys Thr Thr Glu Ala
465                 470                 475                 480

Asp Ile Val Asp Ser Ala Leu Gln Thr Val Met Glu Ser Ala Ala Arg
                485                 490                 495

Gly Ile Lys Glu Met Ala His Lys Phe Glu Leu Cys Asn Asp Leu Arg
            500                 505                 510

Arg Ala Ala Tyr Val Trp Ser Ser Phe Lys Ile Phe Gln Ala Met Glu
        515                 520                 525

Ser Ser Gly Ile Ser Gln Gln
    530                 535

<210> SEQ ID NO 10
<211> LENGTH: 1608
<212> TYPE: DNA
<213> ORGANISM: Drosophila melanogaster

<400> SEQUENCE: 10
atgcttcgtt atacggcacg gattttgaat gggatttacc cacttatgcc aaggcaagta      60
ttaaaacgtt ccgcacacca ggtgcccgag aagctgaaaa agttgagac ggacaaggac      120 ccggaattct cggaaatggt tctttattat tatcacaagg ccgcgcagac tatggagcct      180
gcattgctca aggaaatgga aaagtatccg catatgaagc cggaggagcg tcaggctcgt      240
gtcaccgcta tactgaatct gcttgggagc gtctccacct cggtggaggt taattttccc      300
attgtccgca aaaacggcac ctacgagatc atcagcggtt atcgttcgca tcatgtacgc      360
catcgattgc ctctcaaggg cggaatccga tacgctctgg acgtgaacga gagcgaagtt      420
aaagcccttg ccgccattat gacgttcaag tgcgcttgcg tgaatgtacc ttatggtgga      480
tctaagggcg gcatttgtat cgatcccaag aagtatacag tggatgagct gcagacgatc      540
```

```
acacggcgat acacgatgga gttgctcaag cgtaatatga ttggtcccgg catcgatgta      600
ccggcgcccg atgtgaacac tggtccgcgt gagatgagct ggattgttga tcagtaccag      660
aagacatttg gctacaagga tatcaattca tcggctattg tcaccgggaa gcccgtacac      720
aacggcggca ttaatggtcg acattcggcc acgggcagag gcgtttggaa ggcgggcgat      780
ctctttctga aggataagga atggatggat ctgctcaagt ggaagacggg atggaaggac      840
aagacggtca tagtgcaggg atttggcaat gtgggctcct tgccgctaa gtatgtgcac       900 gaggcgggcg ccaaagtcat cggaataaaa gagtttgatg tttctctggt taataaggac      960
ggcatagata ttaatgatct ttttgaatac actgaggaaa agaagactat aaaggatat     1020 ccaaaagctc aggagtctaa ggaggacttg ttggtagccg aaaccgatat ccttatgccg     1080
tgtgccaccc aaaaagtgat aaccaccgac aatgccaaag acatcaaggc caagctgatc     1140
ctggaaggcg ccaacgggcc gaccacacca tctggcgaga aaatcctatt ggataagggt     1200
gtcctcctag ttcccgatct ctattgcaat gcgggcggcg taacagtatc ctactttgag     1260
tacctcaaaa acattaacca cgtgtcatat ggcaaaatga actctaaatc tacatccgag     1320
cttattatcg aactgatgaa ctccatcaat gagtctttgc atgaatgccc cgatagtcaa     1380
ctaccgaaca tatgtcccaa taagaaactt aagaggatac aacaatgcac cacagaggcg     1440
gatatcgtgg actcggctct ccaaacagtt atggaatctg cagcacgtgg catcaaggag     1500
atggcccaca atttgaatt gtgtaacgat ctgcggaggg ccgcctacgt ttggtcttca     1560
ttcaaaattt tccaagccat ggaaagctcc ggaatttccc aacagtag               1608
```

```
<210> SEQ ID NO 11
<211> LENGTH: 192
<212> TYPE: PRT
<213> ORGANISM: Artificial sequence
<220> FEATURE:
<223> OTHER INFORMATION: Human Growth Hormon

<400> SEQUENCE: 11

Met Phe Pro Thr Ile Pro Leu Ser Arg Leu Phe Asp Asn Ala Met Leu
1               5                   10                  15

Arg Ala His Arg Leu His Gln Leu Ala Phe Asp Thr Tyr Gln Glu Phe
            20                  25                  30

Glu Glu Ala Tyr Ile Pro Lys Glu Gln Lys Tyr Ser Phe Leu Gln Asn
        35                  40                  45

Pro Gln Thr Ser Leu Cys Phe Ser Glu Ser Ile Pro Thr Pro Ser Asn
    50                  55                  60

Arg Glu Glu Thr Gln Gln Lys Ser Asn Leu Glu Leu Leu Arg Ile Ser
65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
        115                 120                 125

Leu Glu Asp Gly Ser Pro Arg Thr Gly Gln Ile Phe Lys Gln Thr Tyr
    130                 135                 140

Ser Lys Phe Asp Thr Asn Ser His Asn Asp Ala Leu Leu Lys Asn
145                 150                 155                 160

Tyr Gly Leu Leu Tyr Cys Phe Arg Lys Asp Met Asp Lys Val Glu Thr
                165                 170                 175
```

```
Phe Leu Arg Ile Val Gln Cys Arg Ser Val Glu Gly Ser Cys Gly Phe
            180                 185                 190
```

METHOD OF PRODUCING AN ACTIVE-FORM MUTANT ENZYME

TECHNICAL FIELD

The present invention relates to a method for producing an active-form mutant enzyme and a novel active-form mutant enzyme and a method for producing a soluble mutant protein. More specifically, the present invention relates to a method for obtaining an active-form mutant enzyme by mutagenesis to an enzyme that is expressed in a heterologous expression system as an inactive-form enzyme, the method including selecting an effective mutation site and an amino acid after mutation, and relates to a novel active-form mutant enzyme obtained by the method. The present invention further relates to a method for obtaining a soluble mutant protein by mutagenesis to a protein that is expressed in a heterologous expression system as an insoluble-form protein, the method including selecting an effective mutation site and an amino acid after mutation.

CROSS-REFERENCE TO RELATED APPLICATIONS

The present application claims priority to Japanese Patent Application No. 2015-117808 filed on 10 Jun. 2015, which is entirely incorporated herein by reference.

BACKGROUND ART

There are many cases when an enzyme protein gene is expressed in a heterologous expression system, the protein is not expressed as an active-form enzyme and this is the biggest problem in a large-scale expression of enzyme protein by a heterologous host. In order to solve the problem, various approaches have been taken. For example, in order to express an active-form enzyme in a host *Escherichia coli*, cell culture conditions are examined (PTL 1), and the following methods are mentioned: methods in which proteins are co-expressed with molecular chaperones which allow formation of correct conformation (PTL 2), methods in which proteins are expressed as fusion proteins with signal peptides or tags that improve solubility (PTL 3 and PTL 4) and methods in which proteins which form inclusion bodies are unfolded with a denaturing agent and the like and refolded into correct conformation (PTL 5, PTL 6 and PTL 7). In addition, methods in which, without using *E. coli*, enzyme genes having the same amino acid sequences as the wild type are expressed in yeast, insect or animal cultured cells (NPL 1 and NPL 2) and cell-free translation systems in which entire transcription to translation of genes is carried out in vivo (PTL 8) have also been developed.

However, there are many proteins for which inclusion bodies are not eliminated by co-expression with chaperone genes and other methods also have issues such as complicated procedures and high cost. Therefore, there is still a need for a new technique which allows expression of an enzyme gene as an active-form enzyme by the simplest and the most cost effective way.

Until now, a reported example of expression of a heterologous enzyme in *E. coli* as an active-form mutant enzyme is expression of a soluble protein from a plant-derived hydroxynitrile lyase gene containing random mutations (PTL 9). There is also a report on a method in which a gene sequence of a target protein is subjected to random mutation followed by the addition of a reporter protein so as to select a sequence that is expressed as an active-form mutant enzyme (NPL 3). However, there is no report on a method that allows specifying a mutation site of a gene or a mutated amino acid that allows expression of a protein as an active-form mutant enzyme.

When genes of various proteins including enzymes are expressed in heterologous expression systems, the proteins are not always expressed as soluble proteins. This is a problem in a large-scale expression of various proteins by a heterologous host. In order to solve the problem, there have been known co-expression with molecular chaperone proteins (NPL 4), expression as fusion proteins with maltose-binding proteins (NPL 5) and the like.

CITATION LIST

Patent Literature

[PTL 1] Japanese Patent Application Laid-open No. 2012-44888
[PTL 2] Japanese Patent Application Laid-open No. H11-9274
[PTL 3] Japanese Patent Application Laid-open No. 2012-116816
[PTL 4] Japanese Patent Application Laid-open No. 2012-179062
[PTL 5] Japanese Patent Application Laid-open No. H11-335392
[PTL 6] Japanese Patent Application Laid-open No. 2011-46686
[PTL 7] Japanese Translation of PCT Application No. 2001-503614
[PTL 8] Japanese Patent Application Laid-open No. 2004-105070
[PTL 9] WO 2006/041226

Non Patent Literature

[NPL 1] Meth. In Molecular Biol., Protocols 103 (1998)
[NPL 2] J. Biol. Chem., 264, pp. 8222-8229 (1989)
[NPL 3] Microb. Cell Fact., 4, pp. 1-8 (2005)
[NPL 4] Appl. Environ. Micorobiol., 64, pp. 1694-1699 (1998)
[NPL 5] Protein science, 8, pp. 1669-1674 (1999)
[NPL 6] J. Mol. Biol., 157, pp. 105-132 (1982)
[NPL 7] Sci. Rep., 5 doi: 10.1038/srep08193 (2015)

SUMMARY OF INVENTION

Technical Problem

As described above, co-expression with chaperone genes and use of yeast and animal cells, for example, have been developed as method for expressing active-form mutant enzymes of proteins which are otherwise expressed as inactive-form enzymes in heterologous expression systems. However, the developed methods have such problems that procedures are complicated or the methods are expensive. In addition, only limited types of enzymes could be soluble by applying the methods and thus it is difficult to widely apply the methods to enzymes for industrial applications. Although some enzymes are reported to be expressed as active-form mutant enzymes by mutagenesis, there has been no known method that allows effective identification of a gene mutation site or a mutated amino acid that is efficacious for expressing a wide range of enzymes as active-form mutant enzymes. Similar to inactive-form enzymes, there has been no known method that allows effective identification of a gene mutation site or a mutated amino acid that is efficacious for expressing a soluble form of a protein which is otherwise expressed as an insoluble protein in a heterologous expression system.

Thus, an object of the present invention is to provide a method for expressing an enzyme as an active-form mutant enzyme, the enzyme being not expressed as an active-form enzyme or expressed as an active enzyme at a minute amount in a heterologous expression system, including selecting an effective mutation site and an amino acid after mutation. Another object of the present invention is to provide a novel active-form mutant enzyme obtained by the method.

Another object of the present invention is to provide a method for expressing a protein as a soluble mutant protein, the protein being not expressed as a soluble protein or expressed as a soluble protein at a minute amount in a heterologous expression system, including selecting an effective mutation site and an amino acid after mutation.

Solution to Problem

In order to achieve the above objects, the inventors of the present invention investigated the relationship between mutation sites of enzyme genes and expression of active-form mutant enzyme genes in heterologous expression systems and found that (1) an active-form mutant enzyme can be expressed by substituting a hydrophobic amino acid that is present in a hydrophilic domain of an α-helix structural region of an enzyme protein to a certain hydrophilic amino acid or by substituting a hydrophilic amino acid that is present in a hydrophobic domain of the region to a certain hydrophobic amino acid and/or (2) an active-form mutant enzyme can be expressed by obtaining an amino acid sequence in which at least one amino acid with relatively low conservation to an amino acid with higher conservation than said amino acid, and (3) the methods described above are versatile methods for preparing an active-form mutant enzyme which can be applied to various wild type enzymes that are inactive in heterologous expression systems. The inventors of the present invention thus completed the present invention.

The inventors of the present invention introduced mutations to enzyme genes derived from microorganisms, plants and animals which, in heterologous expression systems such as *E. coli*, are not expressed as active enzymes or, even if expressed, the expression level of which is low, and then investigated by combining determination of protein expression by electrophoresis and activity assay of the target enzyme. The inventors of the present invention thereby found that the mutations sites in proteins exhibiting activities are "a hydrophilic amino acid that is present in a hydrophobic domain or a hydrophobic amino acid that is present in a hydrophilic domain". The inventors of the present invention then analysed the mutation sites in detail on a secondary structure predicting programme and revealed that the mutation sites may be in "an α-helix region of an enzyme protein". The inventors of the present invention further revealed that expression of active-form mutant enzymes has a common feature of "mutation of a hydrophilic amino acid that is present in a hydrophobic domain of an α-helix that is present in an enzyme protein or a hydrophobic amino acid that is present in a hydrophilic domain". The inventors of the present invention also analysed in detail by dividing α-helix regions obtained by secondary structure prediction into a hydrophilic domain and a hydrophobic domain by Edmundson wheel plot and found that a mutant enzyme exhibiting activity may be obtained by substituting a hydrophilic amino acid that is present in a hydrophobic domain to a hydrophobic amino acid or by substituting a hydrophobic amino acid that is present in a hydrophilic domain to a hydrophilic amino acid and that there is certain relationship between the mutation site of an amino acid (gene) and expression of an active-form mutant enzyme.

Although the above technique is to express an active-form mutant enzyme gene only by focusing the amino acid sequence of the target protein, the inventors of the present invention found that when, separate from the above, amino acid sequences similar to that of the target protein are known, it is possible to obtain an active-form mutant protein with high probability and thus efficiently prepare an active-form mutant enzyme by focusing the conservation in the sequence identity of the similar amino acid sequences and substituting an amino acid having low conservation to an amino acid having relatively high conservation.

Although the above technique utilizes the conservation in the sequence identity of similar amino acid sequences, the inventors of the present invention further revealed that the technique may be further applied to a candidate amino acid to be mutated in an α-helix region of an enzyme protein to more efficiently prepare an active-form mutant enzyme.

The inventors of the present invention also revealed that the above technique may be applied not only for preparation of an active-form mutant enzyme but also for obtaining a soluble mutant protein of which native form is expressed as an insoluble protein in a heterologous expression system.

The present invention is as follows:

[1]

A method for producing an active-form mutant enzyme comprising:
expressing, in a heterologous expression system, a gene having a base sequence that codes for an amino acid sequence in which: at least one hydrophobic amino acid that is present in a hydrophilic domain of an α-helix structure region is substituted (to an amino acid with higher hydrophilicity or lower hydrophobicity than the amino acid to be substituted) and/or at least one hydrophilic amino acid that is present in a hydrophobic domain of the α-helix structure region is substituted (to an amino acid with higher hydrophobicity or lower hydrophilicity than the amino acid to be substituted),
wherein the α-helix structure region is in an amino acid sequence of a protein of which native form exhibits an enzyme activity but which exhibits no enzyme activity or a feeble enzyme activity when expressing a gene of the protein in a heterologous expression system (hereinafter "an inactive-form enzyme); and selecting a protein (hereinafter "an active-form mutant enzyme") that exhibits the same sort of enzyme activity as that obtained in the native form.

[2]

The producing method according to [1], wherein the method includes:
(1) specifying a protein of which native form exhibits an enzyme activity but which exhibits no enzyme activity or a feeble enzyme activity when expressing a gene of the protein in a heterologous expression system (hereinafter "an inactive-form enzyme");
(2a) specifying an α-helix structure region of the inactive-form enzyme specified in step (1), specifying a hydrophilic domain and/or hydrophobic domain of the specified α-helix structure region, and specifying a hydrophobic amino acid that is present in the hydrophilic domain and/or a hydrophilic amino acid that is present in the hydrophobic domain;

(3a) preparing a gene having a base sequence that codes for an amino acid sequence in which at least one hydrophobic amino acid that is present in the hydrophilic domain of the α-helix structure region in the amino acid sequence of the inactive-form enzyme is substituted (to an amino acid with higher hydrophilicity or lower hydrophobicity than the amino acid to be substituted) and/or at least one hydrophilic amino acid that is present in the hydrophobic domain of the α-helix structure region is substituted (to an amino acid with higher hydrophobicity or lower hydrophilicity than the amino acid to be substituted); and (4a) expressing, in a heterologous expression system, the gene having the base sequence prepared in step (3a) to obtain a protein and selecting from the obtained proteins, a protein (hereinafter "an active-form mutant enzyme") that exhibits the same sort of enzyme activity as that obtained in the native form.

[3]

A method for producing a soluble mutant protein comprising:
expressing, in a heterologous expression system, a gene having a base sequence that codes for an amino acid sequence in which:
at least one hydrophobic amino acid that is present in a hydrophilic domain of an α-helix structure region is substituted (to an amino acid with higher hydrophilicity or lower hydrophobicity than the amino acid to be substituted) and/or at least one hydrophilic amino acid that is present in a hydrophobic domain of the α-helix structure region is substituted (to an amino acid with higher hydrophobicity or lower hydrophilicity than the amino acid to be substituted), wherein the α-helix structure region is in an amino acid sequence of a protein of which native form is a soluble protein but which becomes insoluble when expressing a gene of the protein in a heterologous expression system (hereinafter "an insoluble-form protein); and
selecting a protein (hereinafter "a soluble mutant protein") that is soluble.

[4]

The producing method according to [3], wherein the method includes:
(1) specifying a protein of which native form is a soluble protein but which becomes insoluble when expressing a gene of the protein in a heterologous expression system (hereinafter "an insoluble-form protein");
(2a) specifying an α-helix structure region of the insoluble-form protein specified in step (1), specifying a hydrophilic domain and/or hydrophobic domain of the specified α-helix structure region, and specifying a hydrophobic amino acid that is present in the hydrophilic domain and/or a hydrophilic amino acid that is present in the hydrophobic domain;
(3a) preparing a gene having a base sequence that codes for an amino acid sequence in which at least one hydrophobic amino acid that is present in the hydrophilic domain of the α-helix structure region in the amino acid sequence of the insoluble-form protein is substituted (to an amino acid with higher hydrophilicity or lower hydrophobicity than the amino acid to be substituted) and/or at least one hydrophilic amino acid that is present in the hydrophobic domain of the α-helix structure region is substituted (to an amino acid with higher hydrophobicity or lower hydrophilicity than the amino acid to be substituted); and
(4a) expressing, in a heterologous expression system, the gene having the base sequence prepared in step (3a) to obtain a protein and selecting from the obtained proteins, a protein (hereinafter "a soluble mutant protein") that is soluble.

[5]

The producing method according to [3] or [4], wherein being the soluble mutant protein is judged from an amount of soluble protein in an extract after heterologous expression.

[6]

The producing method according to [5], wherein the soluble mutant protein is defined as a mutant protein of which amount of the soluble protein in the extract after heterologous expression is higher than an amount of the soluble protein in an extract after heterologous expression of the native form protein.

[7]

The producing method according to [2] or [4], wherein in the step (2a) the hydrophilic domain and/or hydrophobic domain is specified by drawing a helical wheel of the α-helix structure region by using a secondary structure predicting method, aligning amino acids at positions 1, 5, 2, 6, 3, 7 and 4 on the helical wheel in this order to form a sequence and repeating the procedure to form at least two amino acid sequences each of which has 7 amino acids (it is sufficient that the second sequence has 5 or more amino acids);
in the amino acid sequence region where at least two sequences are aligned, defining a row in which the sum of the hydropathy index of the amino acids therein is 0 or more as a hydrophobic row and defining a row in which the sum of the hydropathy index of the amino acids therein is less than 0 as a hydrophilic row; and defining a bunch of 3 or 4 consecutive hydrophobic rows as the hydrophobic domain and defining a bunch of 4 or 3 consecutive hydrophilic rows as the hydrophilic domain (provided that the sum of the hydropathy index of any one row that is internal to 4 hydrophobic rows in the hydrophobic domain may be less than 0 and the sum of the hydropathy index of any one row that is internal to 4 hydrophilic rows in the hydrophilic domain may be 0 or more).

[8]

The producing method according to [2], [4] or [7], wherein in step (2a), an amino acid among amino acids in the hydrophilic domain, having the hydropathy index of 0 or more is specified as a hydrophobic amino acid and an amino acid, among amino acids in the hydrophobic domain, having the hydropathy index of less than 0 is specified as a hydrophilic amino acid.

[9]

The producing method according to any one of [2], [4], [7] and [8], wherein in the step (3a), the hydrophobic amino acid that is present in the hydrophilic domain is substituted to an amino acid with lower hydropathy index than the amino acid to be substituted, and the hydrophilic amino acid that is present in the hydrophobic domain is substituted to an amino acid with higher hydropathy index than the amino acid to be substituted.

[10]

The producing method according to [2], [4] or [7], wherein in step (3a), the hydrophobic amino acid that is present in the hydrophilic domain is substituted to an amino acid with lower hydropathy index than the amino acid to be substituted and with a hydropathy index of less than 0, and the hydrophilic amino acid that is present in the hydrophobic domain is substituted to an amino acid with higher hydropathy index than the amino acid to be substituted and with a hydropathy index of 0 or more.

[11]

The producing method according to any one of [2], [4] and [7] to [10], wherein in step (3a), the amino acid is substituted to an amino acid with higher conservation in sequence identity than the amino acid to be substituted.

[12]

The producing method according to any one of [2], [4] and [7] to [11], wherein in the step (3a), the amino acid substitution is carried out for any of a plurality of amino acids and in step (4a), the active-form mutant enzyme or the soluble mutant protein is selected from a plurality of proteins in which any of the amino acids are substituted.

[13]

A method for producing an active-form mutant enzyme, comprising expressing, in a heterologous expression system, a gene having a base sequence that codes for an amino acid sequence of a protein of which native form exhibits an enzyme activity but which exhibits no enzyme activity or a feeble enzyme activity when expressing a gene of the protein in a heterologous expression system (hereinafter "an inactive-form enzyme"), wherein in the amino acid sequence, at least one amino acid with relatively low conservation is substituted to an amino acid with higher conservation than said amino acid; and obtaining a protein (hereinafter "an active-form mutant enzyme") that exhibits the same sort of enzyme activity as that obtained in the native form.

[14]

The producing method according to [13], comprising:
(1) specifying a protein of which native form exhibits an enzyme activity but which exhibits no enzyme activity or a feeble enzyme activity when expressing a gene of the protein in a heterologous expression system (hereinafter "an inactive-form enzyme");
(2b) determining a conservation in sequence identity of at least some amino acids in an amino acid sequence of the inactive-form enzyme specified in step (1) and specifying an amino acid with relatively low conservation;
(3b) preparing a gene having a base sequence that codes for an amino acid sequence in which at least one amino acid with relatively low conservation is substituted to an amino acid with higher conservation than said amino acid; and
(4b) expressing, in a heterologous expression system, the gene having the base sequence prepared in step (3b) to obtain a protein and selecting from the obtained proteins, a protein (hereinafter "an active-form mutant enzyme") that exhibits the same sort of activity as that obtained in the native form.

[15]

A method for producing a soluble mutant protein, comprising expressing, in a heterologous expression system, a gene having a base sequence that codes for an amino acid sequence of a protein of which native form is a soluble protein but which becomes insoluble when expressing a gene of the protein in a heterologous expression system (hereinafter "an insoluble-form protein"), wherein in the amino acid sequence, at least one amino acid with relatively low conservation is substituted to an amino acid with higher conservation than said amino acid; and obtaining a protein (hereinafter "a soluble mutant protein") that is soluble.

[16]

The producing method according to [15], comprising:
(1) specifying a protein of which native form is a soluble protein but which becomes insoluble when expressing a gene of the protein in a heterologous expression system (hereinafter "an insoluble-form protein");
(2b) determining a conservation in sequence identity of at least some amino acids in an amino acid sequence of the insoluble-form protein specified in step (1) and specifying an amino acid with relatively low conservation;
(3b) preparing a gene having a base sequence that codes for an amino acid sequence in which at least one amino acid with relatively low conservation is substituted to an amino acid with higher conservation than said amino acid; and
(4b) expressing, in a heterologous expression system, the gene having the base sequence prepared in step (3b) to obtain a protein and selecting from the obtained proteins, a soluble mutant protein.

[17]

The producing method according to [15] or [16], wherein being the soluble mutant protein is judged from an amount of the soluble protein in an extract after heterologous expression.

[18]

The producing method according to [17], wherein the soluble mutant protein is defined as a mutant protein of which amount of the soluble protein in the extract after heterologous expression is higher than an amount of soluble protein in an extract after heterologous expression of the native form protein.

[19]

The producing method according to [14] or [16], wherein the amino acid sequence for which the conservation in sequence identity is determined in step (2b) is selected from an amino acid sequence of an α-helix structure region of the inactive-form enzyme or the insoluble-form protein specified in step (1).

[20]

The producing method according to [14], [16] or [19], wherein the substituting amino acid is any one of three amino acids with the highest conservation in sequence identity.

[21]

The producing method according to any one of [14], [16], [19] and [20], wherein in step (3b), the amino acid substitution is carried out for a plurality of amino acids and in the step (4b), the active-form mutant enzyme or the soluble mutant protein is selected from proteins in which a plurality of amino acids are substituted.

[22]

The producing method according to any one of [1] to [21], wherein the heterologous expression system is an *Escherichia coli* expression system, a yeast expression system, a *Brevibacillus* expression system, a *Corynebacterium* expression system, an *Aspergillus* expression system, an insect cell expression system, an *Actinomyces* expression system, a plant cell expression system, an animal cell expression system or a cell-free protein synthetic system.

[23]

The producing method according to any one of [1] to [22], wherein the active-form mutant enzyme has an enzyme activity value in the range of 2 times to infinity of the inactive-form enzyme.

[24]

An active-form mutant mandelonitrile oxidase having an amino acid sequence shown in SEQ ID NO: 2, wherein: valine at the position 444 has been substituted to threonine, serine, tyrosine, histidine, glutamic acid, glutamine, aspartic acid, asparagine, lysine or arginine and/or valine at the position 455 has been substituted to glutamic acid, glutamine, aspartic acid, asparagine, lysine or arginine.

[25]

An active-form mutant arginine decarboxylase having an amino acid sequence shown in SEQ ID NO: 3, wherein: valine at the position 261 has been substituted to threonine, serine, glutamic acid, aspartic acid, asparagine, lysine or arginine and/or arginine at the position 430 has been substituted to valine, leucine or alanine, and
leucine at the position 435 has been substituted to histidine, glutamic acid, glutamine, aspartic acid, asparagine or lysine.

[26]

An active-form mutant ornithine decarboxylase having an amino acid sequence shown in SEQ ID NO: 7, wherein:
lysine at the position 117 has been substituted to leucine and/or
leucine at the position 176 has been substituted to glutamic acid.

[27]

An active-form mutant luciferase having an amino acid sequence shown in SEQ ID NO: 5, wherein:
isoleucine at the position 80 has been substituted to lysine and/or
alanine at the position 177 has been substituted to aspartic acid.

[28]

An active-form mutant glutamate dehydrogenase having an amino acid sequence shown in SEQ ID NO: 9, wherein:
valine at the position 174 has been substituted to aspartic acid,
lysine at the position 257 has been substituted to tyrosine and/or
leucine at the position 261 has been substituted to glutamic acid.

[29]

A method for producing an active-form mutant enzyme comprising expressing a gene that codes for the amino acid sequence according to any one of [24] to [28] in an *Escherichia coli* expression system and obtaining a protein.

[30]

The producing method according to [29], wherein the active-form mutant enzyme is an active-form mutant mandelonitrile oxidase, an active-form mutant arginine decarboxylase, an active-form mutant ornithine decarboxylase, an active-form mutant luciferase or an active-form mutant glutamate dehydrogenase.

[31]

The producing method according to any one of [3] to [22], wherein the insoluble-form protein is one protein selected from the group consisting of an enzyme, a cytokine, a haemoglobin and a myoglobin.

[32]

The method according to any one of [3] to [22], wherein the insoluble-form protein is one protein selected from the group consisting of IFN-γ, IL-2, IFNβ and human growth hormone.

Advantageous Effects of Invention

According to the present invention, various enzymes which are inactive-form enzymes in a heterologous expression system may be expressed as active-form mutant enzymes in the heterologous expression system which are mutant proteins in which a hydrophobic amino acid that is present in a hydrophilic domain of an α-helix structure region in the enzyme proteins is substituted to more hydrophilic amino acid or mutant proteins in which a hydrophilic amino acid that is present in a hydrophobic domain of the region is substituted to more hydrophobic amino acid.

Further, according to the present invention, by focusing on the conservation in sequence identity of similar amino acid sequences, an active-form mutant enzyme may be expressed in a heterologous expression system which is a mutant protein in which an amino acid with low conservation is substituted to an amino acid with higher conservation.

According to the present invention, various proteins which are insoluble in a heterologous expression system may be expressed as soluble mutant proteins in the heterologous expression system which are mutant proteins in which a hydrophobic amino acid that is present in a hydrophilic domain of an α-helix structure region in the proteins is substituted to more hydrophilic amino acid or mutant proteins in which a hydrophilic amino acid that is present in a hydrophobic domain of the region is substituted to more hydrophobic amino acid.

Further, according to the present invention, by focusing on the conservation in sequence identity of similar amino acid sequences, a soluble mutant protein may be expressed in a heterologous expression system which is a mutant protein in which an amino acid with low conservation is substituted to an amino acid with higher conservation.

BRIEF DESCRIPTION OF DRAWINGS

FIG. 7A is a graphical image of secondary structure prediction of arginine decarboxylase and FIG. 7B shows a helical wheel of 8th and 13th α-helices from the N-terminal and hydrophilic and hydrophobic domains and mutation sites.

FIG. 7C shows the linear representation of the helical wheel together with the hydropathy index of each amino acid and the sum of each row.

FIG. 14 shows a graphical image of secondary structure prediction of ornithine decarboxylase.

FIG. 15 shows a graphical image of secondary structure prediction of glutamic acid dehydrogenase.

DESCRIPTION OF EMBODIMENTS

Figure 1:
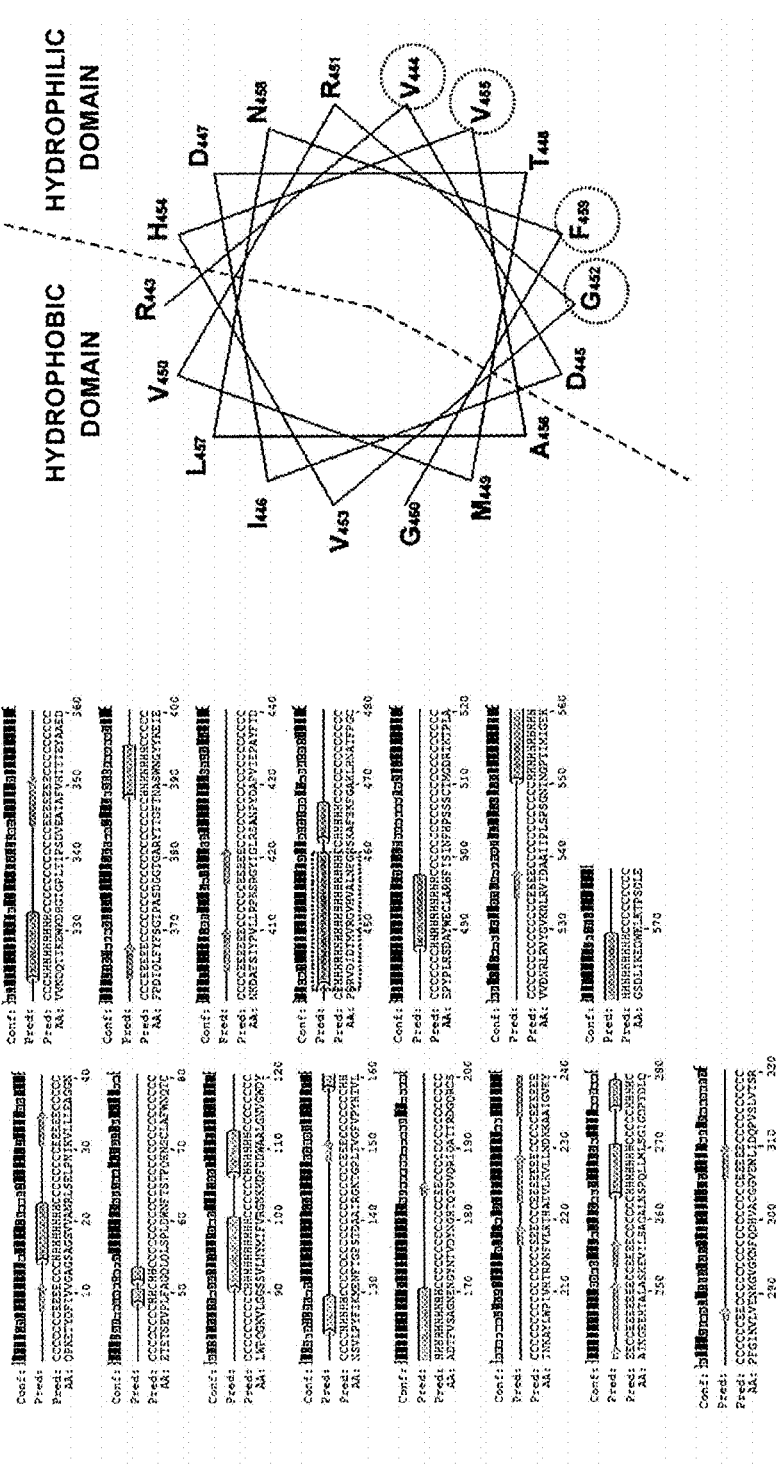
FIG. 1 is a graphical image of secondary structure prediction of mandelonitrile oxidase (A) and a helical wheel of an α-helix (RVDIDTMVRGVHVALNFG) containing a mutation site of valine at the position 455 (B) and hydrophilic and hydrophobic domains and the mutation site, valine at the position 455.

<Producing Method of an Active-Form Mutant Enzyme (Producing Method of the First Embodiment)>

The method for producing an active-form mutant enzyme of the present invention (producing method of the first embodiment) is:

a method for producing an active-form mutant enzyme comprising:

expressing, in a heterologous expression system, a gene having a base sequence that codes for an amino acid sequence in which:

at least one hydrophobic amino acid that is present in a hydrophilic domain of an α-helix structure region is substituted (to an amino acid with higher hydrophilicity or lower hydrophobicity than the amino acid to be substituted) and/or at least one hydrophilic amino acid that is present in a hydrophobic domain of the α-helix structure region is substituted (to an amino acid with higher hydrophobicity or lower hydrophilicity than the amino acid to be substituted), wherein the α-helix structure region is in an amino acid sequence of a protein of which native form exhibits an enzyme activity but which exhibits no enzyme activity or a feeble enzyme activity when expressing a gene of the protein in a heterologous expression system (hereinafter "an inactive-form enzyme); and selecting a protein (hereinafter "an active-form mutant enzyme") that exhibits the same sort of activity as that obtained in the native form.

The method for producing the active-form mutant enzyme specifically include the following steps:

(1) specifying a protein of which native form exhibits an enzyme activity but which exhibits no enzyme activity or a feeble enzyme activity when expressing a gene of the protein in a heterologous expression system (hereinafter "an inactive-form enzyme");

(2a) specifying an α-helix structure region of the inactive-form enzyme specified in step (1), specifying a hydrophilic domain and/or hydrophobic domain of the specified α-helix structure region, and specifying a hydrophobic amino acid that is present in the hydrophilic domain and/or a hydrophilic amino acid that is present in the hydrophobic domain;

(3a) preparing a gene having a base sequence that codes for an amino acid sequence in which at least one hydrophobic amino acid that is present in the hydrophilic domain of the α-helix structure region in the amino acid sequence of the inactive-form enzyme is substituted (to an amino acid with higher hydrophilicity or lower hydrophobicity than the amino acid to be substituted) and/or at least one hydrophilic amino acid that is present in the hydrophobic domain of the α-helix structure region is substituted (to an amino acid having higher hydrophobicity or lower hydrophilicity than the amino acid to be substituted); and (4a) expressing, in a heterologous expression system, the gene having the base sequence prepared in step (3a) to obtain a protein and selecting from the obtained proteins, a protein ("an active-form mutant enzyme") that exhibits the same sort of activity as that obtained in the native form.

Step (1)

In step (1), a protein of which native form exhibits an enzyme activity but which exhibits no enzyme activity or a feeble enzyme activity when expressing a gene of the protein in a heterologous expression system is specified. Such a protein is referred to as an inactive-form enzyme. The inactive-form enzyme as used herein also encompasses an enzyme which exhibits activity when expressed in a certain heterologous expression system but is inactive in other heterologous expression systems. The source or type of the inactive-form enzyme is not particularly limited.

The protein (hereinafter also referred to as "a target protein") which is a subject of the present invention and of which native form exhibits an enzyme activity is not particularly limited and examples thereof include a protein of microorganism origin, a protein of animal origin and a protein of plant origin. The type of the inactive-form enzyme is not particularly limited and examples thereof include oxidoreductases, transferases, hydrolases, isomerases, lyases and ligases.

The heterologous expression system refers to, when the system producing a target protein is an organism, an expression system employing a host that is different from the organism producing the target protein, or a cell-free protein synthetic system. The type of the expression system employing a different host or the type of the cell-free protein synthetic system are not particularly limited. When the organism producing a target protein is a cell-free protein synthetic system, the heterologous expression system refers to an expression system employing any host or a cell-free protein synthetic system which is of a different type from the cell-free protein synthetic system producing the target protein. The expression system employing a host may include those generally used in genetic engineering without limitation and examples thereof include an *E. coli* expression system, a yeast expression system, a *Brevibacillus* expression system, a *Corynebacterium* expression system, an *Aspergillus* expression system, an insect cell expression system, an *Actinomyces* expression system, a plant cell expression system and an animal cell expression system. Examples of the cell-free protein synthetic system include human cultured cells, rabbit reticulocytes, insect cultured cells, wheat germ, an extreme thermophile *Thermus thermophilus*, a hyperthermophile archaea *Thermococcus kodakarensis*, a cell-free protein synthetic system employing an *E. coli* extract, a reconstituted cell-free protein synthetic system PURE system and the like.

Specifying an inactive-form enzyme in a heterologous expression system is carried out by introducing a gene that codes for a protein of which native form exhibits an enzyme activity into a heterologous expression system, expressing the protein in the heterologous expression system and examining whether or not the obtained protein has the enzyme activity as exhibited by the native form and if the protein exhibits the activity, how much the activity is. Expression in a heterologous expression system may be carried out by a standard manner of each heterologous expression system. The details are described hereinafter.

The phrase "a protein which exhibits no activity when expressing a gene of the protein in a heterologous expression system" is the case where the result of an activity assay of the subject enzyme is at or below the detection limit. The phrase "a protein which exhibits a feeble activity" is the case where the activity in an activity assay of the subject enzyme is 10% or less, preferably 5% or less and more preferably 1% or less of the enzyme activity exhibited by the protein in the native form.

Step (2a)

Step (2a) is the step of specifying an α-helix structure region of the inactive-form enzyme specified in step (1) (substep 1), specifying a hydrophilic domain and/or hydrophobic domain of the specified α-helix structure region (substep 2) and specifying a hydrophobic amino acid that is present in the hydrophilic domain and/or a hydrophilic amino acid that is present in the hydrophobic domain (substep 3).

Step (2a) Includes 3 Substeps.

In substep 1, an α-helix structure region of the inactive-form enzyme specified in step (1) is specified by, for example, a secondary structure predicting method. Specifying an α-helix structure region of the inactive-form enzyme specified in step (1) by a secondary structure predicting method may be carried out by predicting the secondary structure using, for example, a gene analysis software such as a genetic information processing software GENETYX or a secondary structure predicting programme such as PSIPRED (http://bioinf.cs.ucl.ac.uk/psipred/) (FIG. 1A). In FIG. 1A, amino acids S15 to N22, L49 to F50, G52 to Q53, S91 to V100, F107 to A112, P125 to K129, V159 to E170, S264 to L270, P276 to L279, D324 to D332, N389 to Y395, R443 to G460, K463 to K467, D488 to H497 and N551 to W569 correspond to an α-helix region.

All amino groups in amino acids constituting a back bone of an α-helix form hydrogen bonds with carboxyl groups of amino acids which are 4 residues away. The number of amino acids constituting an α-helix region is not limited; however, in view of finding a hydrophobic domain and a hydrophilic domain in the following substep 2, the number is preferably 7 residues or more and more preferably 12 residues or more.

Substep 2 is the substep of specifying a hydrophilic domain and/or hydrophobic domain of the specified α-helix structure region. Specifying a hydrophilic domain and/or a hydrophobic domain may be carried out by drawing a helical wheel of the α-helix structure region. Helical wheels may be generated by using pepwheel (http://emboss.bioinformatics.nl/cgi-bin/emboss/pepwheel) and the like (FIG. 1B). A helical wheel such as the one in FIG. 1B represents the type and position of amino acids in an α-helix. In the present invention, it is preferable to draw a helical wheel with 7 residues per cycle as shown in FIG. 2A, then align amino acids belonging to the helix in the helical wheel shown in FIG. 2A in order of 1→5→2→6→3→7→4, begin a new row at the eighth residue which is regarded as 1 as above and draw a linear representation of a helical wheel (FIG. 2B), thereby specifying a hydrophilic domain and/or a hydrophobic domain of the α-helix structure region.

More specifically, the following is a preferable embodiment of specifying a hydrophilic domain and/or a hydrophobic domain.

(a) A helical wheel of an α-helix structure region is drawn by using a secondary structure predicting method, amino acids at positions 1, 5, 2, 6, 3, 7 and 4 on the helical wheel are aligned in this order to form a sequence and the procedure is repeated to form at least two amino acid sequences each of which has 7 amino acids; however, it is sufficient that the second sequence has 5 or more amino acids. Namely, with the second sequence having at least 5 amino acids, a hydrophilic domain and/or a hydrophobic domain may be specified (drawing of a linear representation of helical wheel).

(b) In the amino acid sequence region where at least two sequences are aligned, a row in which the sum of the hydropathy index of the amino acids therein is 0 or more is defined as a hydrophobic row and a row in which the sum of the hydropathy index of the amino acids therein is less than 0 is defined as a hydrophilic row.

(c) A bunch of 3 or 4 consecutive hydrophobic rows is defined as the hydrophobic domain and a bunch of 4 or 3 consecutive hydrophilic rows is defined as the hydrophilic domain. When a bunch of 3 consecutive hydrophobic rows is defined as a hydrophobic domain, a bunch of 4 consecutive hydrophilic rows is defined as a hydrophilic domain. When a bunch of 4 consecutive hydrophobic rows is defined as a hydrophobic domain, a bunch of 3 consecutive hydrophilic rows is defined as a hydrophilic domain. The sum of the hydropathy index of any one row that is internal to 4 hydrophobic rows in the hydrophobic domain may be less than 0 and the sum of the hydropathy index of any one row that is internal to 4 hydrophilic rows in the hydrophilic domain may be 0 or more.

The phrase in (c) "one row that is internal to 4 hydrophobic rows in the hydrophobic domain" means any one of two rows which do not directly contact a hydrophilic domain and the phrase "one row that is internal to 4 hydrophilic rows in the hydrophilic domain" means any one of two rows which do not directly contact a hydrophobic domain.

The hydropathy index (NPL 6) is an index representing hydrophilicity and hydrophobicity of amino acids. In the present invention, an amino acid with a hydropathy index of less than 0 is indicated as a hydrophilic amino acid and an amino acid with a hydropathy index of 0 or more is indicated as a hydrophobic amino acid.

TABLE 1

Hydropathy index

| Amino acid | Hydropathy index | |
|---|---|---|
| Isoleucine (I) | 4.5 | Hydrophobic amino acids |
| Valine (V) | 4.2 | |
| Leucine (L) | 3.8 | |
| Phenylalanine (F) | 2.8 | |
| Cysteine (C) | 2.5 | |
| Methionine (M) | 1.9 | |
| Alanine (A) | 1.8 | |
| Glycine (G) | −0.4 | Hydrophilic amino acids |
| Threonine (T) | −0.7 | |
| Tryptophan (W) | −0.9 | |
| Serine (S) | −0.8 | |
| Tyrosine (Y) | −1.3 | |
| Proline (P) | −1.6 | |
| Histidine (H) | −3.2 | |
| Glutamic acid (E) | −3.5 | |
| Glutamine (Q) | −3.5 | |
| Aspartic acid (D) | −3.5 | |
| Asparagine (N) | −3.5 | |
| Lysine (K) | −3.9 | |
| Arginine (R) | −4.5 | |

Specifying a hydrophilic domain and/or a hydrophobic domain by this manner is more specifically described hereinafter by using the proteins in Examples as an example.

The following description is made by using mandelonitrile oxidase derived from *Chamberlinius hualinensis* as an example and referring to FIGS. 6A to 6C. FIG. 6A is a helical wheel of an α-helix structure region drawn by a secondary structure predicting method as in (a). FIG. 6B is a linear representation of the helical wheel in FIG. 6A. Each circle represents an amino acid, an open circle represents a hydrophilic amino acid, a filled circle represents a hydrophobic amino acid and each number represents the position of each amino acid. FIG. 6C shows the linear representation of the helical wheel together with the hydropathy index of each amino acid. For example, the amino acid R (arginine) shown on the top right has a hydropathy index of −4.5. On the left of the figure, the sums of the hydropathy index of amino acids in each row are indicated, which are, from the top in this order, (i) 3.5, (ii) −6.7, (iii) −3.8, (iv) 3.5, (v) −1.1, (vi) 3.7 and (vii) 8.3. In (b), it is defined that in the amino acid sequence region where at least two sequences are aligned (in this example, three sequences are aligned), the row having the sum of the hydropathy index of amino acids in the row of 0 or more is defined as a hydrophobic row and the row having the sum of less than 0 is defined as a hydrophilic row, and thus the row (i) of 3.5 is defined as a hydrophobic row, the row (ii) of −6.7 is defined as a hydrophilic row, the row (iii) of −3.8 is defined as a hydrophilic row, the row (iv) of 3.5 is defined as a hydrophobic row, the row (v) of −1.1 is defined as a hydrophilic row, the row (vi) of 3.7 is defined as a hydrophobic row and the row (vii) of 8.3 is defined as a hydrophobic row. In (c), it is defined that a bunch of 3 or 4 consecutive hydrophobic rows is defined as a hydrophobic domain and a bunch of 4 or 3 consecutive hydrophilic rows is defined as a hydrophilic domain and when a bunch of 3 consecutive hydrophobic rows is defined as a hydrophobic domain, a bunch of 4 consecutive hydrophilic rows is defined as a hydrophilic domain and when a bunch of 4 consecutive hydrophobic rows is defined as a hydrophobic domain, a bunch of 3 consecutive hydrophilic rows is defined as a hydrophilic domain. According to the definition, the bunch of 4 consecutive rows of (ii), (iii), (iv) and (v) may be defined as a hydrophobic domain and the bunch of 3 consecutive rows of (vi), (vii) and (i) may be defined as a hydrophilic domain. Although the row (iv) of 3.5 in the hydrophilic domain is a hydrophobic row, this row corresponds to the row that is internal to 4 hydrophilic rows (namely, the row that does not directly contact a hydrophobic domain), and thus the row corresponds to an exception as described in the provision where the sum of the hydropathy index of any one row that is internal to 4 hydrophilic rows in the hydrophilic domain may be 0 or more.

As described above, in this example, the bunch of 4 consecutive rows (ii), (iii), (iv) and (v) may be defined as a hydrophobic domain and the bunch of 3 consecutive rows (vi), (vii) and (i) may be defined as a hydrophilic domain.

Substep 3 is the substep of specifying a hydrophobic amino acid that is present in the hydrophilic domain and/or a hydrophilic amino acid that is present in the hydrophobic domain. Specifying a hydrophobic amino acid that is present in a hydrophilic domain and specifying a hydrophilic amino acid that is present in a hydrophobic domain are carried out by using the hydropathy index. In the present invention, among amino acids in the hydrophilic domain, an amino acid with a hydropathy index of 0 or more is specified as a hydrophobic amino acid and among amino acids in the hydrophobic domain, an amino acid with a hydropathy index of less than 0 is specified as a hydrophilic amino acid.

The hydrophilic amino acid includes threonine (T), serine (S), tyrosine (Y), histidine (H), glutamic acid (E), glutamine (Q), aspartic acid (D), asparagine (N), lysine (K), arginine (R) and glycine (G) and the hydrophobic amino acid includes isoleucine (I), valine (V), leucine (L), phenylalanine (F), cysteine (C), methionine (M) and alanine (A) (see Table 1). As tryptophan (W) and proline (P) have a hydropathy index of less than 0, the amino acids are classified as hydrophilic amino acids. However, in the nature of the side chains, the amino acids are classified as hydrophobic amino acids. Therefore, it is defined that tryptophan and proline do not belong to either hydrophilic or hydrophobic amino acid and upon calculation of the sum of the hydropathy index of amino acids in a row as described above, the hydropathy index of both tryptophan and proline is regarded as 0 (zero). However, in terms of substitution of amino acids in the step (3a), tryptophan (W) and proline (P) may be included in hydrophilic amino acids as examples of substituting amino acids.

For example, in the example shown in FIG. 6C described above, 2 Vs (valines), G (glycine) and F (phenylalanine) are hydrophobic amino acids that are present in the hydrophilic domain and R (arginine) is a hydrophilic amino acid that is present in the hydrophobic domain.

Step (3a)

A gene is prepared which has a nucleic acid sequence that codes for an amino acid sequence in which at least one hydrophobic amino acid that is present in the hydrophilic domain of the α-helix structure region in the amino acid sequence of the inactive-form enzyme is substituted. In this case, the amino acid is substituted to an amino acid with higher hydrophilicity or lower hydrophobicity than the amino acid to be substituted. Alternatively, a gene is prepared which has a nucleic acid sequence that codes for an amino acid sequence in which at least one hydrophilic amino acid that is present in the hydrophobic domain of the α-helix structure region in the amino acid sequence of the inactive-form enzyme is substituted. In this case, the amino acid is substituted to an amino acid with higher hydrophobicity or lower hydrophilicity than the amino acid to be substituted. The degree of hydrophilicity and the degree of hydrophobicity may be determined by using the hydropathy index described above. Genes having known amino acid sequences may be prepared according to standard methods and the introduction of desired amino acid residue mutations by way of a mutation introducing technique may also be carried out according to standard methods. In the present invention, a mutation may be introduced at the specified residue by using, for example, QuikChange® Lightning Site-Directed Mutagenesis Kit (manufactured by Agilent Technologies).

A hydrophobic amino acid that is present in the hydrophilic domain is, in cases when the hydropathy index is used, substituted to an amino acid with a lower hydropathy index value than the amino acid to be substituted. The amino acid may be still a hydrophobic amino acid even if the amino acid has a lower hydropathy index value than the amino acid to be substituted. Further, a hydrophobic amino acid that is present in the hydrophilic domain may be substituted to a hydrophilic amino acid with a lower hydropathy index value than the amino acid to be substituted and also with a hydropathy index value of less than 0. Generally, by substituting a hydrophobic amino acid that is present in the hydrophilic domain to a hydrophilic amino acid with a lower hydropathy index value than the amino acid to be substituted and also with a hydropathy index value of less than 0, the tendency of surely obtaining an active-form mutant enzyme may be increased.

Similarly, a hydrophilic amino acid that is present in the hydrophobic domain is substituted to an amino acid with a higher hydropathy index value than the amino acid to be substituted. Further, a hydrophilic amino acid that is present in the hydrophobic domain may be substituted to an amino acid with a higher hydropathy index value than the amino acid to be substituted and with a hydropathy index value of 0 or more. Generally, by substituting a hydrophilic amino acid that is present in the hydrophobic domain to an amino acid with a higher hydropathy index value than the amino acid to be substituted and with a hydropathy index value of 0 or more, the tendency of surely obtaining an active-form mutant enzyme may be increased.

Figure 4:
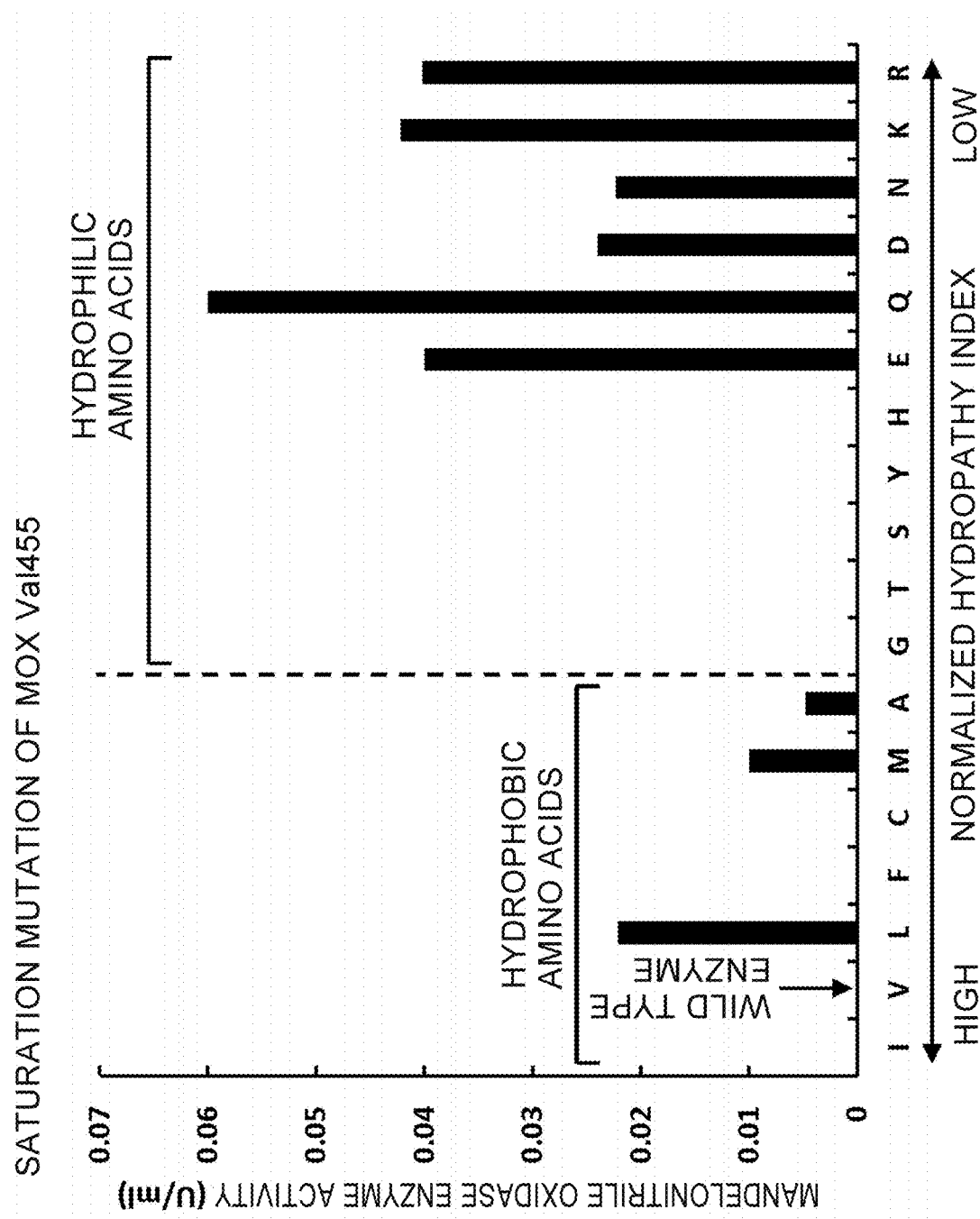
FIG. 4 shows oxidase activity (U/ml) and amino acid sequence conservation (%) of enzymes obtained by substituting valine at the position 455 of mandelonitrile oxidase to other 19 amino acids; bars indicate oxidase activity and open circles show amino acid sequence conservation; and the letters are as follows: A: alanine, C: cysteine, D: aspartic acid, E: glutamic acid, F: phenylalanine, G: glycine, H: histidine, I: isoleucine, K: lysine, L: leucine, M: methionine, N: asparagine, P: proline, Q: glutamine, R: arginine, S: serine, T: threonine, V: valine, W: tryptophan and Y: tyrosine.

For example, in the example shown in FIG. 6C described above, 2 Vs (valines), G (glycine) and F (phenylalanine) are hydrophobic amino acids in the hydrophilic domain and R (arginine) is a hydrophilic amino acid that is present in the hydrophobic domain. In Examples, 2 Vs (valines) (444 and 455) were substituted to amino acids with higher hydrophilicity or lower hydrophobicity than V. The results are indicated in FIG. 4 (V455) and FIG. 5 (V444). In FIG. 4 (V455), almost half of mutant proteins exhibited enzyme activity and in FIG. 5 (V444), most of the mutant proteins exhibited enzyme activity, indicating that active-form mutant enzymes were obtained.

Step (4a)

The gene having the nucleic acid sequence prepared in step (3a) is expressed in a heterologous expression system which is the same as or different from the one described above to obtain a protein having a mutation introduced therein. Expression of the protein having a mutation introduced therein in a heterologous expression system may be carried out according to standard methods.

Steps (3a) and (4a) are more specifically described hereinbelow.

(Promoter)

In the method of the present invention, a heterologous expression host such as *E. coli* is first prepared which harbours a gene that codes for a protein having an amino acid sequence of a target protein in which a predetermined mutation is introduced at a predetermined position. For example, a heterologous expression host such as *E. coli* which harbours a gene that codes for a protein (mutagenized target protein) in which a mutation is introduced to a target protein may be prepared by providing a vector having the gene that codes for the mutagenized target protein under the control of an inducible promoter and introducing the vector into *E. coli*. The inducible promoter is not particularly limited and may be any known inducible promoters. For example, an inducible promoter which exhibits transcriptional activity in the presence of isopropyl-1-thio-β-D-galactoside (IPTG) may be used. Examples of such a promoter include a Trp promoter, a Lac promoter, a Trc promoter, a Tac promoter, a T7 promoter and the like. Other promoters which exhibit transcriptional activity in the presence of other inducers than IPTG and other promoters which exhibit transcriptional activity according to culture conditions such as components in media or temperature (for example, low temperature) may also be used as the inducible promoter.

(Vector)

The vector is not particularly limited as long as the vector may be replicated in the heterologous expression host such as *E. coli* and may be any of plasmid vectors, phage vectors and the like. Examples of the specific vector may include vectors of pCDF series, pRSF series, pET series and the like. For example, for an expression vector of pET (having a T7 promoter), E. coli BL21 (DE3) and JM109 (DE3) may be used. The vector may be introduced into E. coli by applying various methods generally known as transformation technique. Specific methods which may be applied include calcium phosphate transfection, electroporation, lipofection and the like. Transfection may be transient or stable.

E. coli may be the one that harbours a plasmid pLysS (BL21 (DE3) pLysS: manufactured by Invitrogen Corporation). The plasmid pLysS expresses a low level of T7 ribozyme. T7 ribozyme inhibits T7 RNA polymerase and thus can suppress expression of a mutagenized target protein before expression induction by IPTG. Further, in a heterologous expression host such as E. coli, a chaperone and the like may be co-expressed in order to aid correct folding of a mutagenized target protein.

(Culture Conditions)

When culturing E. coli that harbours a gene that codes for a mutagenized target protein sequence, any of a batch culture, a continuous culture and the like may be carried out. The culture may be of a static culture and a shake culture among which shake culture is preferred. As a medium, LB medium (5.0 g/L Yeast extract, 10.0 g/L NaCl, 10.0 g/L Tryptone) and the like may be used. The procedure of culture is not particularly limited as far as recombinant E. coli can be grown and examples thereof include culturing E. coli at 37° C. until a cell turbidity of about 0.5 is obtained, adding IPTG and then culturing cells at a temperature of 16° C. to 37° C. for 16 to 24 hours. In case of heterologous expression hosts other than E. coli, well-known culture methods used for the respective hosts may be applied.

(Protein Extraction)

After the main culture, the heterologous expression host may be disrupted to prepare a crude enzyme solution containing a mutagenized target protein. In a conventional method, when a heterologous gene is expressed at a large scale in bacteria and the like by recombinant DNA technique, the produced protein may form inclusion bodies which are an insoluble substance accumulated in the cells. In the present invention, the host cells such as E. coli are collected, the cells are disrupted on an ultrasonicator or the like and separating a supernatant from a pellet including inclusion bodies by centrifugation to obtain the supernatant (soluble fraction) which is used as a crude enzyme solution. The mutagenized target protein obtained according to the present method is usually soluble, and thus the crude protein suspension contains the mutagenized target protein having predetermined activity and function. Therefore, the obtained crude protein suspension may be directly used as a solution containing the mutagenized target protein. The mutagenized target protein may alternatively be used after isolation and purification from the obtained crude protein suspension. In this case, isolation and purification of the mutagenized protein may be carried out by a common biochemical procedure (such as ammonium sulphate precipitation, gel chromatography, ion-exchange chromatography and affinity chromatography) or an appropriate combination thereof. The mutagenized target protein after isolation and purification may be used, for example, in the form of a suspension in a buffer having a predetermined pH.

From mutagenized proteins expressed in the heterologous expression system, a protein (active-form mutant enzyme) that exhibits the same sort of activity as that obtained in the native form is selected. Selection of the active-form mutant enzyme may be carried out as follows. Selection may be carried out by assaying an enzyme activity in the system in which the enzyme activity that is obtained in the native form can be assayed. The enzyme activity assay may appropriately be carried out by a method known for each enzyme.

For example, enzyme activity of mandelonitrile oxidase may be assayed according to a colorimetric assay by reaction with a substrate mandelonitrile together with 4-aminoantipyrine, TOOS and peroxidase. Enzyme activity of arginine or ornithine decarboxylase may be assayed according to a colorimetric assay by reaction with a substrate arginine or ornithine together with an amine oxidase that acts with the oxidation reaction product, 4-aminoantipyrine, TOOS and peroxidase. Enzyme activity of luciferase may be assayed by allowing reaction with a substrate coelenterazine and measuring generated luminescence. Enzyme activity of glutamate dehydrogenase may be assayed by detecting an increment of generated NADH after addition of a substrate glutamic acid as well as $NAD^+$ as an amount of change of the absorbance at 340 nm.

Based on the result of the enzyme activity assay, whether or not the active-form mutant enzyme is obtained may be found and a mutation which provides the active-form mutant enzyme may be found. The active-form mutant enzyme may have, for example, an enzyme activity value that is in the range of 2 times to infinity of the enzyme activity value of an inactive-form enzyme. When an inactive-form enzyme does not exhibit any activity (in cases where the result of assay is below the detection limit), the increase rate of the enzyme activity value is infinity and when an inactive-form enzyme exhibits a feeble activity, the enzyme activity value is 2 times or more and more preferably 10 times or more of the feeble activity.

<Method for Producing an Active-Form Mutant Enzyme (Producing Method of the Second Embodiment)>

The method for producing an active-form mutant enzyme of the present invention (producing method of the second embodiment) includes the following steps:

(1) specifying a protein of which native form exhibits an enzyme activity but which exhibits no enzyme activity or a feeble enzyme activity when expressing a gene of the protein in a heterologous expression system (hereinafter "an inactive-form enzyme");

(2b) determining a conservation of at least some amino acids in an amino acid sequence of the inactive-form enzyme specified in step (1) and specifying an amino acid with relatively low conservation;

(3b) preparing a gene having a base sequence that codes for an amino acid sequence in which at least one amino acid with relatively low conservation is substituted to an amino acid with higher conservation than said amino acid; and (4b) expressing, in a heterologous expression system, the gene having the base sequence prepared in step (3b) to obtain a protein and selecting from the obtained proteins, a protein (hereinafter "an active-form mutant enzyme") that has the same sort of activity as that obtained in the native form.

Step (1) is identical to step (1) in the method for producing an active-form mutant enzyme of the present invention (producing method of the first embodiment) and the description in the producing method of the first embodiment may be referred to.

Step (2b)

Step (2b) is the step of determining a conservation in sequence identity of at least some amino acids in an amino acid sequence of the inactive-form enzyme specified in step (1) and specifying an amino acid with relatively low conservation.

In this step, other proteins having high amino acid sequence identity with the inactive-form enzyme specified in step (1) are used, the identity is searched by, for example, BLAST (http://blast.ncbi.nlm.nih.gov/Blast.cgi?PROGRAM=blastp&PAGE_TYPE=BlastSearch&LINK_LOC=blasthome) and the respective sequence conservation is calculated on INTMSAlign (NPL 7). Other proteins having high amino acid sequence identity with the inactive-form enzyme are selected, for example, as follows. The sequence of an inactive-form enzyme is entered in the section "Sequence" on the BLAST site, 5000 is selected as the value of "Max target sequences" of the "General Parameters" under the "Algorithm parameters" section below and 1.0E-3 is entered as the value of "Expect threshold" and then the BLAST search is started, thereby other proteins having high identity can be selected. By downloading all the obtained protein sequences having high identity in FASTA format and entering the sequences to INTMSAlign, sequence conservation may be calculated.

The sequence conservation may be calculated for the entire amino acid sequence or a part of the amino acid sequence of the inactive-form enzyme. When the sequence conservation is calculated for a part of the amino acid sequence, the part of the sequence may be, for example, an α-helix sequence of the enzyme protein; however, it should be noted that it is not intended to be limited to an α-helix sequence. The sequence may be, other than an α-helix sequence, a β-structure, a loop and the like. However, it should also be noted that it is not intended to be limited to these sequences.

Step (3b)

Step (3b) is the step of preparing a gene having a base sequence that codes for an amino acid sequence in which at least one amino acid with relatively low conservation specified in step (2b) is substituted to an amino acid with higher conservation than said amino acid. In step (3b), preparation of a gene having a base sequence that codes for a mutant amino acid sequence, namely, the procedures other than selection of the amino acid to be substituted which is carried out by the method of step (2b), may be carried out by referring to step (3a) in the producing method of the first embodiment of an active-form mutant enzyme of the present invention.

Step (4b)

Step (4b) is the step of expressing, in a heterologous expression system, the gene having the base sequence prepared in step (3b) to obtain a protein and selecting from the obtained proteins, a protein (active-form mutant enzyme) that has the same sort of activity as that obtained in the native form. Step (4b) may be carried out by referring to step (4a) in the producing method of the first embodiment of an active-form mutant enzyme of the present invention.

Example 3 (expression of luciferase derived from *Metridia pacifica* as an active-form mutant enzyme) and Example 4 (expression of amino acid degradation enzymes derived from *Drosophila melanogaster* as active-form mutant enzymes focusing on α-helices and amino acid residue conservation) below are examples of the producing method of the second embodiment.

In Example 3, the amino acid conservation of two amino acid sequence regions, L76 to A89 (see Table 4) and S176 to I201 (see Table 5), was respectively calculated and it was found that I80 and A177 were amino acids with low conservation. Further, for I80, a mutagenized target protein was prepared in which the amino acid was substituted to A having high conservation and for A177, a mutagenized target protein was prepared in which the amino acid was substituted to D having high conservation. As a result, although the native form was an inactive-form enzyme, active-form mutant enzymes that exhibited activity were obtained (see FIG. 12).

In Example 4, the amino acid conservation of two amino acid sequence regions, S111 to E118 and A171 to S180 (see Table 6), of ornithine decarboxylase derived from *Drosophila melanogaster* (DmODC) was respectively calculated and it was found that K117 and L176 were amino acids having low conservation. For K117, a mutagenized target protein was prepared in which the amino acid was substituted to L having high conservation and for L176, a mutagenized target protein was prepared in which the amino acid was substituted to E having high conservation. As a result, although the native form was an inactive-form enzyme, active-form mutant enzymes that exhibited activity were obtained. Similarly, the amino acid conservation of two amino acid sequence regions, V174 to L189 and G252 to F262 (see Table 7), of glutamate dehydrogenase (DmGluDH) was respectively calculated and it was found that V174, K257 and L261 were amino acids having low conservation. For V174, a mutagenized target protein was prepared in which the amino acid was substituted to D having high conservation, for K257, a mutagenized target protein was prepared in which the amino acid was substituted to Y having high conservation and for L261, a mutagenized target protein was prepared in which the amino acid was substituted to E having high conservation. As a result, although the native form was an inactive-form enzyme, active-form mutant enzymes that exhibited activity were obtained.

<Combination of the Method of the First Embodiment and the Method of the Second Embodiment for Producing an Active-Form Mutant Enzyme of the Present Invention>

When a protein that forms an enzyme has in the conformation thereof facing hydrophilic amino acid residues, amino acids on a helix may also be hydrophilic amino acids and residues involved in an enzyme reaction in a substrate pocket may be hydrophilic amino acids, and it is particularly highly possible that amino acid residues having a high sequence conservation are such amino acids. In contrast, amino acids having low sequence conservation may be present only in the enzyme and it is presumed that by removing such amino acids, an enzyme activity of the protein may be increased. The producing method of the second embodiment of the present invention utilizes the feature and increases an enzyme activity by picking up an amino acid with low sequence conservation and substituting to an amino acid with high sequence conservation. It is believed that according to the above, a highly rational mutation can be introduced in order to obtain an active-form mutant enzyme.

Figure 3:
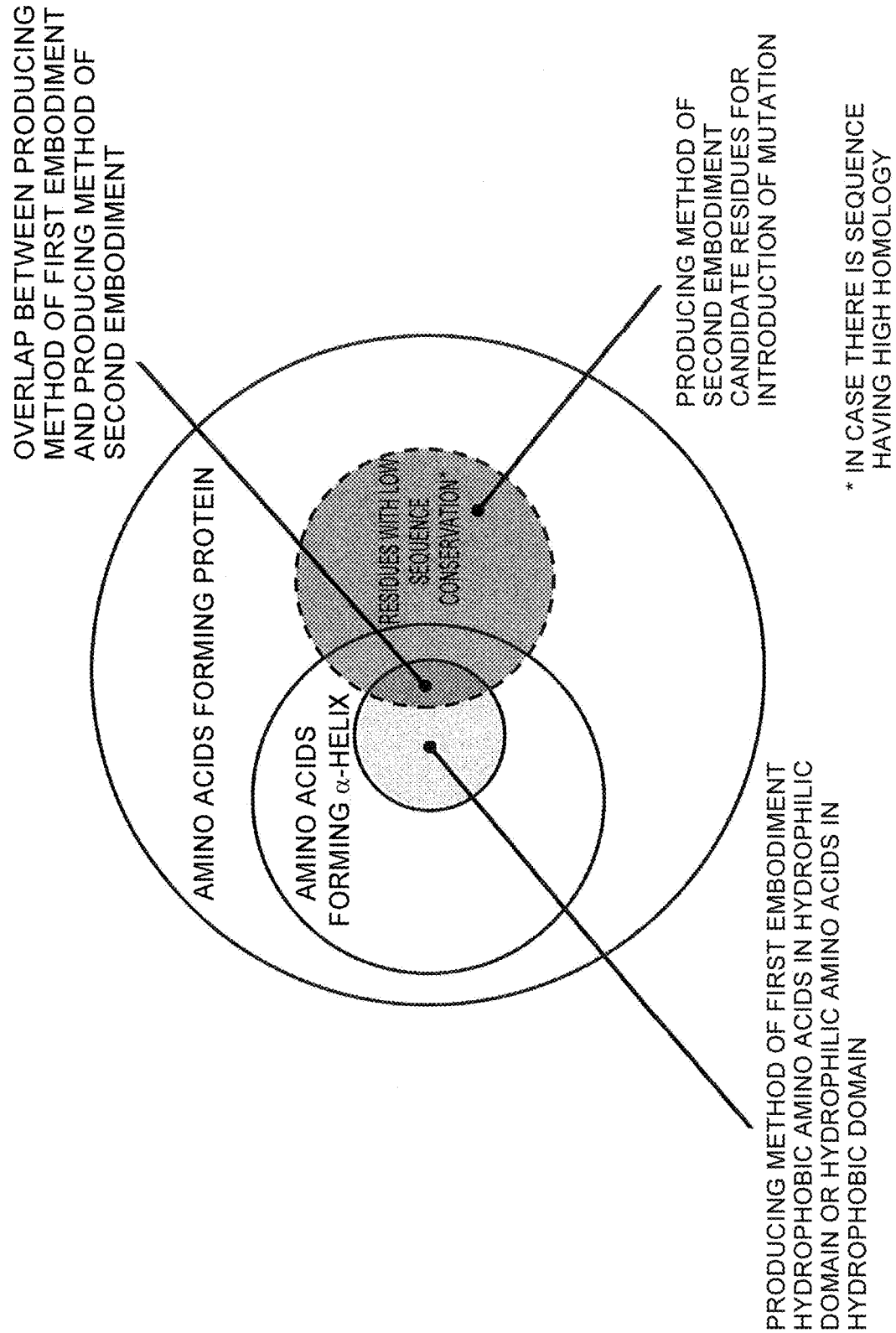
FIG. 3 is an illustration relating to the method (the producing method of the first embodiment and the producing method of the second embodiment of the present invention) for specifying a residue which may possibly allow expression of an active-form mutant enzyme.

The schematic illustration of the above relationship is shown in FIG. 3. Among amino acids that form a protein (the entire circle), there are a circle (left) of amino acids that form an α-helix sequence and a circle (right) of amino acids with low sequence conservation. In the circle (left) of amino acids that form an α-helix sequence, there is a circle (the circle on left) of hydrophobic amino acids in the hydrophilic domain or hydrophilic amino acids in the hydrophobic domain specified in the producing method of the first embodiment of the present invention. A circle (right) of amino acids with low sequence conservation specified in the producing method of the second embodiment of the present invention may overlap with the circle (left) of amino acids that form an α-helix sequence and the circle (the circle on left) of hydrophobic amino acids in the hydrophilic domain or hydrophilic amino acids in the hydrophobic domain. The overlap may not happen for some proteins.

When the overlap happens, for the inactive-form enzyme specified in step (1), a hydrophobic amino acid that is present in a hydrophilic domain and/or a hydrophilic amino acid that is present in a hydrophobic domain is specified in step (2a) in the method of the first embodiment for producing an active-form mutant enzyme of the present invention and an amino acid with relatively low conservation is specified in step (2b) in the method of the second embodiment for producing an active-form mutant enzyme of the present invention. Based on both information, steps (3a) and (4a) (step (3b) and (4b)) are carried out, so that the gene may be expressed in a heterologous expression system to obtain a protein and from the obtained proteins, a protein (active-form mutant enzyme) that exhibits the same sort of activity as that obtained in the native form may be selected. In Example 2 (expression of arginine decarboxylase derived from *Arabidopsis thaliana* as an active-form mutant enzyme), the producing method of the first embodiment and the method of the second embodiment for producing an active-form mutant enzyme of the present invention are combined.

<Active-Form Mutant Enzyme>

The present invention encompasses a novel active-form mutant enzyme selected by the method of the present invention.

The active-form mutant mandelonitrile oxidase of the present invention has an amino acid sequence shown in SEQ ID NO: 2, wherein:
valine at the position 444 has been substituted to threonine, serine, tyrosine, histidine, glutamic acid, glutamine, aspartic acid, asparagine, lysine or arginine and/or
valine at the position 455 has been substituted to glutamic acid, glutamine, aspartic acid, asparagine, lysine or arginine. The active-form mutant mandelonitrile oxidase of the present invention encompasses an enzyme with an activity that is similar to or above the enzyme activity of the native form.

Figure 5:
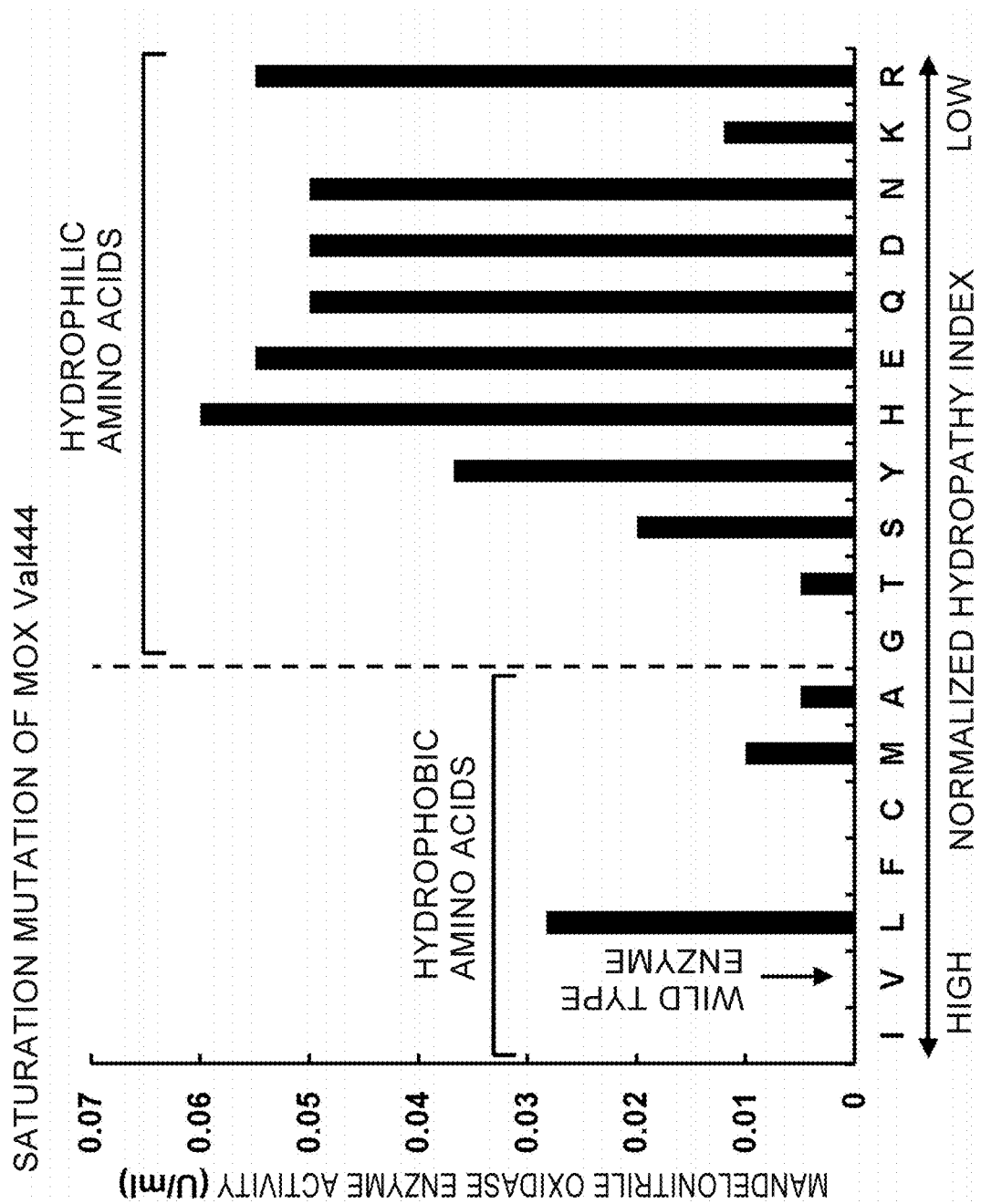
FIG. 5 shows oxidase activity (U/ml) and amino acid sequence conservation (%) of enzymes obtained by substituting valine at the position 444 of mandelonitrile oxidase to other 19 amino acids; bars indicate oxidase activity and open circles show amino acid sequence conservation; and the letters are as follows: A: alanine, C: cysteine, D: aspartic acid, E: glutamic acid, F: phenylalanine, G: glycine, H: histidine, I: isoleucine, K: lysine, L: leucine, M: methionine, N: asparagine, P: proline, Q: glutamine, R: arginine, S: serine, T: threonine, V: valine, W: tryptophan and Y: tyrosine.

Specifically, the active-form mutant mandelonitrile oxidases of the present invention in which valine at the position 455 has been substituted to other amino acids respectively exhibit, as shown in FIG. 4, mandelonitrile oxidase activity, while the native form has the enzyme activity that is substantially zero. The active-form mutant mandelonitrile oxidases of the present invention in which valine at the position 444 has been substituted to other amino acids also respectively exhibit, as shown in FIG. 5, mandelonitrile oxidase activity, while the native form has the enzyme activity that is substantially zero.

The active-form mutant arginine decarboxylase of the present invention has an amino acid sequence shown in SEQ ID NO: 3, wherein:
valine at the position 261 has been substituted to threonine, serine, glutamic acid, aspartic acid, asparagine, lysine or arginine and/or
arginine at the position 430 has been substituted to valine, leucine or alanine, and leucine at the position 435 has been substituted to histidine, glutamic acid, glutamine, aspartic acid, asparagine or lysine. The active-form mutant arginine decarboxylase of the present invention encompasses an enzyme which is an active-form mutant enzyme and has an activity that is similar to or above the enzyme activity of the native form.

Figure 8:
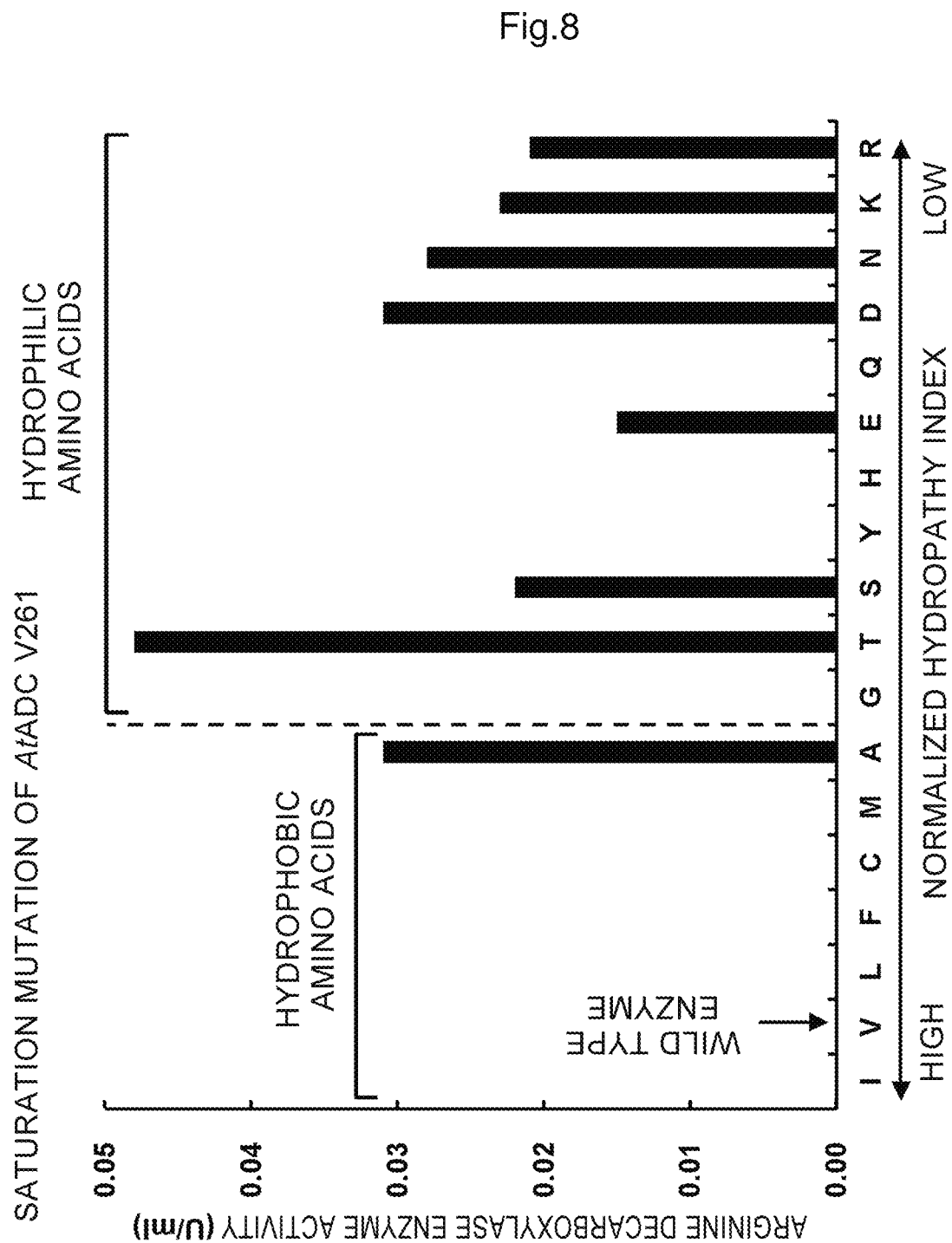
FIG. 8 shows decarboxylase activity (U/ml) and amino acid sequence conservation (%) of enzymes obtained by substituting valine at the position 261 of arginine decarboxylase to other 19 amino acids; bars indicate oxidase activity and open circles show amino acid sequence conservation; and the letters are as follows: A: alanine, C: cysteine, D: aspartic acid, E: glutamic acid, F: phenylalanine, G: glycine, H: histidine, I: isoleucine, K: lysine, L: leucine, M: methionine, N: asparagine, P: proline, Q: glutamine, R: arginine, S: serine, T: threonine, V: valine, W: tryptophan and Y: tyrosine.

The active-form mutant arginine decarboxylases of the present invention in which valine at the position 261 has been substituted to other amino acids respectively have, as shown in FIG. 8, arginine decarboxylase activity, while the native form has the enzyme activity that is substantially zero.

Figure 9:
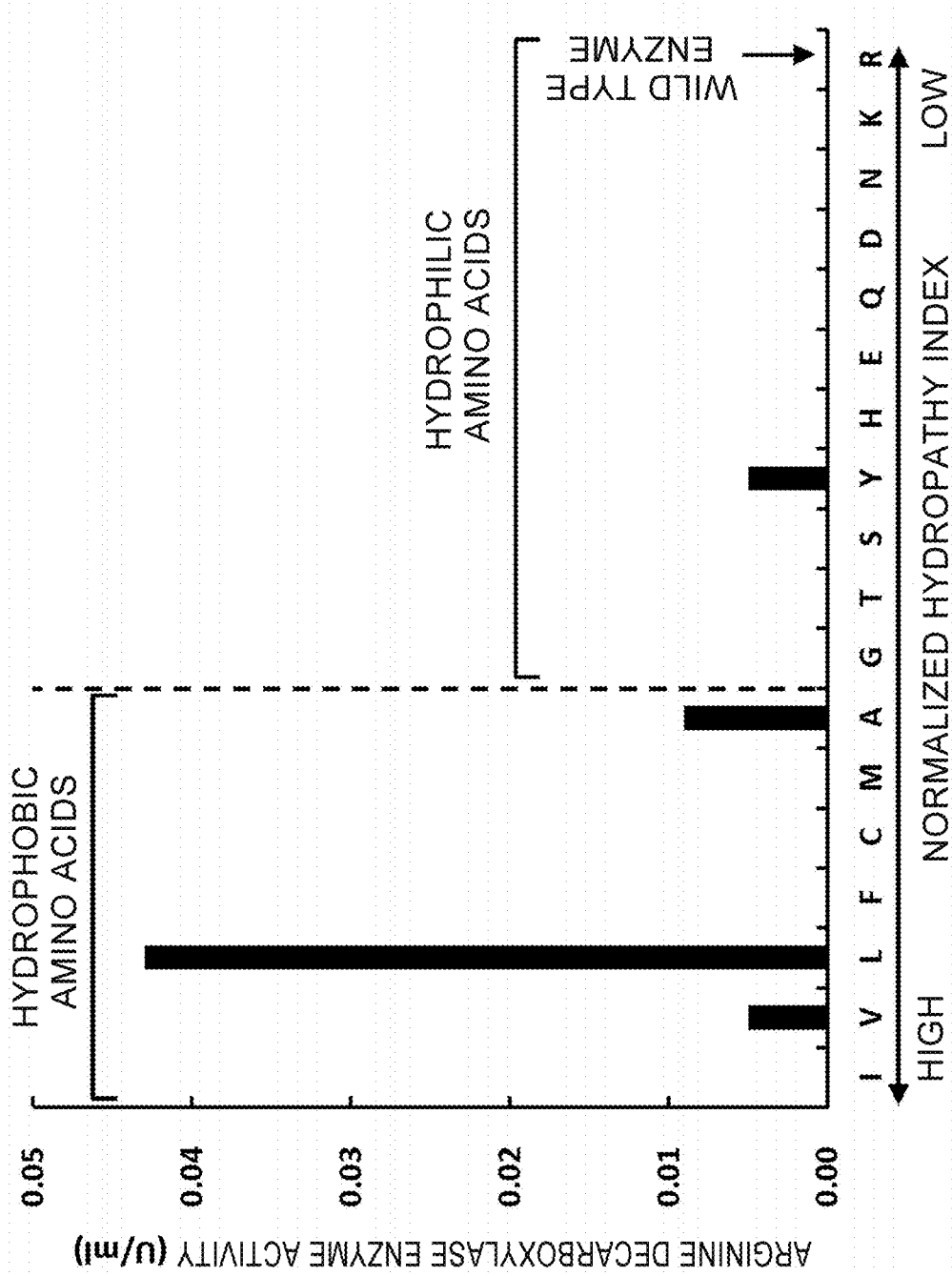
FIG. 9 shows decarboxylase activity (U/ml) and amino acid sequence conservation (%) of enzymes obtained by substituting arginine at the position 430 of arginine decarboxylase to other 19 amino acids; bars indicate oxidase activity and open circles show amino acid sequence conservation; and the letters are as follows: A: alanine, C: cysteine, D: aspartic acid, E: glutamic acid, F: phenylalanine, G: glycine, H: histidine, I: isoleucine, K: lysine, L: leucine, M: methionine, N: asparagine, P: proline, Q: glutamine, R: arginine, S: serine, T: threonine, V: valine, W: tryptophan and Y: tyrosine.

The active-form mutant arginine decarboxylases of the present invention in which arginine at the position 430 has been substituted to other amino acids respectively have, as shown in FIG. 9, arginine decarboxylase activity, while the native form has the enzyme activity that is substantially zero.

Figure 10:
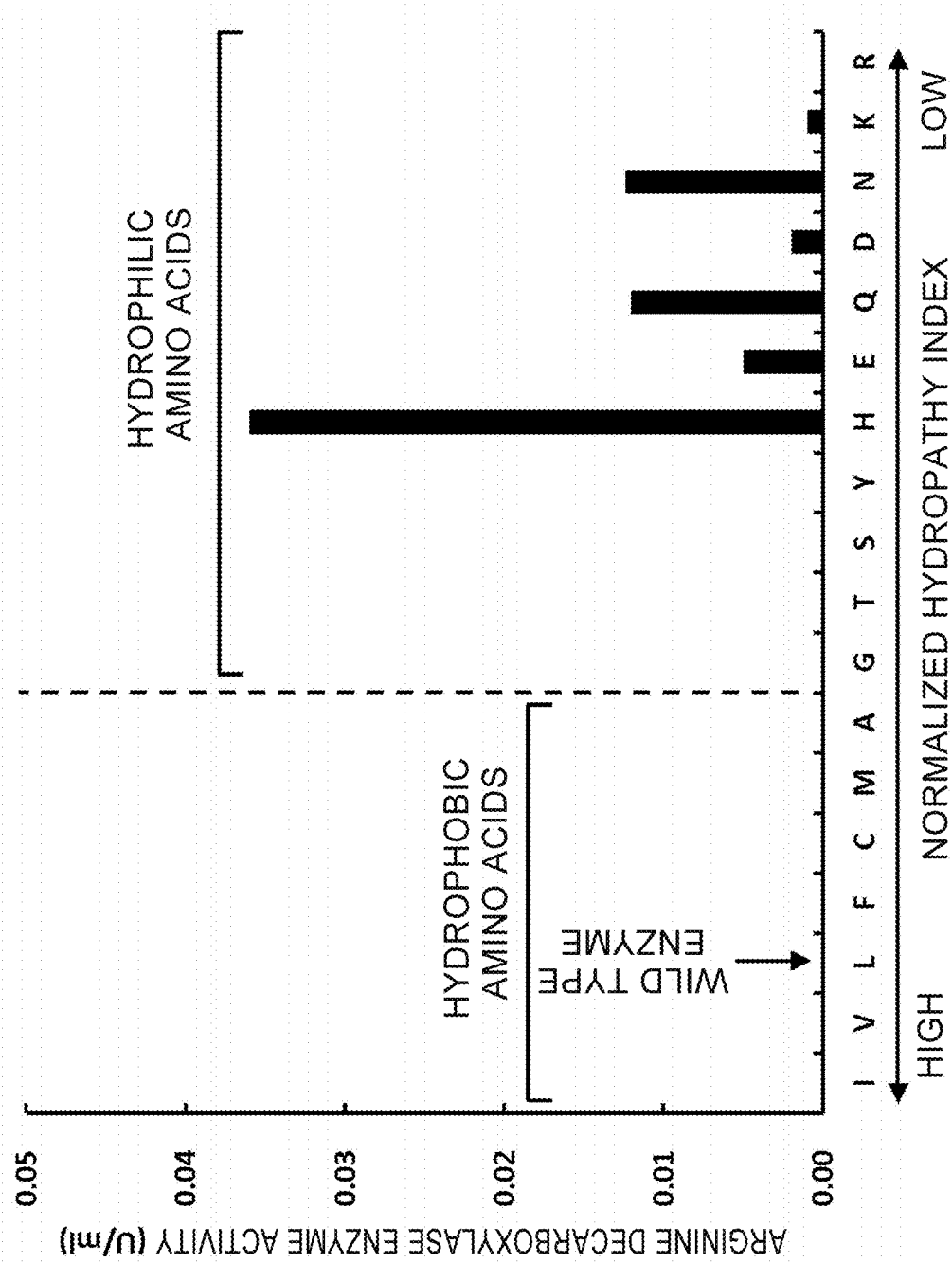
FIG. 10 shows decarboxylase activity (U/ml) and amino acid sequence conservation (%) of enzymes obtained by substituting leucine at the position 435 of arginine decarboxylase to other 19 amino acids; bars indicate oxidase activity and open circles show amino acid sequence conservation; and the letters are as follows: A: alanine, C: cysteine, D: aspartic acid, E: glutamic acid, F: phenylalanine, G: glycine, H: histidine, I: isoleucine, K: lysine, L: leucine, M: methionine, N: asparagine, P: proline, Q: glutamine, R: arginine, S: serine, T: threonine, V: valine, W: tryptophan and Y: tyrosine.

The active-form mutant arginine decarboxylases of the present invention in which leucine at the position 435 has been substituted to other amino acids respectively have, as shown in FIG. 10, arginine decarboxylase activity, while the native form has the enzyme activity that is substantially zero.

The active-form mutant ornithine decarboxylase of the present invention has an amino acid sequence shown in SEQ ID NO: 7, wherein:
lysine at the position 117 has been substituted to leucine and/or
leucine at the position 176 has been substituted to glutamic acid. The active-form mutant ornithine decarboxylase of the present invention encompasses an enzyme which is an active-form mutant enzyme and has an activity that is similar to or above the enzyme activity of the native form.

Specifically, although the enzyme activity of the native form could not be observed, the active-form mutant ornithine decarboxylases of the present invention in which lysine at the position 117 has been substituted to leucine and in which leucine at the position 176 has been substituted to glutamic acid in ornithine decarboxylase (DmODC) respectively had activity of 0.45 U/mL and 0.04 U/mL.

The active-form mutant luciferase of the present invention has an amino acid sequence shown in SEQ ID NO: 5, wherein:
isoleucine at the position 80 has been substituted to lysine and/or
alanine at the position 177 has been substituted to aspartic acid. The active-form mutant luciferase of the present invention encompasses an enzyme which is an active-form mutant enzyme and has an activity that is similar to or above the enzyme activity of the native form.

Figure 12:
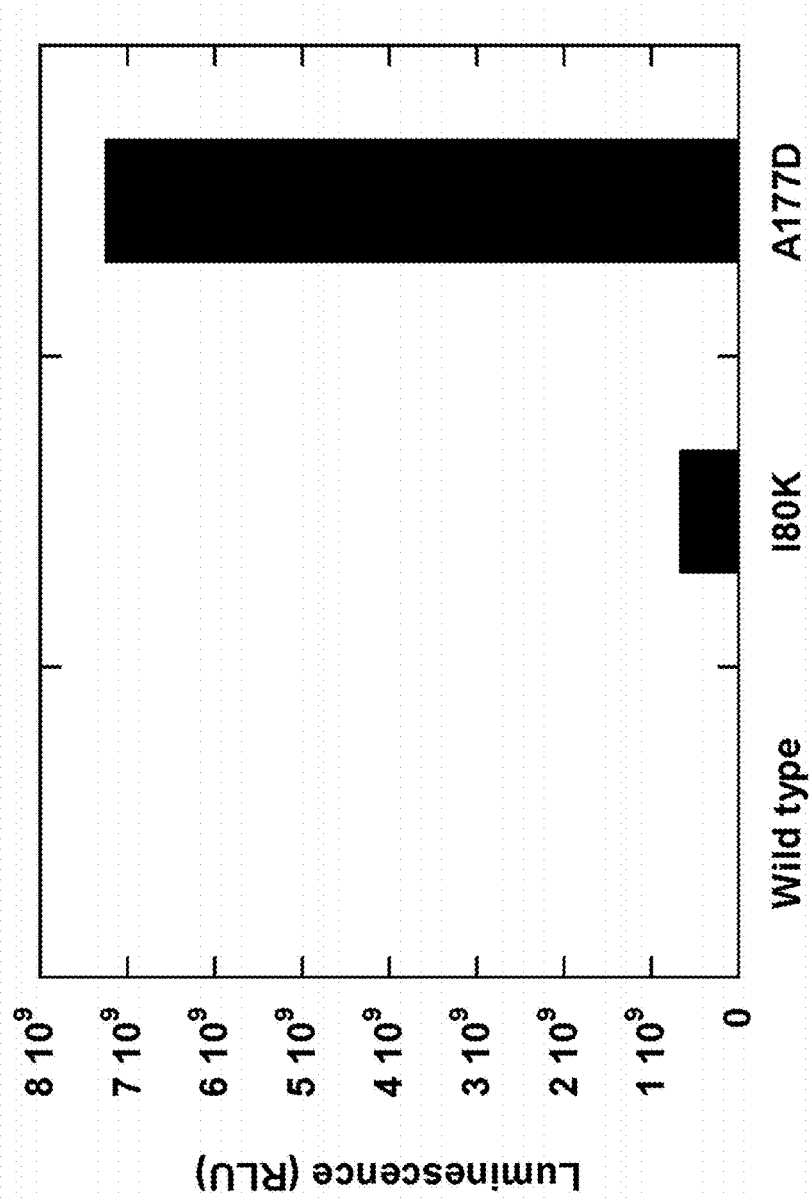
FIG. 12 shows the luminescence value of luciferase reaction of crude enzyme solutions of a wild type enzyme of luciferase, a mutant enzyme obtained by substituting isoleucine at the position 80 to lysine and a mutant enzyme obtained by substituting alanine at the position 177 to aspartic acid.

Specifically, the active-form mutant luciferase of the present invention in which isoleucine at the position 80 has been substituted to lysine and the active-form mutant luciferase (MpLUC) of the present invention in which alanine at the position 177 has been substituted to aspartic acid respectively have, as shown in FIG. 12, luciferase activity, while the native form has the enzyme activity that is substantially zero.

The active-form mutant glutamate dehydrogenase of the present invention has
an amino acid sequence shown in SEQ ID NO: 9, wherein:
valine at the position 174 has been substituted to aspartic acid,
lysine at the position 257 has been substituted to tyrosine and/or
leucine at the position 261 has been substituted to glutamic acid. The active-form mutant glutamate dehydrogenase of the present invention encompasses an enzyme which is an active-form mutant enzyme and has an activity that is similar to or above the enzyme activity of the native form.

Specifically, the active-form mutant glutamate dehydrogenases of the present invention in which valine at the position 174 has been substituted to aspartic acid, leucine at the position 257 has been substituted to tyrosine and leucine at the position 261 has been substituted to glutamic acid in glutamate dehydrogenase (DmGluDH) respectively had activity of 0.14 U/mL, 0.91 U/mL and 0.05 U/mL.

The present invention encompasses a method for producing an active-form mutant enzyme comprising expressing a gene that codes for the amino acid sequence of the active-form mutant enzyme of the present invention in an *E. coli* expression system to obtain a protein.

The active-form mutant enzyme is, for example, an active-form mutant mandelonitrile oxidase, an active-form mutant arginine decarboxylase, an active-form mutant ornithine decarboxylase, an active-form mutant luciferase or an active-form mutant glutamate dehydrogenase.

<Method for Producing a Soluble Mutant Protein (Producing Method of the Third Embodiment)>

The method for producing a soluble mutant protein of the present invention (producing method of the third embodiment) includes:

expressing, in a heterologous expression system, a gene having a base sequence that codes for an amino acid sequence in which:

at least one hydrophobic amino acid that is present in a hydrophilic domain of an α-helix structure region is substituted (to an amino acid with higher hydrophilicity or lower hydrophobicity than the amino acid to be substituted) and/or at least one hydrophilic amino acid that is present in a hydrophobic domain of the α-helix structure region is substituted (to an amino acid with higher hydrophobicity or lower hydrophilicity than the amino acid to be substituted), wherein the α-helix structure region is in an amino acid sequence of a protein of which native form is a soluble protein but which becomes insoluble when expressing a gene of the protein in a heterologous expression system (hereinafter "an insoluble-form protein); and selecting a protein (hereinafter "a soluble mutant protein") that is soluble.

The method for producing a soluble mutant protein of the present invention (producing method of the third embodiment) specifically includes the following steps:

(1) specifying a protein of which native form is a soluble protein but which becomes insoluble when expressing a gene of the protein in a heterologous expression system (hereinafter "an insoluble-form protein");

(2a) specifying an α-helix structure region of the insoluble-form protein specified in step (1), specifying a hydrophilic domain and/or hydrophobic domain of the specified α-helix structure region, and specifying a hydrophobic amino acid that is present in the hydrophilic domain and/or a hydrophilic amino acid that is present in the hydrophobic domain;

(3a) preparing a gene having a base sequence that codes for an amino acid sequence in which at least one hydrophobic amino acid that is present in the hydrophilic domain of the α-helix structure region in the amino acid sequence of the insoluble-form protein is substituted (to an amino acid with higher hydrophilicity or lower hydrophobicity than the amino acid to be substituted) and/or at least one hydrophilic amino acid that is present in the hydrophobic domain of the α-helix structure region is substituted (to an amino acid with higher hydrophobicity or lower hydrophilicity than the amino acid to be substituted); and (4a) expressing, in a heterologous expression system, the gene having the base sequence prepared in step (3a) to obtain a protein and selecting from the obtained proteins, a protein (hereinafter "a soluble mutant protein") that is soluble.

The method for producing a soluble mutant protein of the present invention (producing method of the third embodiment) may be carried out by substituting the inactive-form enzyme to the insoluble-form protein and the active-form mutant enzyme to the soluble mutant protein in the method for producing an active-form mutant enzyme of the present invention (producing method of the first embodiment).

<Method for Producing a Soluble Mutant Protein (Producing Method of the Fourth Embodiment)>

The method for producing a soluble mutant protein of the present invention (producing method of the fourth embodiment) includes expressing, in a heterologous expression system, a gene having a base sequence that codes for an amino acid sequence of a protein of which native form is a soluble protein but which becomes insoluble when expressing a gene of the protein in a heterologous expression system ("an insoluble-form protein"), wherein in the amino acid sequence, at least one amino acid with relatively low conservation is substituted to an amino acid with higher conservation than said amino acid; and obtaining a protein ("a soluble mutant protein") that is soluble.

The method for producing a soluble mutant protein of the present invention (producing method of the fourth embodiment) specifically includes the following steps:

(1) specifying a protein of which native form is a soluble protein but which becomes insoluble when expressing a gene of the protein in a heterologous expression system ("an insoluble-form protein");

(2b) determining a conservation in sequence identity of at least some amino acids in an amino acid sequence of the insoluble-form protein specified in step (1) and specifying an amino acid with relatively low conservation;

(3b) preparing a gene having a base sequence that codes for an amino acid sequence in which at least one amino acid with relatively low conservation is substituted to an amino acid with higher conservation than said amino acid; and (4b) expressing, in a heterologous expression system, the gene having the base sequence prepared in step (3b) to obtain a protein and selecting from the obtained proteins, a soluble mutant protein.

The method for producing a soluble mutant protein of the present invention (producing method of the fourth embodiment) may be carried out by substituting the inactive-form enzyme to the insoluble-form protein and the active-form mutant enzyme to the soluble mutant protein in the method for producing an active-form mutant enzyme of the present invention (producing method of the second embodiment).

Similar to the method of the first embodiment and the method of the second embodiment for producing an active-form mutant enzyme of the present invention, the method for producing a soluble mutant protein of the present invention (producing method of the third embodiment) and the method for producing a soluble mutant protein of the present invention (producing method of the fourth embodiment) may be combined.

In the method for producing a soluble mutant protein of the present invention (producing methods of the third and fourth embodiments), being a soluble mutant protein may be judged from, for example, a soluble protein amount in an extract after heterologous expression. Further, the soluble mutant protein may be defined as a mutant protein of which the soluble protein amount in the extract after heterologous expression is higher than the soluble protein amount in an extract after heterologous expression of the native form protein. The soluble protein amount means the amount of the soluble protein excluding other soluble proteins that are present in the extract. The extract after heterologous expression may be, as a solution, a buffered aqueous solution without any surfactant and extraction may be carried out by physically or mechanically disrupting (for example, ultrasonication, grinding, French press) the host (cells) used for heterologous expression in the presence of the buffered aqueous solution. The extract may contain, in addition to the soluble mutant protein, an insoluble protein and in this case, the extract is centrifuged to obtain the soluble mutant protein in a supernatant. The soluble mutant protein in a supernatant may be assayed by a well-known protein assay, examples of which may include electrophoresis, ELISA, western blotting and the like.

The insoluble-form protein in the present invention is a protein of which native form is a soluble protein but which becomes insoluble in a heterologous expression system when expressing a gene of the protein in the heterologous expression system. As examples of the heterologous expression system, the description in the method for producing an active-form mutant enzyme of the present invention (producing method of the first embodiment) may be referred to. Examples of the insoluble-form protein may include one protein selected from the group consisting of an enzyme, a cytokine, a haemoglobin and a myoglobin. Although not all cytokines, haemoglobins and myoglobins are insoluble-form proteins in the present invention, some of them are insoluble-form proteins in the present invention. As the insoluble-form protein in the present invention, one protein selected from the group consisting of IFN-γ, IL-2, IFN and human growth hormone may be more specifically mentioned. By referring to the following references, it is found that some of the proteins are insoluble-form proteins of the present invention.

Human growth hormone (Fibroblast growth factor 15): PLoS ONE, 6, e20307 (2011), Interleukin-6 (IL-6): J. Vet. Med. Sci., 66, pp. 1053-1057, (2004)

The present invention is hereinafter described in further detail by way of Examples. However, Examples merely exemplify the present invention and it is not intended to limit the present invention to Examples.

Example 1

Expression of Mandelonitrile Oxidase Derived from *Chamberlinius hualinensis* (ChMOX) as an Active-Form Mutant Enzyme (1) Mutagenesis of a Mandelonitrile Oxidase Gene A mandelonitrile oxidase gene derived from *Chamberlinius hualinensis* (SEQ ID NO: 1) was introduced to an *E. coli* expression vector pET22b to prepare "pET22b-ChMOX". An aqueous solution of pColdI-ChMOX (5 µL) was introduced into *E. coli* XL-1 Red (manufactured by Agilent Technologies) by heat shock for transformation. The cells were cultured in LB medium containing 100 rig/mL of ampicillin for 48 hours, and the colonies thus grown were suspended in a 100 mM potassium phosphate buffer (pH 7.0) by using a bacteria spreader to collect the cells. The plasmid vector was extracted to obtain a mutant enzyme library.

(2) Selection of an Active-Form Mutant Enzyme Expression Plasmid Vector from the Mutant Mandelonitrile Oxidase Library The mutant enzyme library obtained in (1) was introduced into *E. coli* BL21 (DE3) by heat shock under the same conditions as in (1) for transformation. Colonies grown on LB agar medium containing 100 µg/mL of ampicillin were cultured in wells of a 96-well deep well plate containing 300 µL of LB medium containing 100 µg/mL of ampicillin at 37° C., 0.5 µg/mL of IPTG was added at a cell turbidity of about 0.5 and the cells were cultured at 30° C. for 6 hours. After collecting the cells by centrifugation (2000×g, 15 minutes, 4° C.), 50 µL of a cell lysis reagent BugBuster (manufactured by Novagen) was added and the mixture was shaken at room temperature for about 15 minutes. A 10 mM potassium phosphate buffer (pH 7.0, 150 µL) was then added and a supernatant was obtained by centrifugation (2000×g, 15 minutes, 4° C.) to give a crude enzyme solution. By referring to PTL 10, the crude enzyme solution was measured for mandelonitrile oxidase activity. The mutant enzyme which exhibited the activity was sequenced for the DNA sequence on a DNA sequencer. As a result, it was found that valine at the position 455 was substituted to alanine.

(3) Saturation Mutation of the Amino Acid at the Position 455 in Mandelonitrile Oxidase Mutant mandelonitrile oxidase expression plasmids were constructed in which valine at the position 455 was substituted to other 19 amino acids. Each plasmid was cultured under the same conditions as in (1) and the mandelonitrile oxidase activity was assayed. As a result, it was found that, as shown in FIG. 4, the activity was high when the substituting amino acid had lower hydropathy index, namely higher hydrophilicity than valine and the mandelonitrile oxidase activity was particularly high for hydrophilic amino acids (E, Q, D, N, K and R).

(4) Analysis Using Secondary Structure Prediction and Helical Wheel

As a result of prediction on a secondary structure predicting programme PSIPRED (http://bioinf.cs.ucl.ac.uk/psipred/) of the amino acid sequence of mandelonitrile oxidase (SEQ ID NO: 2), it was revealed that valine at the mutation site, the position 455, was present in the amino acid sequence (RVDIDTMVRGVHVALNFG) of an α-helix structure (FIG. 1A). In addition, as a result of drawing a helical wheel on pepwheel (http://emboss.bioinformatics.nl/cgi-bin/emboss/pepwheel), valine at the position 455 was, as shown in FIG. 1B, a hydrophobic amino acid that was present in a hydrophilic domain. It was revealed that substitution of valine at the position 455 to alanine was introduction of a mutation in an α-helix and further a mutation to an amino acid with low hydropathy index, namely high hydrophilicity that was present in a hydrophilic domain.

(5) Introduction of Saturation Mutation of Valine at the Position 444

Figure 6:
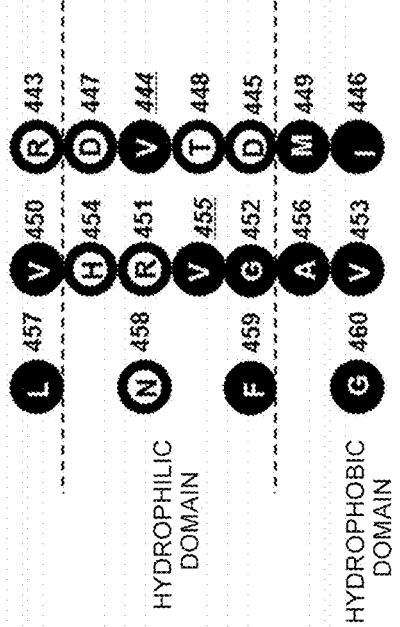
FIG. 6A shows a helical wheel obtained with R443 to G460 of mandelonitrile oxidase according to the drawing method shown in FIG. 2 (secondary structure predicting method)
FIG. 6B is a linear representation of the helical wheel in FIG. 6A.
FIG. 6C shows the linear representation of the helical wheel together with the hydropathy index of each amino acid and the sum of each row.
Figure 1:
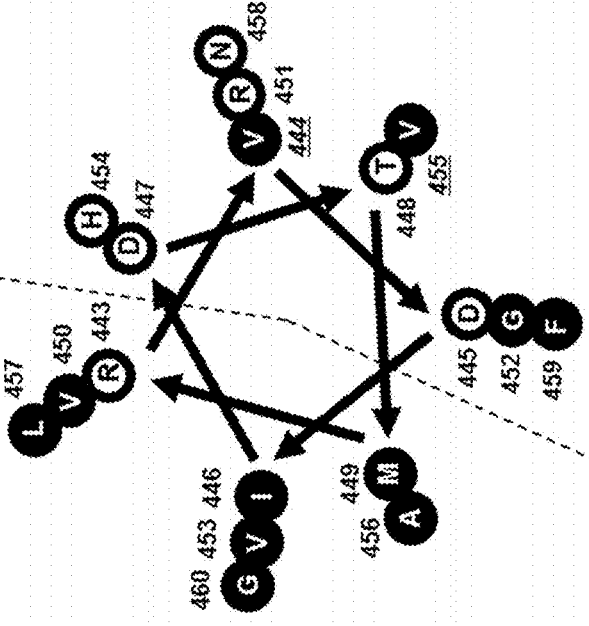
Figures 2, 6:
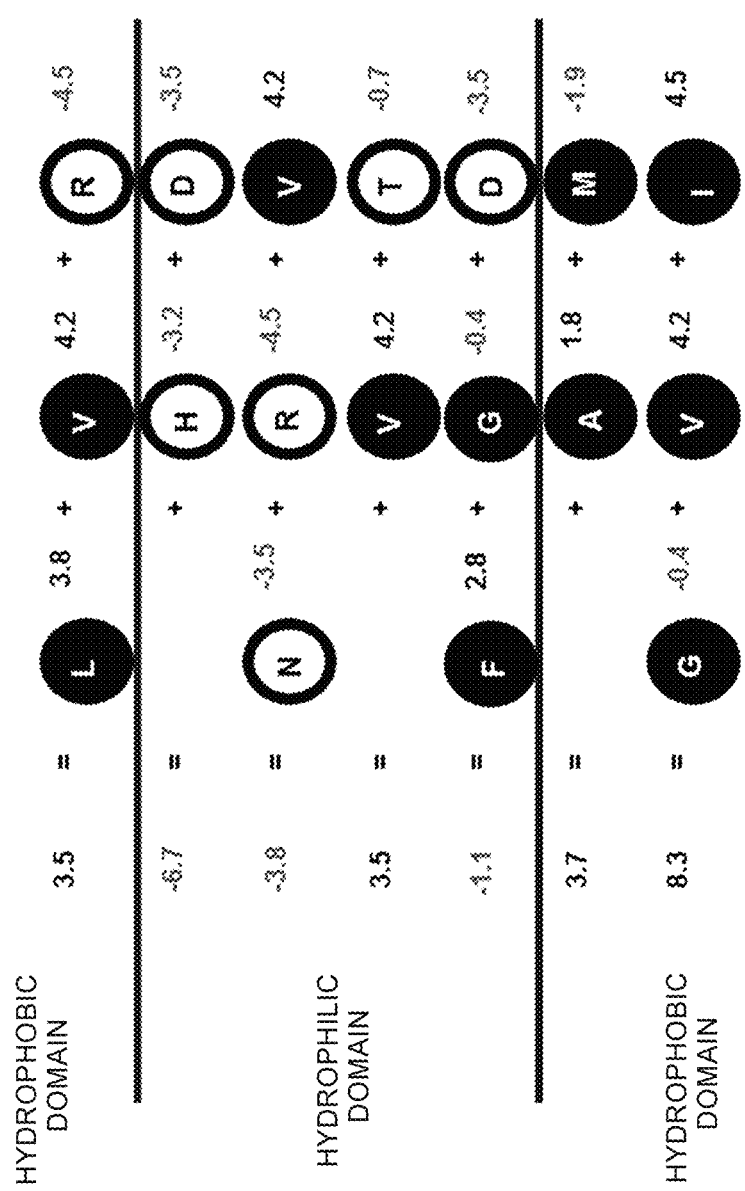
FIG. 2 is a helical wheel projection (left panel) and the sequences obtained by aligning amino acids 1 to 18 in an amino acid sequence on the helical wheel projection in a clockwise manner (A) and amino acid sequences on the helix obtained by beginning new rows every 7 residues and hydrophilic and hydrophobic domains therein (B); the helical wheel is believed to have 3.6 residues per period, the eighth residue returns to the position close to the first residue and the rest of the residues describe a similar trajectory; an open circle represents a hydrophilic amino acid and a filled circle represents a hydrophobic amino acid; and as apparent from the left panel, the domain containing hydrophilic amino acids 2, 5, 6, 12, 13 and 16 is taken as a hydrophilic domain, the domain containing hydrophobic amino acids 1, 3, 4, 7, 8, 10, 14, 15, 17 and 18 is taken as a hydrophobic domain and it is considered that hydrophobic amino acid 9 in the hydrophilic domain and hydrophilic amino acid 11 in the hydrophobic domain are the sites at which mutations are introduced.

As, similar to valine at the position 455, V444, G452 and F459 are also "hydrophobic amino acids that are present in a hydrophilic domain" of an α-helix, mutations were introduced at V444, G452 and F459 by using QuikChange Site-Directed Mutagenesis Kit (manufactured by Agilent Technologies) so that the sites were substituted to other 19 amino acids. *E. coli* JM109 (DE3) was transformed with each of the obtained mutagenized plasmids, inoculated to LB plates containing ampicillin and cultured at 37° C. for 16 hours. The plasmids harboured by the obtained colonies were sequenced and mutant mandelonitrile oxidase expression plasmids were constructed in which V444, G452 and F459 were substituted to other 19 amino acids. Each plasmid was cultured under the same conditions as in (1) and the mandelonitrile oxidase activity was assayed. It was revealed that mutations at V444 to amino acids with low hydropathy index, namely high hydrophilicity were correlated to expression of active-form enzymes. Activity was not exhibited by amino acid substitutions to other 19 amino acids at G452 or F459. From the result shown in FIG. 6 obtained by re-drawing a helical wheel according to the drawing manner shown in FIG. 2, it was found that the two residues are present at the border between a hydrophilic domain and a hydrophobic domain as shown in FIG. 6C, and thus it was believed that the drawing manner shown in FIG. 2 was suitable for dividing the regions.

(6) Sequence Conservation at V444, G452, V455 and F459

Homology was searched on BLAST (http://blast.ncbi.nlm.nih.gov/Blast.cgi?PROGRAM=blastp&PAGE_TYPE=BlastSearch&LINK_LOC=blasthome) and the sequence conservation of the α-helix sequence was calculated on INTMSAlign (NPL 7). The sequence conservation was calculated under the following conditions. The sequence of the inactive-form enzyme is entered in the section "Sequence" on the BLAST site, 5000 is selected as the value of "Max target sequences" of the "General Parameters" under the "Algorithm parameters" section below and 1.0E-3 is entered as the value of "Expect threshold" and then the BLAST search is started, thereby other proteins with high identity are selected. By downloading all the obtained protein sequences having high identity in FASTA format and entering the sequences to INTMSAlign, sequence conservation was calculated.

The results of conservation of V444, G452, V455 and F459 are shown in Table 2. It was found that at V444 and V455, relatively, not only hydrophobic amino acids but also hydrophilic amino acids were frequently conserved, while at G452 and F459, amino acids with similar hydropathy index were conserved.

According to the above, it was suggested that when, particularly, a hydrophilic amino acid is conserved at a hydrophobic amino acid in a hydrophilic domain, expression of an active-form mutant enzyme is facilitated by substituting the hydrophobic amino acid to a hydrophilic amino acid.

An arginine decarboxylase gene derived from *Arabidopsis thaliana* (SEQ ID NO: 4) was introduced to pET11a to prepare "pET11α-AtArgDC". Mutations were introduced by using QuikChange Site-Directed Mutagenesis Kit (manufactured by Agilent Technologies) so that the residues described in (1) were substituted to other amino acids. *E. coli* JM109 (DE3) was transformed with each of the obtained mutagenized plasmids, inoculated to LB plates containing ampicillin and cultured at 37° C. for 16 hours. The plasmids harboured by the obtained colonies were sequenced and mutant arginine decarboxylase expression plasmids were constructed in which V261, L264, R430, L435 and K441 were substituted to other 19 amino acids. Each plasmid was cultured under the same conditions as above and the arginine decarboxylase activity was assayed. It was revealed that mutations at V261 (FIG. 8) and L435 (FIG. 9) to amino acids with low hydropathy index, namely high hydrophilicity and at R430 (FIG. 10) to amino acids with high hydropathy index, namely high hydrophobicity were correlated to expression of active-form mutant enzymes. Introduction of combined mutations of the above increased the activity, and thus an increase of the production of active-form mutant enzymes by accumulation of mutations was observed. However, activity was not exhibited by amino acid substitutions to other 19 amino acids at L264 or K441.

(3) Sequence conservation at V261, L264, R430, L435 and K441

Homology was searched on BLAST and the sequence conservation of the α-helix sequences was calculated on INTMSAlign (NPL 7). The sequence conservation was calculated under the following conditions. The sequence of

TABLE 2

Conservation of amino acids at V444, G452, V455 and F459

| Residue | I | V | L | F | C | M | A | G | T | W | S | Y | P | H | E | Q | D | N | K | R | Non |
|---|---|---|---|---|---|---|---|---|---|---|---|---|---|---|---|---|---|---|---|---|---|
| V444 | 1.4 | 0.7 | 3.1 | 1.7 | 0.0 | 0.6 | 4.3 | 0.5 | 2.9 | 0.2 | 1.8 | 4.2 | 0.1 | 2.3 | 8.8 | 4.5 | 6.9 | 0.8 | 2.3 | 5.8 | 47.0 |
| G452 | 0.2 | 0.5 | 0.2 | 0.1 | 18.3 | 0.5 | 17.1 | 57.2 | 0.5 | 0.0 | 4.0 | 0.2 | 0.0 | 0.1 | 0.0 | 0.1 | 0.0 | 0.0 | 0.3 | 0.1 | 0.6 |
| V455 | 17.8 | 3.3 | 41.5 | 7.0 | 0.3 | 6.4 | 5.2 | 0.0 | 2.4 | 0.9 | 0.4 | 1.4 | 0.1 | 1.1 | 1.9 | 2.5 | 0.1 | 0.1 | 4.6 | 2.6 | 0.2 |
| F459 | 64.4 | 7.5 | 21.8 | 0.7 | 0.0 | 3.2 | 0.4 | 0.0 | 0.2 | 0.1 | 0.1 | 0.1 | 0.0 | 0.0 | 0.1 | 0.1 | 0.1 | 0.1 | 0.1 | 0.1 | 1.0 |

Example 2

Figures 2, 7:
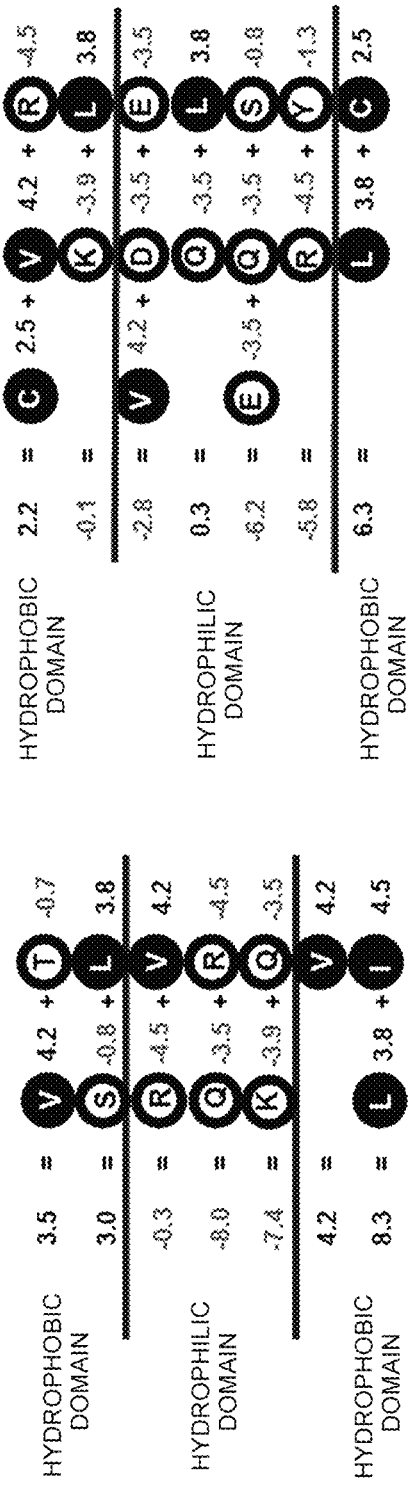

Expression of Arginine Decarboxylase Derived from *Arabidopsis thaliana* (AtADC) as an Active-Form Mutant Enzyme (1) Estimation of α-Helices by a Secondary Structure Predicting Programme and Drawing of a Helical Wheel The amino acid sequence of arginine decarboxylase derived from *Arabidopsis thaliana* (SEQ ID NO: 3) was analysed with the secondary structure predicting programme PSIPRED as described above and, as a result, it was estimated that the enzyme had 20 α-helices (FIG. 7A). By drawing helical wheels by using all sequences of the α-helices as described above, it was revealed that valine at the position 261, leucine at the position of 264, arginine at the position of 430, leucine at the position of 435 and lysine at the position of 441 in the 8th (TVQILRWRKLSQ) and 13th (RESCLLYVDQLKQRCVE) α-helices from the N-terminal were, as shown in FIGS. 7B and 7C, "a hydrophobic amino acid that is present in a hydrophilic domain" or "a hydrophilic amino acid that is present in a hydrophobic domain".

(2) Mutagenesis at V261, L264, R430, L435 and K441 of Arginine Decarboxylase the inactive-form enzyme is entered in the section "Sequence" on the BLAST site, 5000 is selected as the value of "Max target sequences" of the "General Parameters" under the "Algorithm parameters" section below and 1.0E-3 is entered as the value of "Expect threshold" and then the BLAST search is started, thereby other proteins with high identity are selected. By downloading all the obtained protein sequences having high identity in FASTA format and entering the sequences to INTMSAlign, sequence conservation was calculated.

The results of conservation of V261, L264, R430, L435 and K441 are shown in Table 3. It was found that at V261 and L435, relatively, not only hydrophobic amino acids but also hydrophilic amino acids were frequently conserved and at R430, relatively, not only hydrophilic amino acids but also hydrophobic amino acids were frequently conserved. However, at L264 and K441, it was found that amino acids with similar hydropathy index were conserved.

According to the above, it was suggested that an amino acid particularly having the same characteristics as the region is conserved when at a hydrophobic amino acid in a hydrophilic domain or a hydrophilic amino acid in a hydrophobic domain, expression of an active-form mutant enzyme is facilitated by substituting such an amino acid.

TABLE 3

Conservation of amino acids at V261, L264, R430, L435 and K441

| Residue | I | V | L | F | C | M | A | G | T | W | S | Y | P | H | E | Q | D | N | K | R | Non |
|---|---|---|---|---|---|---|---|---|---|---|---|---|---|---|---|---|---|---|---|---|---|
| V261 | 4.4 | 0.3 | 2.4 | 1.7 | 0.0 | 0.8 | 13.3 | 1.3 | 21.6 | 0.5 | 16.4 | 0.9 | 5.4 | 0.9 | 5.6 | 0.7 | 5.8 | 3.8 | 6.7 | 3.4 | 4.0 |
| L264 | 8.2 | 10.1 | 49.9 | 0.6 | 0.0 | 2.8 | 12.9 | 1.5 | 0.3 | 0.0 | 0.5 | 1.0 | 1.1 | 0.1 | 1.7 | 1.1 | 0.7 | 1.0 | 0.3 | 0.6 | 5.5 |
| R430 | 2.5 | 5.0 | 23.8 | 1.5 | 0.5 | 3.8 | 9.2 | 1.1 | 0.6 | 0.7 | 1.2 | 6.8 | 1.8 | 1.3 | 1.5 | 1.7 | 0.9 | 1.0 | 0.9 | 1.2 | 33.1 |
| L435 | 1.4 | 1.4 | 4.5 | 0.7 | 0.3 | 1.3 | 1.1 | 0.6 | 1.2 | 3.4 | 1.0 | 2.0 | 0.9 | 30.7 | 1.7 | 2.9 | 1.8 | 9.3 | 0.6 | 0.9 | 32.3 |
| K441 | 2.9 | 2.6 | 21.0 | 1.8 | 0.5 | 5.1 | 1.5 | 1.4 | 3.4 | 0.4 | 1.0 | 0.5 | 0.8 | 3.3 | 0.9 | 1.2 | 1.0 | 0.8 | 10.8 | 8.1 | 31.1 |

Example 3

Figure 11:
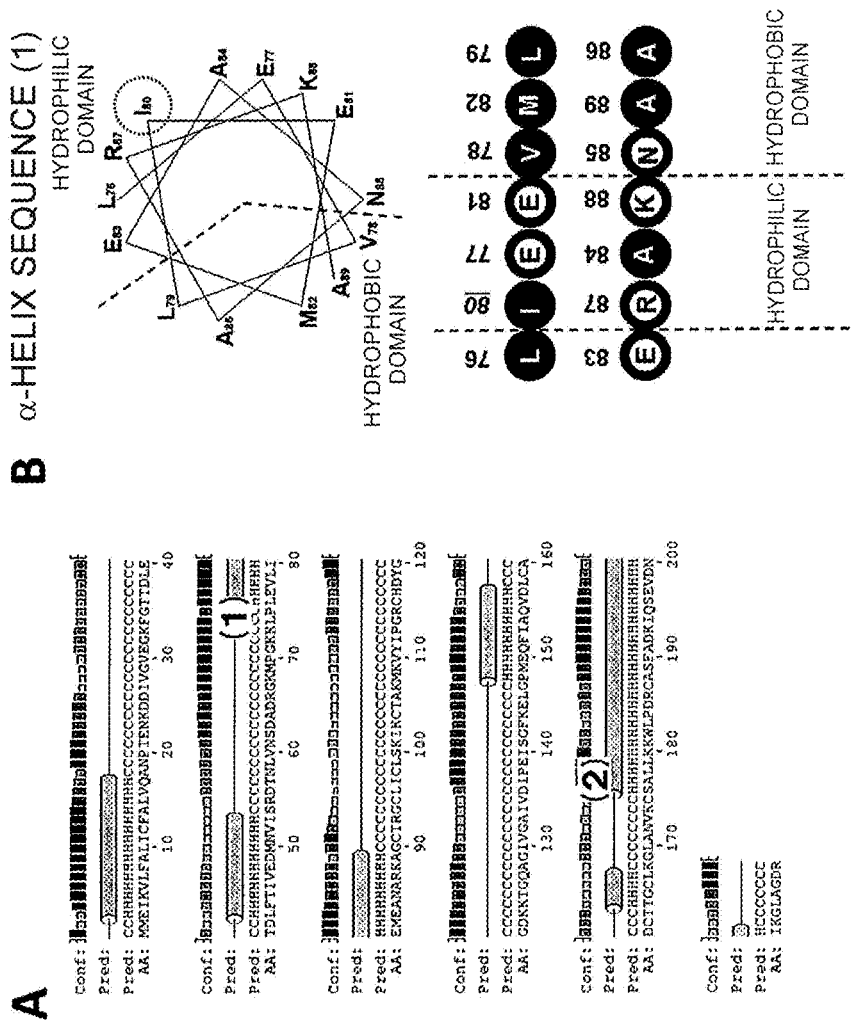
FIG. 11 shows a secondary structure predicted for the amino acid sequence of luciferase (A) and a helical wheel of α-helix (1) (B, upper panel) and hydrophilic and hydrophobic domains and the mutation site (B, lower panel).

Expression of Luciferase Derived from *Metridia pacifica* (MpLUC) as an Active-Form Mutant Enzyme (1) Estimation of α-Helices by a Secondary Structure Predicting Programme As a result of prediction of a secondary structure of the amino acid sequence (SEQ ID NO: 5) of luciferase (MpLUC) 1-1 derived from marine plankton, *Metridia pacifica*, with the same programme as above (FIG. 11), it was found that as shown in FIG. 11A, MpLUC 1-1 had 6 α-helix structures and the α-helix sequence indicated with (1) could be divided into the hydrophilic domain and the hydrophobic domain based on the helical wheel prepared (FIG. 11B). However, the α-helix sequence indicated with (2) could not be divided into a hydrophilic domain and a hydrophobic domain based on the helical wheel prepared. For α-helix sequences (1) and (2), homology was searched on BLAST and the sequence conservation of the α-helix sequences was calculated on INTMSAlign (NPL 7). The sequence conservation was calculated under the following conditions. The sequence of the inactive-form enzyme is entered in the section "Sequence" on the BLAST site, 5000 is selected as the value of "Max target sequences" of the "General Parameters" under the "Algorithm parameters" section below and 1.0E-3 is entered as the value of "Expect threshold" and then the BLAST search is started, thereby other proteins with high identity are selected. By downloading all the obtained protein sequences having high identity in FASTA format and entering the sequences to INTMSAlign, sequence conservation was calculated.

As a result, isoleucine at the position 80 and alanine at the position 177 were found to be amino acids with low conservation and it was also revealed that lysine and aspartic acid were conserved with high percentages at the former and latter amino acids, respectively.

TABLE 4

Sequence conservation at L76 to A89 of MpLUC

| Residue | I | V | L | F | C | M | A | G | T | W | S | Y | P | H | E | Q | D | N | K | R | Non |
|---|---|---|---|---|---|---|---|---|---|---|---|---|---|---|---|---|---|---|---|---|---|
| L76 | 5.4 | 2.7 | 59.2 | 0.0 | 0.0 | 0.0 | 0.0 | 0.0 | 0.0 | 0.0 | 0.0 | 0.0 | 8.3 | 0.0 | 0.0 | 0.0 | 0.0 | 0.0 | 22.1 | 0.0 | 2.3 |
| E77 | 0.0 | 0.0 | 0.0 | 0.0 | 0.0 | 0.0 | 27.5 | 0.0 | 0.0 | 0.0 | 0.0 | 0.0 | 0.0 | 0.0 | 62.0 | 0.0 | 8.3 | 0.0 | 0.0 | 0.0 | 2.2 |
| V78 | 2.7 | 86.5 | 8.6 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 2.2 |
| L79 | 2.7 | 0.0 | 92.7 | 0.0 | 0.0 | 2.4 | 0.0 | 0.0 | 0.0 | 0.0 | 0.0 | 0.0 | 0.0 | 0.0 | 0.0 | 0.0 | 0.0 | 0.0 | 0.0 | 0.0 | 2.2 |
| I80 | 14.6 | 5.3 | 3.1 | 0.0 | 0.0 | 5.1 | 11.3 | 0.0 | 0.0 | 0.0 | 0.0 | 0.0 | 0.0 | 0.0 | 0.0 | 0.0 | 6.1 | 0.0 | 50.2 | 2.2 | 2.1 |
| E81 | 12.9 | 0.0 | 0.0 | 0.0 | 0.0 | 0.0 | 0.0 | 0.0 | 0.0 | 0.0 | 0.0 | 0.0 | 0.0 | 0.0 | 84.9 | 0.0 | 0.0 | 0.0 | 0.0 | 0.0 | 2.2 |
| M82 | 0.0 | 0.0 | 2.2 | 0.0 | 0.0 | 95.6 | 0.0 | 0.0 | 0.0 | 0.0 | 0.0 | 0.0 | 0.0 | 0.0 | 0.0 | 0.0 | 0.0 | 0.0 | 0.0 | 0.0 | 2.2 |
| E83 | 0.0 | 0.0 | 0.0 | 0.0 | 0.0 | 0.0 | 0.0 | 0.0 | 0.0 | 0.0 | 0.0 | 0.0 | 0.0 | 0.0 | 8.6 | 89.3 | 0.0 | 0.0 | 0.0 | 0.0 | 2.1 |
| A84 | 0.0 | 0.0 | 0.0 | 0.0 | 6.1 | 0.0 | 91.7 | 0.0 | 0.0 | 0.0 | 0.0 | 0.0 | 0.0 | 0.0 | 0.0 | 0.0 | 0.0 | 0.0 | 0.0 | 0.0 | 2.2 |
| N85 | 8.6 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 89.3 | 0.0 | 0.0 | 2.1 |
| A86 | 0.0 | 0.0 | 0.0 | 0.0 | 0.0 | 0.0 | 97.8 | 0.0 | 0.0 | 0.0 | 0.0 | 0.0 | 0.0 | 0.0 | 0.0 | 0.0 | 0.0 | 0.0 | 0.0 | 0.0 | 2.2 |
| R87 | 0.0 | 11.3 | 0.0 | 10.6 | 0.0 | 0.0 | 3.1 | 0.0 | 0.0 | 0.0 | 5.8 | 0.0 | 0.0 | 0.0 | 0.0 | 5.5 | 0.0 | 0.0 | 20.0 | 41.4 | 2.3 |
| K88 | 0.0 | 0.0 | 0.0 | 0.0 | 0.0 | 0.0 | 0.0 | 0.0 | 0.0 | 0.0 | 0.0 | 0.0 | 0.0 | 0.0 | 2.4 | 0.0 | 0.0 | 8.6 | 51.5 | 35.4 | 2.1 |
| A89 | 0.0 | 0.0 | 0.0 | 0.0 | 0.0 | 0.0 | 89.0 | 0.0 | 0.0 | 0.0 | 8.8 | 0.0 | 0.0 | 0.0 | 0.0 | 0.0 | 0.0 | 0.0 | 0.0 | 0.0 | 2.2 |

TABLE 5

Sequence conservation at S176 to I201 of MpLUC

| Residue | I | V | L | F | C | M | A | G | T | W | S | Y |
|---|---|---|---|---|---|---|---|---|---|---|---|---|
| S176 | 0.0 | 0.0 | 0.0 | 0.0 | 0.0 | 0.0 | 0.0 | 0.0 | 0.0 | 0.0 | 84.9 | 0.0 |
| A177 | 0.0 | 0.0 | 0.0 | 0.0 | 0.0 | 0.0 | 6.1 | 0.0 | 23.4 | 0.0 | 0.0 | 0.0 |
| L178 | 0.0 | 0.0 | 77.4 | 0.0 | 0.0 | 0.0 | 11.3 | 0.0 | 0.0 | 0.0 | 0.0 | 0.0 |
| L179 | 0.0 | 0.0 | 100.0 | 0.0 | 0.0 | 0.0 | 0.0 | 0.0 | 0.0 | 0.0 | 0.0 | 0.0 |
| K180 | 0.0 | 0.0 | 0.0 | 5.3 | 0.0 | 0.0 | 0.0 | 0.0 | 0.0 | 0.0 | 0.0 | 6.1 |
| K181 | 0.0 | 0.0 | 0.0 | 0.0 | 0.0 | 0.0 | 0.0 | 8.6 | 0.0 | 0.0 | 0.0 | 0.0 |
| W182 | 0.0 | 2.7 | 0.0 | 0.0 | 0.0 | 0.0 | 13.8 | 0.0 | 0.0 | 83.5 | 0.0 | 0.0 |
| L183 | 0.0 | 0.0 | 97.6 | 0.0 | 0.0 | 2.4 | 0.0 | 0.0 | 0.0 | 0.0 | 0.0 | 0.0 |
| P184 | 0.0 | 0.0 | 0.0 | 0.0 | 0.0 | 0.0 | 0.0 | 0.0 | 0.0 | 0.0 | 0.0 | 0.0 |
| D185 | 0.0 | 0.0 | 0.0 | 0.0 | 0.0 | 0.0 | 2.7 | 2.4 | 11.6 | 0.0 | 14.2 | 0.0 |
| R186 | 0.0 | 0.0 | 0.0 | 0.0 | 0.0 | 0.0 | 0.0 | 0.0 | 0.0 | 0.0 | 0.0 | 0.0 |
| C187 | 0.0 | 0.0 | 0.0 | 0.0 | 100.0 | 0.0 | 0.0 | 0.0 | 0.0 | 0.0 | 0.0 | 0.0 |
| A188 | 0.0 | 0.0 | 0.0 | 0.0 | 0.0 | 0.0 | 49.8 | 0.0 | 22.7 | 0.0 | 8.1 | 0.0 |
| S189 | 0.0 | 0.0 | 0.0 | 0.0 | 0.0 | 0.0 | 0.0 | 19.0 | 41.5 | 0.0 | 28.6 | 0.0 |
| F190 | 0.0 | 0.0 | 0.0 | 100.0 | 0.0 | 0.0 | 0.0 | 0.0 | 0.0 | 0.0 | 0.0 | 0.0 |

TABLE 5-continued

Sequence conservation at S176 to I201 of MpLUC

| | | | | | | | | | | | | |
|---|---|---|---|---|---|---|---|---|---|---|---|---|
| A191 | 0.0 | 0.0 | 0.0 | 0.0 | 0.0 | 0.0 | 86.0 | 0.0 | 0.0 | 0.0 | 0.0 | 0.0 |
| D192 | 0.0 | 2.8 | 2.7 | 0.0 | 0.0 | 0.0 | 6.1 | 0.0 | 19.9 | 0.0 | 32.9 | 3.1 |
| K193 | 0.0 | 0.0 | 0.0 | 0.0 | 0.0 | 0.0 | 0.0 | 0.0 | 0.0 | 0.0 | 0.0 | 0.0 |
| I194 | 94.2 | 0.0 | 0.0 | 0.0 | 0.0 | 5.8 | 0.0 | 0.0 | 0.0 | 0.0 | 0.0 | 0.0 |
| Q195 | 0.0 | 0.0 | 2.4 | 0.0 | 0.0 | 0.0 | 0.0 | 0.0 | 0.0 | 0.0 | 0.0 | 0.0 |
| S196 | 0.0 | 0.0 | 0.0 | 0.0 | 0.0 | 0.0 | 2.7 | 27.3 | 0.0 | 0.0 | 34.1 | 0.0 |
| E197 | 0.0 | 0.0 | 0.0 | 0.0 | 0.0 | 0.0 | 2.9 | 0.0 | 0.0 | 0.0 | 0.0 | 0.0 |
| V198 | 2.8 | 84.6 | 0.0 | 0.0 | 0.0 | 3.1 | 6.1 | 3.5 | 0.0 | 0.0 | 0.0 | 0.0 |
| D199 | 0.0 | 0.0 | 0.0 | 0.0 | 0.0 | 0.0 | 1.4 | 2.7 | 0.0 | 0.0 | 3.1 | 0.0 |
| N200 | 0.0 | 1.7 | 0.0 | 0.0 | 0.0 | 0.0 | 0.1 | 0.0 | 28.3 | 0.0 | 10.1 | 0.0 |
| I201 | 87.6 | 6.1 | 0.0 | 0.0 | 0.0 | 0.0 | 0.0 | 0.0 | 0.0 | 0.0 | 0.0 | 0.0 |

| Residue | P | H | E | Q | D | N | K | R | Non |
|---|---|---|---|---|---|---|---|---|---|
| S176 | 0.0 | 0.0 | 0.0 | 0.0 | 0.0 | 15.1 | 0.0 | 0.0 | 0.0 |
| A177 | 0.0 | 0.0 | 11.0 | 0.0 | 54.2 | 0.0 | 5.3 | 0.0 | 0.0 |
| L178 | 0.0 | 0.0 | 0.0 | 5.3 | 0.0 | 0.0 | 6.1 | 0.0 | 0.0 |
| L179 | 0.0 | 0.0 | 0.0 | 0.0 | 0.0 | 0.0 | 0.0 | 0.0 | 0.0 |
| K180 | 0.0 | 0.0 | 0.0 | 0.0 | 0.0 | 0.0 | 88.7 | 0.0 | 0.0 |
| K181 | 0.0 | 0.0 | 0.0 | 0.0 | 5.3 | 0.0 | 86.2 | 0.0 | 0.0 |
| W182 | 0.0 | 0.0 | 0.0 | 0.0 | 0.0 | 0.0 | 0.0 | 0.0 | 0.0 |
| L183 | 0.0 | 0.0 | 0.0 | 0.0 | 0.0 | 0.0 | 0.0 | 0.0 | 0.0 |
| P184 | 100.0 | 0.0 | 0.0 | 0.0 | 0.0 | 0.0 | 0.0 | 0.0 | 0.0 |
| D185 | 0.0 | 0.0 | 0.0 | 35.8 | 27.4 | 0.0 | 5.8 | 0.0 | 0.0 |
| R186 | 0.0 | 0.0 | 0.0 | 0.0 | 0.0 | 0.0 | 0.0 | 100.0 | 0.0 |
| C187 | 0.0 | 0.0 | 0.0 | 0.0 | 0.0 | 0.0 | 0.0 | 0.0 | 0.0 |
| A188 | 0.0 | 0.0 | 0.0 | 0.0 | 0.0 | 0.0 | 16.6 | 2.8 | 0.0 |
| S189 | 0.0 | 0.0 | 0.0 | 8.1 | 0.0 | 2.8 | 0.0 | 0.0 | 0.0 |
| F190 | 0.0 | 0.0 | 0.0 | 0.0 | 0.0 | 0.0 | 0.0 | 0.0 | 0.0 |
| A191 | 0.0 | 0.0 | 0.0 | 6.1 | 0.0 | 0.0 | 2.7 | 5.3 | 0.0 |
| D192 | 0.0 | 0.0 | 0.0 | 0.0 | 27.0 | 5.5 | 0.0 | 0.0 | 0.0 |
| K193 | 0.0 | 0.0 | 0.0 | 8.0 | 0.0 | 8.6 | 83.5 | 0.0 | 0.0 |
| I194 | 0.0 | 0.0 | 0.0 | 0.0 | 0.0 | 0.0 | 0.0 | 0.0 | 0.0 |
| Q195 | 0.0 | 0.0 | 0.0 | 91.5 | 0.0 | 0.0 | 6.1 | 0.0 | 0.0 |
| S196 | 0.0 | 0.0 | 0.0 | 0.0 | 0.0 | 4.8 | 28.5 | 2.7 | 0.0 |
| E197 | 0.0 | 0.0 | 58.3 | 36.5 | 0.0 | 0.0 | 0.0 | 2.2 | 0.0 |
| V198 | 0.0 | 0.0 | 0.0 | 0.0 | 0.0 | 0.0 | 0.0 | 0.0 | 0.0 |
| D199 | 0.0 | 24.3 | 3.0 | 0.0 | 63.8 | 0.0 | 0.0 | 0.0 | 1.7 |
| N200 | 0.0 | 0.0 | 0.0 | 0.0 | 0.0 | 28.5 | 29.8 | 0.0 | 1.5 |
| I201 | 0.0 | 0.0 | 0.0 | 0.0 | 1.7 | 3.1 | 0.0 | 0.0 | 1.5 |

Figure 13:
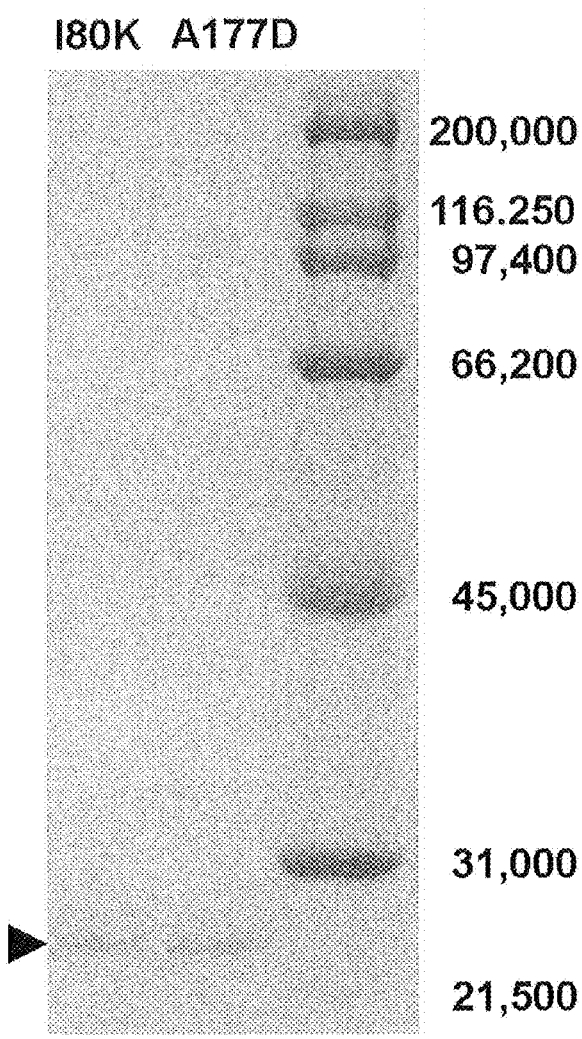
FIG. 13 shows an image of SDS-PAGE electrophoresis of enzymes purified by nickel affinity chromatography of a mutant enzyme in which isoleucine at the position 80 of luciferase is substituted to lysine and a mutant enzyme in which alanine at the position 177 is substituted to aspartic acid.

(2) Substitution of "a Hydrophobic Amino Acid that is Present in a Hydrophilic Domain of an α-Helix Structure or a Hydrophilic Amino Acid that is Present in a Hydrophobic Domain of the Region" to a Residue with High Conservation Mutations were introduced in the same manner as in Example 2 (2) so that the above amino acids were respectively substituted to other amino acids. E. coli JM109 (DE3) was transformed with each of the obtained mutagenized plasmids, inoculated to LB plates containing ampicillin and cultured at 37° C. for 16 hours. The obtained colonies were cultured in 5 mL of LB liquid medium containing IPTG, 0.5 μg/mL of IPTG was added at a cell turbidity of about 0.5 and the cells were cultured at 16° C. for 12 hours. After collecting the cells by centrifugation (10,000×g, 2 minutes, 4° C.), the cells were resuspended in 250 μL of 20 mM potassium phosphate buffer (pH 7.0) and a crude enzyme solution was prepared by ultrasonication and centrifugation. Coelenterazine was added to the obtained crude enzyme solution and luminescence was detected on a luminometer. As a result, luminescence was detected for the group of enzymes to which mutations were introduced as shown in FIG. 12. An increase of luminescence was also detected by introducing A177D mutation to the I80K mutant enzyme. The mutagenized enzyme was purified to a single protein as shown in FIG. 13 with His GraviTrap (manufactured by GE Healthcare Japan) and it was confirmed that the enzyme was an active-form mutant enzyme. From the above results, it was revealed that an active-form mutant enzyme could be expressed by substituting a hydrophobic amino acid that was present in a hydrophilic domain of an α-helix or a hydrophilic amino acid that was present in a hydrophobic domain of the region to an amino acid with high conservation.

Example 4

Figure 15:
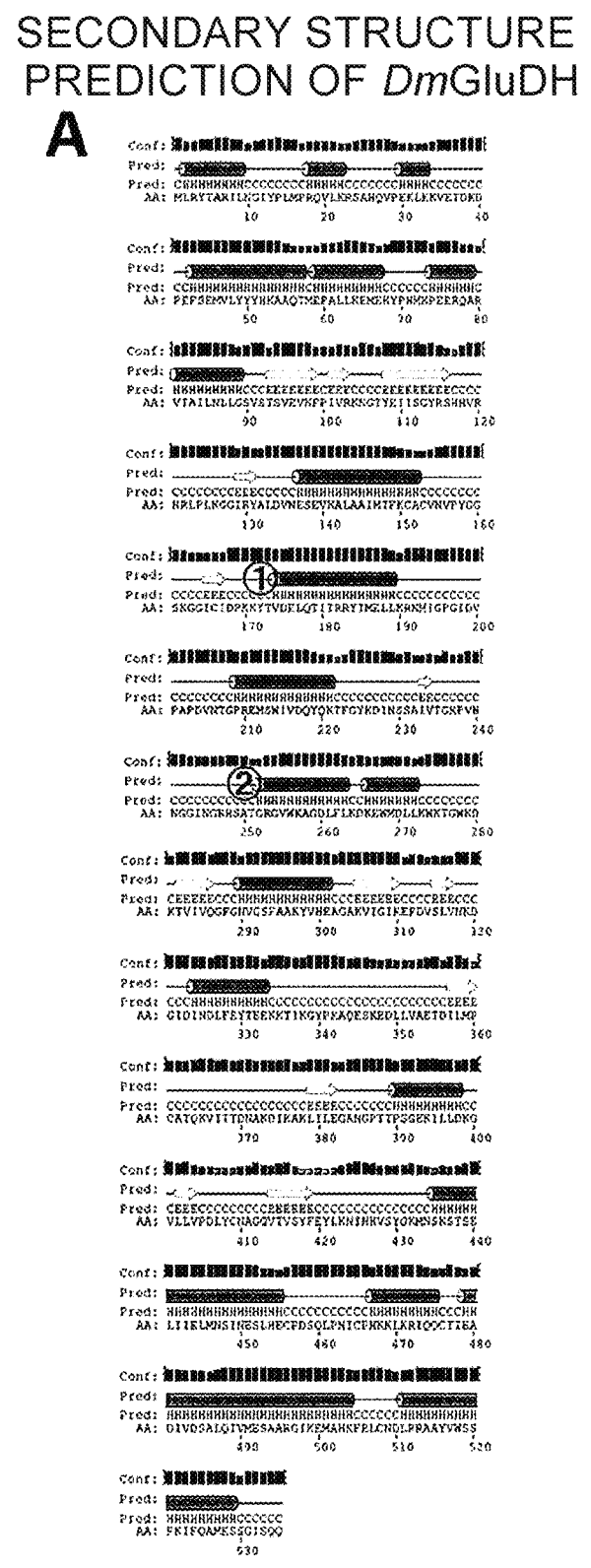

Expression of Amino Acid Decomposing Enzymes Derived from Drosophila melanogaster as Active-Form Mutant Enzymes by Focusing on α-Helices and Amino Acid Residue Conservation (1) Estimation of α-Helices by a Secondary Structure Predicting Programme, Drawing of a Helical Wheel and Search of Conserved Amino Acid Residues The secondary structures of the amino acid sequence (SEQ ID NO: 7) of ornithine decarboxylase (DmODC) and the amino acid sequence (SEQ ID NO: 9) of glutamate dehydrogenase (DmGluDH) derived from Drosophila melanogaster were predicted and α-helix sequences were specified (FIGS. 14 and 15). Further, analyses were carried out by focusing on the sequence conservation in the α-helix sequences and as a result, it was revealed that, as shown in Tables 6 and 7, the probability was high that in DmODC, leucine was conserved at the position 117 of lysine and glutamic acid was conserved at the position 176 of leucine, and in DmGluDH, aspartic acid was conserved at the position 174 of valine, tyrosine was conserved at the position 257 of lysine and glutamic acid was conserved at the position 261 of leucine.

TABLE 6

Sequence conservation at S111 to E118 and A171 to S180 of DmODC

| Residue | I | V | L | F | C | M | A | G | T | W | S | Y | P | H | E | Q | D | N | K | R | Non |
|---|---|---|---|---|---|---|---|---|---|---|---|---|---|---|---|---|---|---|---|---|---|
| S111 | 0.5 | 1.1 | 0.5 | 4.3 | 0.2 | 0.1 | 17.5 | 1.3 | 1.5 | 0.8 | 28.2 | 0.5 | 1.0 | 1.6 | 8.3 | 1.6 | 7.5 | 1.5 | 7.0 | 13.2 | 1.9 |
| H112 | 3.7 | 0.2 | 0.6 | 3.2 | 0.4 | 0.2 | 3.1 | 1.1 | 0.3 | 0.1 | 2.8 | 4.2 | 0.1 | 8.4 | 34.6 | 10.7 | 23.4 | 0.8 | 0.1 | 0.1 | 1.9 |
| L113 | 59.3 | 7.0 | 14.5 | 0.4 | 0.1 | 10.4 | 1.3 | 0.0 | 0.5 | 0.0 | 0.4 | 1.4 | 0.0 | 0.1 | 0.5 | 0.4 | 0.2 | 0.0 | 0.6 | 1.0 | 1.9 |
| E114 | 2.0 | 1.7 | 2.3 | 0.1 | 0.1 | 0.2 | 18.7 | 0.9 | 1.2 | 0.2 | 1.1 | 0.3 | 0.1 | 0.7 | 12.2 | 3.0 | 6.7 | 1.0 | 18.3 | 27.4 | 1.9 |
| Y115 | 0.4 | 1.0 | 6.0 | 11.3 | 0.4 | 1.3 | 9.6 | 0.2 | 1.5 | 0.7 | 0.6 | 31.6 | 0.1 | 5.2 | 7.7 | 6.8 | 1.3 | 0.5 | 0.8 | 11.3 | 1.9 |
| A116 | 0.4 | 3.2 | 0.9 | 6.1 | 1.0 | 0.0 | 79.6 | 2.4 | 0.2 | 0.1 | 0.6 | 2.6 | 0.1 | 0.0 | 0.4 | 0.0 | 0.2 | 0.1 | 0.1 | 0.1 | 2.0 |
| K117 | 3.2 | 4.0 | 30.5 | 5.3 | 0.6 | 0.8 | 22.5 | 0.4 | 0.3 | 0.5 | 2.6 | 13.3 | 0.1 | 6.0 | 1.3 | 0.8 | 0.2 | 0.5 | 2.1 | 3.2 | 1.9 |
| E118 | 0.1 | 0.6 | 1.0 | 0.6 | 0.1 | 0.2 | 13.9 | 1.8 | 2.7 | 0.1 | 9.1 | 0.2 | 0.0 | 1.1 | 23.3 | 7.0 | 7.6 | 4.5 | 18.8 | 5.5 | 2.1 |
| A171 | 3.4 | 11.8 | 9.0 | 1.1 | 9.1 | 1.6 | 24.9 | 1.3 | 3.3 | 1.0 | 5.0 | 0.6 | 3.9 | 0.5 | 4.5 | 0.7 | 0.9 | 0.8 | 2.4 | 11.8 | 2.4 |
| A172 | 1.7 | 8.1 | 4.1 | 0.3 | 2.3 | 3.9 | 10.3 | 2.6 | 2.1 | 0.1 | 2.7 | 1.1 | 6.0 | 1.3 | 17.4 | 3.3 | 8.0 | 1.3 | 4.3 | 16.5 | 4.7 |
| A173 | 4.1 | 15.6 | 14.1 | 0.9 | 0.4 | 6.7 | 5.8 | 2.7 | 2.0 | 0.1 | 2.6 | 0.4 | 3.4 | 10.3 | 7.6 | 1.9 | 12.0 | 1.1 | 1.5 | 3.9 | 3.0 |
| L174 | 4.9 | 9.0 | 50.8 | 6.7 | 0.2 | 1.3 | 1.8 | 0.7 | 0.2 | 0.0 | 0.1 | 20.4 | 0.1 | 0.0 | 1.7 | 0.1 | 0.4 | 0.1 | 0.2 | 0.3 | 1.3 |
| M175 | 5.0 | 3.1 | 55.4 | 0.6 | 0.5 | 2.7 | 12.3 | 0.2 | 0.8 | 0.0 | 0.7 | 0.5 | 0.5 | 0.6 | 2.9 | 2.6 | 1.3 | 0.6 | 3.3 | 5.0 | 1.1 |
| L176 | 5.7 | 4.2 | 8.5 | 0.8 | 0.2 | 1.1 | 6.2 | 1.0 | 2.0 | 4.1 | 1.9 | 2.7 | 0.8 | 4.3 | 21.8 | 7.0 | 3.3 | 0.9 | 6.1 | 15.9 | 1.4 |
| L177 | 3.6 | 5.4 | 14.5 | 1.1 | 4.2 | 1.9 | 34.5 | 0.2 | 4.5 | 0.2 | 1.6 | 3.2 | 0.1 | 3.9 | 2.0 | 1.9 | 0.6 | 2.2 | 3.2 | 9.8 | 1.6 |
| A178 | 1.2 | 2.5 | 1.9 | 0.1 | 0.6 | 0.6 | 68.2 | 0.9 | 1.0 | 0.0 | 2.0 | 0.3 | 0.1 | 1.7 | 0.9 | 1.2 | 0.6 | 0.7 | 10.0 | 4.4 | 1.1 |
| K179 | 0.5 | 1.6 | 0.9 | 0.4 | 0.2 | 0.2 | 9.1 | 1.6 | 3.6 | 0.0 | 5.3 | 0.4 | 0.1 | 5.7 | 4.5 | 6.1 | 3.1 | 3.5 | 33.9 | 17.4 | 2.2 |
| S180 | 0.3 | 0.7 | 19.5 | 0.4 | 0.3 | 2.4 | 8.2 | 1.5 | 2.8 | 0.3 | 9.3 | 0.6 | 0.1 | 1.6 | 19.9 | 5.9 | 9.5 | 1.7 | 5.5 | 7.0 | 2.4 |

TABLE 7

Sequence conservation at V174 to L189 and G252 to L261 of DmGluDH

| Residue | I | V | L | F | C | M | A | G | T | W | S | Y |
|---|---|---|---|---|---|---|---|---|---|---|---|---|
| V174 | 4.6 | 2.1 | 3.0 | 6.9 | 0.1 | 2.2 | 3.1 | 0.4 | 3.2 | 0.0 | 2.9 | 0.1 |
| D175 | 0.1 | 0.2 | 1.4 | 0.5 | 0.1 | 1.5 | 14.8 | 20.2 | 2.3 | 1.0 | 9.5 | 0.8 |
| E176 | 0.0 | 0.1 | 0.0 | 0.0 | 0.0 | 0.1 | 0.1 | 0.0 | 0.2 | 0.0 | 0.1 | 0.0 |
| L177 | 12.0 | 14.2 | 63.5 | 0.0 | 0.1 | 1.7 | 0.1 | 0.1 | 0.8 | 0.1 | 0.0 | 0.0 |
| Q178 | 0.1 | 0.1 | 0.3 | 0.1 | 0.1 | 18.5 | 0.1 | 0.0 | 0.0 | 0.0 | 0.0 | 0.1 |
| T179 | 0.1 | 0.2 | 2.1 | 0.0 | 0.0 | 0.2 | 4.3 | 1.1 | 0.0 | 0.0 | 1.2 | 0.0 |
| I180 | 22.2 | 5.6 | 49.0 | 18.6 | 0.0 | 2.3 | 0.1 | 0.0 | 0.0 | 0.1 | 0.1 | 0.1 |
| T181 | 0.7 | 1.6 | 0.1 | 0.2 | 17.8 | 0.8 | 2.9 | 0.0 | 52.4 | 0.0 | 21.7 | 0.0 |
| R182 | 0.0 | 0.0 | 0.3 | 0.0 | 0.0 | 0.0 | 0.1 | 0.1 | 0.0 | 0.0 | 0.1 | 0.0 |
| R183 | 0.0 | 4.0 | 0.0 | 0.0 | 0.0 | 0.0 | 11.0 | 18.1 | 0.5 | 0.0 | 15.9 | 0.0 |
| Y184 | 0.3 | 0.1 | 0.9 | 48.8 | 0.0 | 0.2 | 0.1 | 0.0 | 0.0 | 0.8 | 0.1 | 46.4 |
| T185 | 7.6 | 15.6 | 0.1 | 0.9 | 0.1 | 20.0 | 14.7 | 0.3 | 38.0 | 0.0 | 0.8 | 0.0 |
| M186 | 2.2 | 1.7 | 4.5 | 1.0 | 0.3 | 3.7 | 4.3 | 0.1 | 16.5 | 0.1 | 20.5 | 4.4 |
| E187 | 0.2 | 0.3 | 0.8 | 0.0 | 0.1 | 0.5 | 21.9 | 2.7 | 0.2 | 0.1 | 1.1 | 0.4 |
| L188 | 44.0 | 2.8 | 43.8 | 2.9 | 0.1 | 3.1 | 0.2 | 0.0 | 0.2 | 0.1 | 0.2 | 0.1 |
| L189 | 6.7 | 2.2 | 0.2 | 1.5 | 2.7 | 0.8 | 20.0 | 13.2 | 0.7 | 2.0 | 19.7 | 9.2 |
| G252 | 0.0 | 0.0 | 0.0 | 0.0 | 0.0 | 0.0 | 14.8 | 81.3 | 0.0 | 0.0 | 2.8 | 0.0 |
| R253 | 0.1 | 0.1 | 8.5 | 5.0 | 0.1 | 0.6 | 0.4 | 0.0 | 1.0 | 0.3 | 0.3 | 20.4 |
| G254 | 0.0 | 0.2 | 0.1 | 0.0 | 0.0 | 0.0 | 0.0 | 92.1 | 0.0 | 0.0 | 6.3 | 0.0 |
| V255 | 1.7 | 63.9 | 12.1 | 0.0 | 3.8 | 0.1 | 6.8 | 2.6 | 3.6 | 0.0 | 0.5 | 0.0 |
| W256 | 3.4 | 20.7 | 8.1 | 26.8 | 2.3 | 5.4 | 11.4 | 0.6 | 7.5 | 0.0 | 1.6 | 4.6 |
| K257 | 19.6 | 16.2 | 7.1 | 9.3 | 0.1 | 0.4 | 0.3 | 0.0 | 2.3 | 0.0 | 0.2 | 32.6 |
| A258 | 5.0 | 14.7 | 4.0 | 12.2 | 8.4 | 2.0 | 15.7 | 11.2 | 15.6 | 0.1 | 5.0 | 4.0 |
| G259 | 24.1 | 9.9 | 14.3 | 0.3 | 0.8 | 1.5 | 17.8 | 12.5 | 16.3 | 0.0 | 0.6 | 0.1 |
| D260 | 0.6 | 2.2 | 6.2 | 0.3 | 2.8 | 2.0 | 2.4 | 0.5 | 1.0 | 0.1 | 3.5 | 0.3 |
| L261 | 0.5 | 1.4 | 1.6 | 1.0 | 0.4 | 0.1 | 10.7 | 0.1 | 0.9 | 0.1 | 2.8 | 0.9 |
| F262 | 3.0 | 8.6 | 12.3 | 11.8 | 0.6 | 14.0 | 40.4 | 0.4 | 1.1 | 1.9 | 0.4 | 2.2 |

| Residue | P | H | E | Q | D | N | K | R | Non |
|---|---|---|---|---|---|---|---|---|---|
| V174 | 5.1 | 0.8 | 15.8 | 5.0 | 24.3 | 3.9 | 8.7 | 6.1 | 1.8 |
| D175 | 0.7 | 6.1 | 1.9 | 2.3 | 2.7 | 10.7 | 2.9 | 18.6 | 1.8 |
| E176 | 0.0 | 0.1 | 95.3 | 0.8 | 0.7 | 0.3 | 0.0 | 0.1 | 1.8 |
| L177 | 0.1 | 0.1 | 0.0 | 0.9 | 0.0 | 0.1 | 3.5 | 0.9 | 1.8 |
| Q178 | 0.1 | 0.1 | 0.1 | 75.7 | 1.2 | 0.0 | 0.5 | 0.1 | 1.8 |
| T179 | 0.0 | 0.5 | 0.9 | 3.0 | 0.3 | 1.5 | 12.0 | 71.7 | 1.8 |
| I180 | 0.0 | 0.0 | 0.2 | 0.0 | 0.0 | 0.1 | 0.1 | 0.0 | 1.7 |
| T181 | 0.1 | 0.0 | 0.0 | 0.0 | 0.0 | 0.1 | 0.0 | 0.1 | 1.7 |
| R182 | 0.0 | 0.2 | 0.1 | 18.3 | 0.0 | 0.0 | 1.1 | 78.0 | 1.8 |
| R183 | 0.0 | 0.5 | 0.3 | 0.5 | 0.0 | 0.8 | 2.8 | 43.2 | 2.2 |
| Y184 | 0.0 | 0.0 | 0.0 | 0.0 | 0.0 | 0.0 | 0.1 | 0.1 | 2.2 |
| T185 | 0.0 | 0.0 | 0.0 | 0.0 | 0.0 | 0.0 | 0.1 | 0.1 | 1.8 |
| M186 | 0.1 | 1.3 | 5.5 | 10.4 | 2.5 | 0.8 | 1.8 | 16.4 | 1.9 |
| E187 | 0.0 | 0.2 | 60.5 | 1.4 | 0.2 | 0.4 | 5.1 | 1.8 | 2.2 |
| L188 | 0.0 | 0.0 | 0.0 | 0.3 | 0.0 | 0.1 | 0.0 | 0.3 | 2.0 |
| L189 | 0.1 | 5.4 | 1.1 | 4.1 | 0.1 | 2.0 | 0.6 | 6.1 | 1.8 |
| G252 | 0.0 | 0.0 | 0.1 | 0.0 | 0.0 | 0.0 | 0.0 | 0.0 | 1.0 |
| R253 | 0.0 | 0.4 | 0.3 | 2.9 | 0.1 | 0.0 | 6.8 | 51.7 | 1.0 |

TABLE 7-continued

Sequence conservation at V174 to L189 and G252 to L261 of DmGluDH

| | I | V | L | F | C | M | A | G | T | W | S | Y | P | H | E | Q | D | N | K | R | Non |
|---|---|---|---|---|---|---|---|---|---|---|---|---|---|---|---|---|---|---|---|---|---|
| G254 | | | | | 0.0 | 0.0 | 0.0 | 0.0 | 0.0 | 0.0 | 0.0 | | | | | | | 0.1 | | | 1.2 |
| V255 | | | | | 0.0 | 0.0 | 0.0 | 0.1 | 0.3 | 2.8 | 0.0 | | | | | | | 0.0 | | | 1.6 |
| W256 | | | | | 0.0 | 0.1 | 0.1 | 4.8 | 0.0 | 1.3 | 0.1 | | | | | | | 0.1 | | | 1.5 |
| K257 | | | | | 0.0 | 9.9 | 0.2 | 0.4 | 0.1 | 0.3 | 0.0 | | | | | | | 0.1 | | | 1.5 |
| A258 | | | | | 0.0 | 0.0 | 0.0 | 0.0 | 0.0 | 0.4 | 0.0 | | | | | | | 0.1 | | | 1.5 |
| G259 | | | | | 0.0 | 0.0 | 0.0 | 0.0 | 0.0 | 0.0 | 0.0 | | | | | | | 0.1 | | | 1.5 |
| D260 | | | | | 0.0 | 1.1 | 24.5 | 9.7 | 3.1 | 3.0 | 7.7 | | | | | | | 27.2 | | | 2.0 |
| L261 | | | | | 0.0 | 2.4 | 55.1 | 5.1 | 0.7 | 10.6 | 1.2 | | | | | | | 1.9 | | | 2.7 |
| F262 | | | | | 0.1 | 0.1 | 0.1 | 0.2 | 0.0 | 0.0 | 0.1 | | | | | | | 0.0 | | | 2.5 |

(2) Introduction of Mutations to the Residues Selected by the Method of the Present Invention and Activity Assay Mutagenesis was made in the same manner as in Example 2 (2) so that each residue was substituted to other amino acids. Thereafter, the obtained colonies were cultured and a crude enzyme solution was prepared. As a result, although enzyme activities were not detected for enzymes before mutagenesis because the enzymes were not expressed as soluble proteins, mutant enzymes of DmODC in which lysine at the position of 117 was substituted to leucine and leucine at the position 176 was substituted to glutamic acid had ornithine decarboxylase activity of 0.45 U/mL and 0.04 U/mL, respectively. Mutant enzymes of DmGluDH in which valine at the position 174 was substituted to aspartic acid, leucine at the position 257 was substituted to tyrosine and leucine at the position 261 was substituted to glutamic acid had glutamate dehydrogenase activity of 0.14 U/mL, 0.91 U/mL and 0.05 U/mL, respectively. From the above results, it was revealed that, similar to Example 3, an active-form mutant enzyme could be expressed by substituting a hydrophobic amino acid that was present in a hydrophilic domain of an α-helix or a hydrophilic amino acid that was present in a hydrophobic domain of the region to an amino acid with high conservation, even for other enzymes.

Example 5

The procedures in Example 1 (1) to (3) were repeated to examine the expression level of insoluble proteins and the expression level of soluble proteins for the wild type enzyme (WT) and the mutant enzymes (V455D and V455Q) in $E.$ $coli$. The crude enzyme solution was centrifuged to obtain a supernatant which was a soluble fraction (soluble protein) and a pellet (precipitate) which was an insoluble fraction (insoluble protein).

Figure 16:
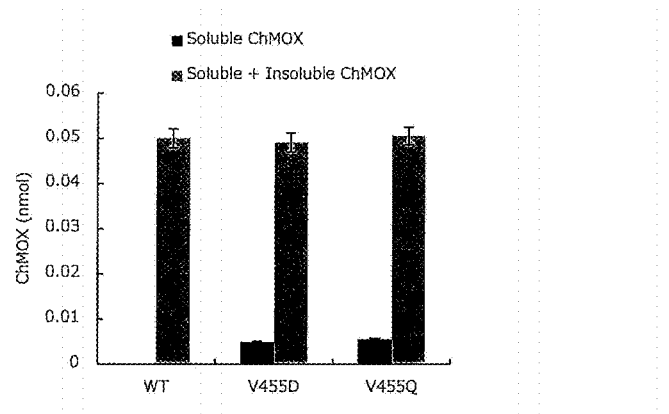
FIG. 16 shows the test results of the expression level of mandelonitrile oxidase; and soluble ChMOX indicates supernatant (soluble fraction) and Soluble+Insoluble ChMOX indicates the entire expression level (supernatant (soluble fraction)+pellet (insoluble fraction)).

In order to examine the expression level of the wild type enzyme (WT) and mutant enzymes (V455D and V455Q) of mandelonitrile oxidase derived from $Chamberlinius$ $hualienensis$ in $E.$ $coli$, the assay was carried out by western blotting using an antibody. After inducing under the same conditions and preparing crude enzyme solutions (buffer: 10 mM potassium phosphate buffer (pH 7.0)), the supernatant (soluble fraction) and supernatant (soluble fraction)+pellet (insoluble fraction) were electrophoresed by SDS-PAGE and transferred onto PVDF membranes. By using an antibody anti-His tag mAb HRP DirectT (MBL Co., Ltd., Nagoya, Japan) directed to the histidine tag added to proteins, the amount of the enzyme in each fraction was determined. As a result, it was revealed that, although the total expression levels were similar for all enzymes, there was a difference in the expression level in the soluble fraction between mutant enzymes (V455D and V455Q) and the wild type enzyme (WT) (FIG. 16).

Example 6

Expression of Human Growth Hormone as a Soluble Protein

It is known that human growth hormone (hGH) is expressed as an insoluble protein in $E.$ $coli$. The conformation (PDB ID:3HHR) for hGH has been published and the protein contains 7 α-helix structures. In order to express the protein in a soluble form in $E.$ $coli$, the sequence conservation of the α-helix sequences was calculated on INTMSAlign (NPL 7). The sequence conservation was calculated under the following conditions. The sequence of the wild type enzyme is entered in the section "Sequence" on the BLAST site, 5000 is selected as the value of "Max target sequences" of the "General Parameters" under the "Algorithm parameters" section below and 1.0E-3 is entered as the value of "Expect threshold" and then the BLAST search is started, thereby other proteins with high identity are selected. By downloading all the obtained protein sequences having high identity in FASTA format and entering the sequences to INTMSAlign, sequence conservation was calculated.

As a result, leucine at the position 46, phenylalanine at the position of 55, leucine at the position of 82, leucine at the position of 88, arginine at the position of 95, valine at the position of 97 and isoleucine at the position of 114 were found to be amino acids with low conservation and it was revealed that lysine, histidine, arginine, glutamic acid, serine, glutamic acid and lysine, respectively, were conserved at high percentages.

TABLE 8

Sequence conservation at L46, F55, L82, L88, R95, V97 and I114 of hGH

| Residue | I | V | L | F | C | M | A | G | T | W | S | Y | P | H | E | Q | D | N | K | R | Non |
|---|---|---|---|---|---|---|---|---|---|---|---|---|---|---|---|---|---|---|---|---|---|
| L46 | 3.7 | 2.1 | 8.3 | 10.7 | 0.2 | 2.0 | 3.5 | 0.4 | 1.1 | 0.2 | 6.5 | 2.3 | 0.6 | 0.6 | 0.9 | 9.6 | 0.2 | 7.3 | 12.2 | 1.8 | 25.9 |
| F55 | 2.3 | 0.3 | 1.0 | 20.2 | 0.2 | 0.4 | 0.6 | 0.1 | 0.5 | 0.1 | 0.7 | 11.6 | 1.3 | 30.6 | 0.2 | 0.3 | 0.0 | 14.9 | 0.1 | 0.2 | 14.5 |
| L82 | 2.5 | 10.0 | 23.8 | 0.2 | 0.2 | 4.2 | 2.3 | 6.8 | 1.7 | 0.0 | 12.1 | 0.2 | 0.0 | 0.7 | 0.3 | 0.3 | 0.2 | 2.5 | 3.7 | 19.8 | 8.4 |
| L88 | 3.8 | 0.9 | 33.2 | 1.1 | 0.0 | 0.8 | 0.6 | 0.4 | 0.9 | 0.1 | 3.2 | 0.6 | 0.4 | 0.5 | 19.2 | 1.4 | 2.5 | 16.0 | 4.8 | 1.1 | 8.4 |
| R95 | 2.1 | 16.9 | 1.2 | 0.0 | 0.1 | 0.2 | 5.1 | 2.8 | 1.3 | 0.3 | 41.1 | 0.6 | 0.4 | 1.3 | 0.5 | 3.9 | 0.3 | 3.1 | 0.3 | 9.4 | 9.2 |
| V97 | 5.4 | 28.3 | 1.8 | 0.2 | 0.2 | 5.0 | 4.6 | 4.8 | 9.6 | 0.0 | 4.7 | 0.7 | 0.8 | 2.6 | 16.2 | 0.5 | 0.4 | 0.7 | 0.4 | 0.6 | 12.4 |
| L114 | 0.8 | 0.4 | 9.2 | 0.3 | 0.0 | 3.4 | 1.0 | 1.2 | 0.4 | 0.6 | 0.4 | 2.9 | 0.0 | 2.9 | 7.2 | 9.3 | 1.3 | 0.9 | 41.4 | 3.5 | 12.9 |

Figure 17:
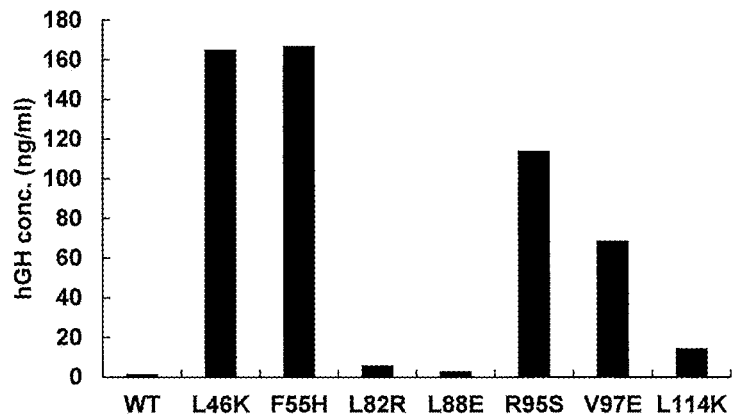
FIG. 17 shows the test results of the expression level of soluble hGH mutant protein using hGH ELISA.
Figures 18, 19:
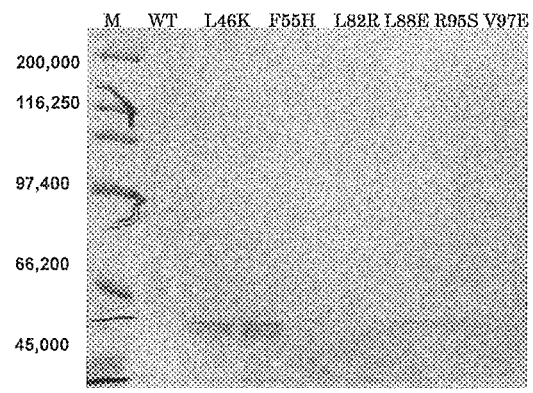
FIG. 18 shows SDS-PAGE after purification.
FIG. 19 shows the amino acid sequence of hGH (SEQ ID NO: 11).

Substitution of "a hydrophobic amino acid that is present in a hydrophilic domain of an α-helix structure or a hydrophilic amino acid that is present in a hydrophobic domain of the region" to a residue with high conservation Mutations were introduced in the same manner as in Example 2 (2) so that the above amino acids were respectively substituted to other amino acids. *E. coli* BL21 (DE3) was transformed with each of the obtained mutagenized plasmids, inoculated to LB plates containing ampicillin and cultured at 37° C. for 16 hours. The obtained colonies were cultured in 5 mL of LB liquid medium containing IPTG, 0.5 μg/mL of IPTG was added at a cell turbidity of about 0.5 and the cells were cultured at 16° C. for 12 hours. After collecting the cells by centrifugation (10,000×g, 2 minutes, 4° C.), the cells were resuspended in 250 μL of 20 mM potassium phosphate buffer (pH 7.0) and a crude enzyme solution was prepared by ultrasonication and centrifugation. As a result of analysis of the expression level in the obtained crude extract by hGH ELISA, expression was detected in the group of proteins to which mutations were introduced as shown in FIG. 17. The mutagenized proteins were purified to a single protein as shown in FIG. 18 with His GraviTrap (manufactured by GE Healthcare Japan) and it was confirmed that the proteins were soluble proteins. From the above results, it was revealed that the expression level of soluble proteins could be increased by substituting a hydrophobic amino acid that was present in a hydrophilic domain of an α-helix or a hydrophilic amino acid that was present in a hydrophobic domain of the region to an amino acid with high conservation.

INDUSTRIAL APPLICABILITY

The present invention is useful in the field relating to preparation of enzyme proteins.

SEQUENCE LISTING FREE TEXT

SEQ ID NO: 1: Mandelonitrile oxidase gene derived from *Chamberlinius hualienensis*
SEQ ID NO: 2: Amino acid sequence of mandelonitrile oxidase derived from *Chamberlinius hualienensis*
SEQ ID NO: 3: Amino acid sequence of arginine decarboxylase derived from *Arabidopsis thaliana*
SEQ ID NO: 4: Arginine decarboxylase gene derived from *Arabidopsis thaliana*
SEQ ID NO: 5: Amino acid sequence of luciferase (MpLUC) 1-1 derived from *Metridia pacifica*
SEQ ID NO: 6: Luciferase (MpLUC) 1-1 gene derived from *Metridia pacifica* SEQ ID NO: 7: Amino acid sequence of ornithine decarboxylase (DmODC) derived from *Drosophila melanogaster*
SEQ ID NO: 8: Ornithine decarboxylase (DmODC) gene derived from *Drosophila melanogaster*
SEQ ID NO: 9: Amino acid sequence of glutamate dehydrogenase (DmGluDH) derived from *Drosophila melanogaster*
SEQ ID NO: 10: Glutamate dehydrogenase (DmGluDH) gene derived from *Drosophila melanogaster*
SEQ ID NO: 11: Amino acid sequence of hGH

The invention claimed is:

1. A producing method of an active-form mutant enzyme comprising:
   (1) specifying a protein of which native form exhibits an enzyme activity but which exhibits 10% or less enzyme activity of the enzyme activity exhibited by the protein in the native form, when expressing a gene of the protein in a heterologous expression system to thereby specify an inactive-form enzyme;
   (2a) specifying an α-helix structure region of the inactive-form enzyme specified in step (1), specifying a hydrophilic domain and/or a hydrophobic domain of the specified α-helix structure region, and specifying a hydrophobic amino acid that is present in the hydrophilic domain and/or a hydrophilic amino acid that is present in the hydrophobic domain;
   (3a) preparing a gene that codes for an amino acid sequence in which at least one hydrophobic amino acid that is present in the hydrophilic domain of an α-helix structure region in the inactive-form enzyme is substituted, wherein the amino to be substituted acid is substituted to an amino acid with higher hydrophilicity or lower hydrophobicity,
   and/or
   at least one hydrophilic amino acid that is present in the hydrophobic domain of the α-helix structure region is substituted, wherein the amino acid to be substituted is substituted to an amino acid with higher hydrophobicity or lower hydrophilicity;
   (4a) expressing, in a heterologous expression system, the gene prepared in step (3a) to obtain a protein and selecting from the obtained proteins, a protein that exhibits 10 times or more of enzyme activity than that of the inactive-form enzyme to thereby specify an active form mutant enzyme.

2. The producing method according to claim 1, wherein in the step (2a), the hydrophilic domain and/or hydrophobic domain is specified by drawing a helical wheel of the α-helix structure region by using a method for predicting secondary structure of a protein, aligning amino acids at positions 1, 5, 2, 6, 3, 7 and 4 on the helical wheel in this order to form a sequence and repeating the procedure to form at least two amino acid sequences each of which has 7 amino acids, wherein the second sequence has 5 or more amino acids;
   in the amino acid sequence region where at least two sequences are aligned, defining a row in which the sum of the hydropathy index of the amino acids therein is 0 or more as a hydrophobic row and defining a row in which the sum of the hydropathy index of the amino acids therein is less than 0 as a hydrophilic row; and
   defining a bunch of 3 or 4 consecutive hydrophobic rows as the hydrophobic domain and defining a bunch of 4 or 3 consecutive hydrophilic rows as the hydrophilic domain, wherein the sum of the hydropathy index of any one row that is internal to 4 hydrophobic rows in the hydrophobic domain may be less than 0 and the sum of the hydropathy index of any one row that is internal to 4 hydrophilic rows in the hydrophilic domain may be 0 or more.

3. The producing method according to claim 1, wherein in step (2a), an amino acid among amino acids in the hydrophilic domain, having the hydropathy index of 0 or more is specified as a hydrophobic amino acid and an amino acid, among amino acids in the hydrophobic domain, having the hydropathy index of less than 0 is specified as a hydrophilic amino acid.

4. The producing method according to claim 1, wherein in the step (3a), the hydrophobic amino acid that is present in the hydrophilic domain is substituted to an amino acid with lower hydropathy index than the amino acid to be substituted, and
   the hydrophilic amino acid that is present in the hydrophobic domain is substituted to an amino acid with higher hydropathy index than the amino acid to be substituted.

5. The producing method according to claim 1, wherein in step (3a), the hydrophobic amino acid that is present in the hydrophilic domain is substituted to an amino acid with lower hydropathy index than the amino acid to be substituted and with a hydropathy index of less than 0, and
   the hydrophilic amino acid that is present in the hydrophobic domain is substituted to an amino acid with higher hydropathy index than the amino acid to be substituted and with a hydropathy index of 0 or more.

6. The producing method according to claim 1, wherein in step (3a), the amino acid is substituted to an amino acid with higher conservation in sequence identity than the amino acid to be substituted.

7. The producing method according to claim 1, wherein in the step (3a), the amino acid substitution is carried out for any of a plurality of amino acids and in step (4a), the active-form mutant enzyme or the soluble mutant protein is selected from a plurality of proteins in which any of the amino acids are substituted.

* * * * *